(12) United States Patent
Iwasawa et al.

(10) Patent No.: US 6,846,895 B2
(45) Date of Patent: Jan. 25, 2005

(54) POLYSILOXANE, METHOD OF MANUFACTURING SAME, SILICON-CONTAINING ALICYCLIC COMPOUND, AND RADIATION-SENSITIVE RESIN COMPOSITION

(75) Inventors: Haruo Iwasawa, Mie (JP); Tsutomu Shimokawa, Mie (JP); Akihiro Hayashi, Mie (JP); Satoru Nishiyama, Mie (JP)

(73) Assignee: JSR Corporation, Tokyo (JP)

( * ) Notice: Subject to any disclaimer, the term of this patent is extended or adjusted under 35 U.S.C. 154(b) by 10 days.

(21) Appl. No.: 10/364,351

(22) Filed: Feb. 12, 2003

(65) Prior Publication Data

US 2003/0191268 A1 Oct. 9, 2003

Related U.S. Application Data

(62) Division of application No. 09/824,224, filed on Apr. 3, 2001, now Pat. No. 6,531,260.

(30) Foreign Application Priority Data

| Apr. 7, 2000 | (JP) | 2000-107207 |
| Sep. 25, 2000 | (JP) | 2000-291089 |
| Oct. 19, 2000 | (JP) | 2000-318752 |

(51) Int. Cl.$^7$ .............................................. C08G 77/12
(52) U.S. Cl. .............................. 528/31; 528/37; 528/38; 556/460; 556/479; 556/458
(58) Field of Search .............................. 528/31, 37, 38; 556/460, 479, 458

(56) References Cited

U.S. PATENT DOCUMENTS

| 5,338,640 A | 8/1994 | Aoai et al. |
| 5,338,818 A | 8/1994 | Brunsvold et al. |
| 5,612,170 A | 3/1997 | Takemura et al. |
| 6,296,985 B1 | 10/2001 | Mizutani et al. |
| 6,531,260 B2 | 3/2003 | Iwasawa et al. |

FOREIGN PATENT DOCUMENTS

| EP | 0 410 606 A2 | 1/1991 |
| JP | 61-192709 * | 8/1986 |

OTHER PUBLICATIONS

Patent Abstracts of Japan vol. 016, No. 272 (P–1373), Jun. 18, 1992 and JP 04 070662 A (Nippon Telegr & Teleph Corp), Mar. 5, 1992, abstract only.

Patent Abstracts of Japan vol. 016, No. 445 (P–1422), Sep. 17, 1992 and JP 04 155344 A (Oki Electric Ind Co Ltd), May 28, 1992, abstract only.

Patent Abstracts of Japan vol. 018, No. 166 (P–1713), Mar. 18, 1994 and JP 05 333553 A (Oki Electric Ind Co Ltd), Dec. 17, 1993, abstract only.

* cited by examiner

Primary Examiner—Kuo-Liang Peng
(74) Attorney, Agent, or Firm—Piper Rudnick LLP; Steven B. Kelber

(57) ABSTRACT

A novel polysiloxane having the following structural units (I) and/or (II) and the structural unit (III),

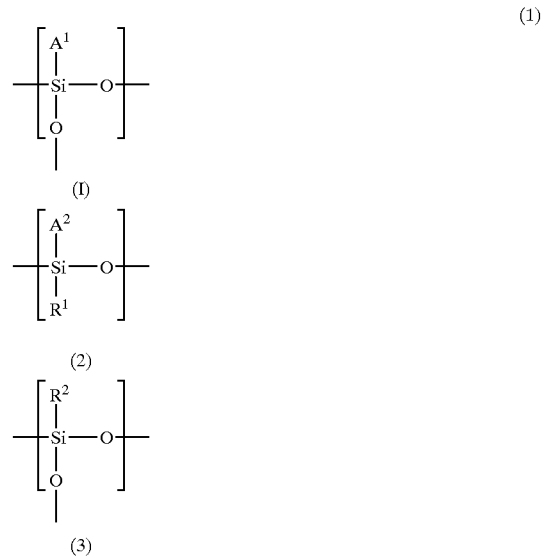

wherein $A^1$ and $A^2$ are an acid-dissociable monovalent organic group, $R^1$ is hydrogen, monovalent (halogenated) hydrocarbon, halogen, or amino, $R^2$ is monovalent (halogenated) hydrocarbon group, or halogen. A method of preparing such a polysiloxane, a silicon-containing alicyclic compound providing this polysiloxane, and a radiation-sensitive resin composition comprising this polysiloxane are also provided. The polysiloxane is useful as a resin component for a resist material, effectively senses radiation with a short wavelength, exhibits high transparency to radiation and superior dry etching properties, and excels in basic resist properties required for resist materials such as high sensitivity, resolution, developability, etc.

20 Claims, No Drawings

POLYSILOXANE, METHOD OF MANUFACTURING SAME, SILICON-CONTAINING ALICYCLIC COMPOUND, AND RADIATION-SENSITIVE RESIN COMPOSITION

RELATED APPLICATION

This application is a divisional application of U.S. application Ser. No. 09/824,224 filed on Apr. 3, 2001, now U.S. Pat. No. 6,531,260.

BACKGROUND OF THE INVENTION

1. Field of the Invention

The present invention relates to a polysiloxane and a method of preparing the same, a silicon-containing alicyclic compound, and a radiation-sensitive resin composition containing the polysiloxane suitable for use in microfabrication utilizing radiation.

2. Description of the Background Art

A recent strong demand for high density and highly integrated LSIs accelerates miniaturization of wiring patterns.

Using short wave rays in a lithographic process is one method for miniaturizing wiring patterns. In recent years, deep ultraviolet rays typified by a KrF excimer laser (wavelength: 248 nm) or an ArF excimer laser (wavelength: 193 nm), electron beams, X rays, and the like are being used in place of ultraviolet rays such as g-line (wavelength: 436 nm), i-line (wavelength: 365 nm), etc. Use of an F2 excimer laser (wavelength: 157 nm) is also being studied.

Novolac resins, poly(vinylphenol), and the like have been used as resin components for conventional resist compositions. However, because these resins exhibit strong absorbance at a wavelength of 193 nm due to inclusion of aromatic rings in the structure, a lithographic process by an ArF excimer laser, for example, using these resins cannot provide high accuracy corresponding to high photosensitivity, high resolution, and a high aspect ratio.

Therefore, a resin for use in a resist, transparent to a wavelength of 193 nm or less, particularly to a wavelength of 157 nm, and exhibiting excellent dry etching resistance equivalent to or better than aromatic rings has been desired. A polysiloxane is one such a polymer. R. R. Kunz at al. of the MIT have reported their research results showing excellent transparency of a polysiloxane at a wavelength of 193 nm or less, particularly at 157 nm, commenting on superiority of this polymer as a resist in a lithographic process using radiation with a wavelength of 193 nm or less (J. Photopolym. Sci. Technol., Vol. 12, No.4, 1999). Moreover, polysiloxanes are known to exhibit excellent dry etching properties. In particular, a resist containing polyorganosilsesquioxane having a ladder structure is known to possess high plasma resistance.

Several resist materials using a siloxane polymer have also been reported. For example, Japanese Patent Publication No. 323611/1993 discloses a radiation-sensitive resin composition comprising a polysiloxane having an acid-dissociable group such as a carboxylic acid group, phenol ether group, etc., on the side chain, bonded to a silicon atom via one or more carbon atoms. Japanese Patent Application Laid-open No. 160623/1996 discloses a positive tone resist using poly(2-carboxyethylsiloxane) in which the carboxyl group is protected with an acid-dissociable group such as a t-butyl group. Japanese Patent Application Laid-open No. 60733/1999 discloses a resist resin composition in which a polyorganosilsesquioxane providing an acid-decomposable ester group is used. However, resist materials using these conventional siloxane polymers containing an acid-dissociable group have not been satisfactory in producing basic properties in a resist such as transparency to radiation, resolution, developability, and the like.

Japanese Patent Publication No. 302382/1999 discloses a siloxane polymer having a non-aromatic monocyclic or polycyclic hydrocarbon group or a bridged cyclic hydrocarbon group containing a carboxyl group on the side chain, at least part of the carboxyl group being replaced by a group unstable to an acid, and a resist material containing such a polymer. This resist material exhibits small absorbance of a KrF excimer laser (wavelength: 248 nm) or an ArF excimer laser (wavelength: 193 nm), produces fine pattern configuration, and excels in properties such as sensitivity, resolution, dry etching resistance, etc. However, even if the above-mentioned siloxane polymer is considered, there are few siloxane polymer useful as a resin component of a resist material. A new siloxane polymer which can provide a resist material effectively sensing radiation with a short wavelength, exhibiting high transparency to radiation and superior anti-dryetching properties, and excelling in basic resist properties, and a silicon compound which can produce such a siloxane polymer are important subjects of development in view of the fast advance in microprocessing technologies for semiconductors.

Therefore, an object of the present invention is to provide a novel polysiloxane useful as a resin component for a resist material effectively sensing radiation with a short wavelength, typified by a KrF excimer laser (wavelength: 248 nm), and an ArF excimer laser (wavelength: 193 nm), and an F2 excimer laser (wavelength: 157 nm), exhibiting high transparency to radiation and superior dry etching properties, and excelling in basic resist properties required for resist materials such as high sensitivity, resolution, developability, etc.; a method of preparing such a polysiloxane; a silicon-containing alicyclic compound providing this polysiloxane; and a radiation-sensitive resin composition comprising this polysiloxane.

Therefore, an object of the present invention is to provide a novel polysiloxane useful as a resin component for a resist material effectively sensing radiation with a short wavelength, typified by a KrF excimer laser (wavelength: 248 nm), and an ArF excimer laser (wavelength: 193 nm), and an F2 excimer laser (wavelength: 157 nm), exhibiting high transparency to radiation and superior dry etching properties, and excelling in basic resist properties required for resist materials such as high sensitivity, resolution, developability, etc.; a method of preparing such a polysiloxane; a silicon-containing alicyclic compound providing this polysiloxane; and a radiation-sensitive resin composition comprising this polysiloxane.

SUMMARY OF THE INVENTION

The present invention provides a polysiloxane having the structural unit (I) and/or structural unit (II) and structural unit (III), shown in the following formula (1), and having a polystyrene-reduced weight average molecular weight determined by gel permeation chromatography (GPC) in the range of 500–1,000,000 (this polysiloxane is hereinafter referred to as "polysiloxane (1)"):

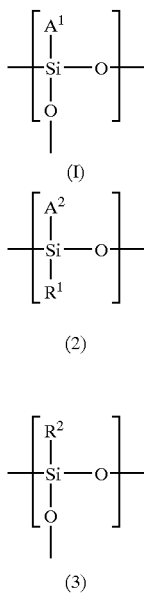

(1)

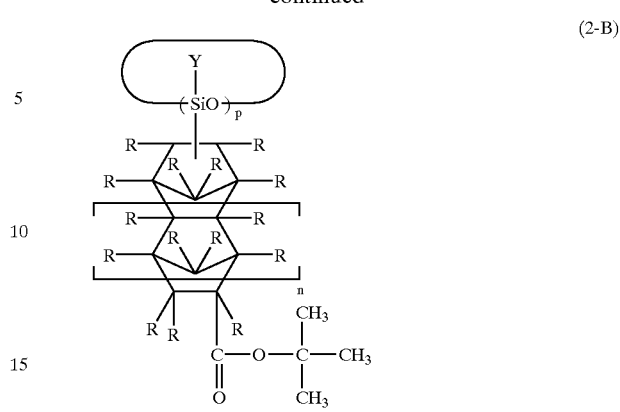

wherein $A^1$ and $A^2$ individually represent a monovalent organic group having an acid-dissociable group which dissociates by an action of an acid; $R^1$ represents a hydrogen atom, a monovalent hydrocarbon group having 1–20 carbon atoms, a monovalent halogenated hydrocarbon group having 1–20 carbon atoms, a halogen atom, or a primary, secondary, or tertiary amino group; and $R^2$ represents a monovalent hydrocarbon group having 1–20 carbon atoms, a monovalent halogenated hydrocarbon group having 1–20 carbon atoms, a halogen atom, or a primary, secondary, or tertiary amino group.

The present invention further provides a radiation-sensitive resin composition comprising: (a) a resin which comprises an alkali soluble or alkali low soluble polysiloxane copolymer, having the above structural unit (I) and/or structural unit (II) and structural unit (III), having a polystyrene-reduced weight average molecular weight determined by gel permeation chromatography (GPC) in the range of 500–1,000,000, and becoming soluble in alkali when an acid-dissociable group dissociates, and (b) a photoacid generator.

The present invention further provides a silicon-containing alicyclic compound represented by the following formula (2-A) or (2-B) (hereinafter referred to as "silicon-containing alicyclic compound (2)");

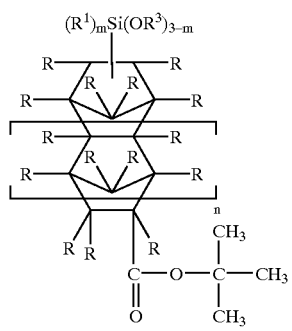

(2-A)

wherein R individually represents a hydrogen atom or a methyl group; $R^1$ individually represents a hydrogen atom, a monovalent hydrocarbon group having 1–20 carbon atoms, a monovalent halogenated hydrocarbon group having 1–20 carbon atoms, a halogen atom, or a primary, secondary, or tertiary amino group; and $R^3$ individually represents a monovalent hydrocarbon group having 1–20 carbon atoms, a monovalent halogenated hydrocarbon group having 1–20 carbon atoms, or the group of the following formula (i):

(i)

wherein X individually represents a hydrogen atom, a monovalent hydrocarbon group having 1–20 carbon atoms, a monovalent halogenated hydrocarbon group having 1–20 carbon atoms, or a linear, branched, or cyclic alkoxyl group having 1–20 carbon atoms, and a indicates an integer of 1–10, or, when m is 0 or 1, two $R^3$s may form a ring together with two oxygen atoms and the silicon atom; Y individually represents a hydrogen atom, a monovalent hydrocarbon group having 1–20 carbon atoms, a monovalent halogenated hydrocarbon group having 1–20 carbon atoms, a halogen atom, a primary, secondary, or tertiary amino group, or a group $=OR^3$ (wherein $R^3$ is the same as defined above); m is an integer of 0–3; p is an integer of 3–10; and n is an integer of 0–3; the silicon atom binding with the 2 or 3 position of the uppermost bicyclo[2.2.1]heptane ring.

The present invention further provides a polysiloxane having the structural unit (I-1) and/or structural unit (II-1), shown by the following formulas, and having a polystyrene-reduced weight average molecular weight determined by gel permeation chromatography (GPC) in the range of 500–1,000,000 (this polysiloxane is hereinafter referred to as "polysiloxane (3)"):

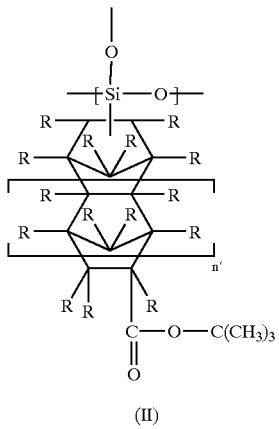

(II)

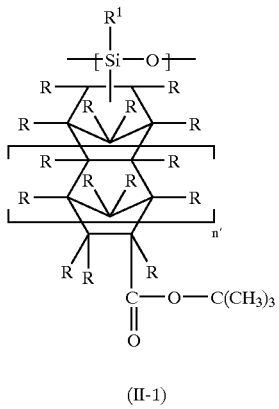

(II-1)

wherein R individually represents a hydrogen atom or a methyl group, $R^1$ represents a hydrogen atom, a monovalent hydrocarbon group having 1–20 carbon atoms, a monovalent halogenated hydrocarbon group having 1–20 carbon atoms, a halogen atom, or a primary, secondary, or tertiary amino group, and n' is an integer from 1–3, the silicon atom binding with the 2 or 3 position of the uppermost bicyclo[2.2.1]heptane ring.

The present invention further provides a silicon-containing alicyclic compound represented by the following formula (4-A) or (4-B) (hereinafter referred to as "silicon-containing alicyclic compound (4)"):

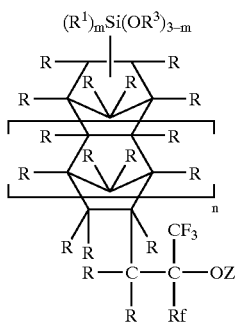

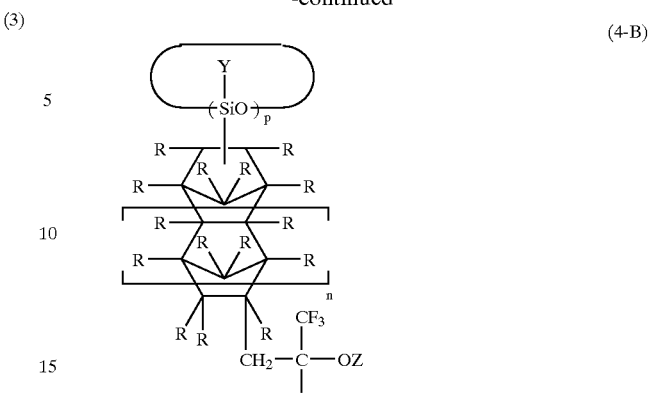

wherein R individually represents a hydrogen atom or a methyl group; $R^1$ individually represents a hydrogen atom, a monovalent hydrocarbon group having 1–20 carbon atoms, a monovalent halogenated hydrocarbon group having 1–20 carbon atoms, a halogen atom, or a primary, secondary, or tertiary amino group; $R^3$ individually represents a monovalent hydrocarbon group having 1–20 carbon atoms, a monovalent halogenated hydrocarbon group having 1–20 carbon atoms, or the group of the following formula (i):

wherein X individually represents a hydrogen atom, a monovalent hydrocarbon group having 1–20 carbon atoms, a monovalent halogenated hydrocarbon group having 1–20 carbon atoms, or a linear, branched, or cyclic alkoxyl group having 1–20 carbon atoms, and a indicates an integer of 1–10, or, when m is 0 or 1, two $R^3$s may form a ring together with two oxygen atoms and the silicon atom; Y individually represents a hydrogen atom, a monovalent hydrocarbon group having 1–20 carbon atoms, a monovalent halogenated hydrocarbon group having 1–20 carbon atoms, a halogen atom, a primary, secondary, or tertiary amino group, or a group =$OR^3$ (wherein $R^3$ is the same as defined above); m is an integer of 0–3; p is an integer of 3–10; and n is an integer of 0–3; the silicon atom binding with the 2 or 3 position of the uppermost bicyclo[2.2.1]heptane ring.

The present invention further provides a polysiloxane having the structural unit (I-2) and/or structural unit (II-2), shown by the following formulas, and having a polystyrene-reduced weight average molecular weight determined by gel permeation chromatography (GPC) in the range of 500–1,000,000 (this polysiloxane is hereinafter referred to as "polysiloxane (5)"):

(3)

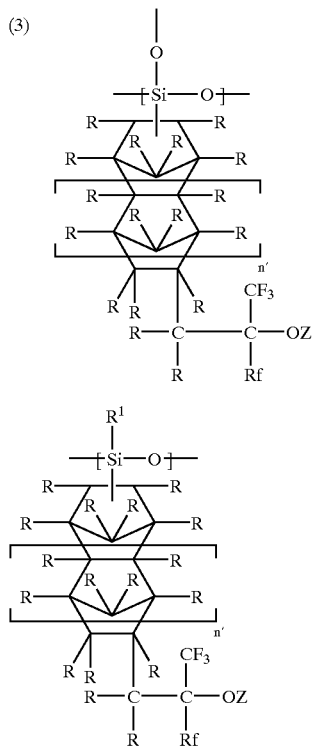

(I-2)

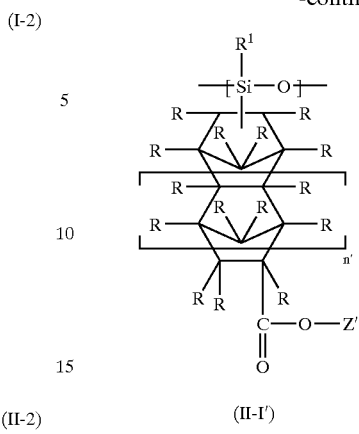

(II-2)

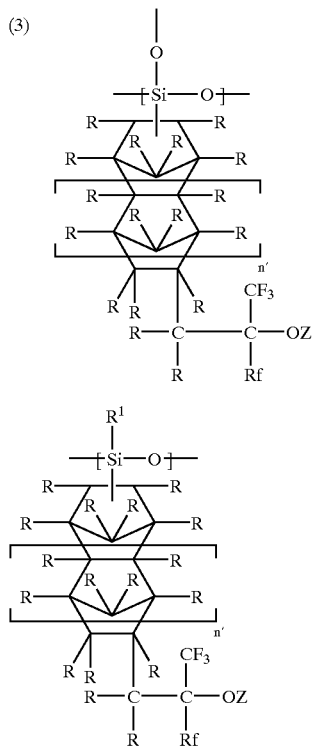

wherein R individually represent a hydrogen atom or a methyl group, $R^1$ represents a hydrogen atom, a monovalent hydrocarbon group having 1–20 carbon atoms, a monovalent halogenated hydrocarbon group having 1–20 carbon atoms, a halogen atom, or a primary, secondary, or tertiary amino group, Rf represents a hydrogen atom, methyl group, or trifluoromethyl group, Z represents a hydrogen atom or a monovalent organic group dissociating hydrogen atoms with an action of an acid, and n is an integer of 0–3, the silicon atom binding with the 2 or 3 position of the uppermost bicyclo[2.2.1]heptane ring.

The present invention further provides a radiation-sensitive resin composition comprising:

(a) an alkali soluble or alkali low soluble polysiloxane comprising at least one structural unit selected from the structural unit (I-1') and the structural unit (II-1'), shown by the following formulas:

(3')

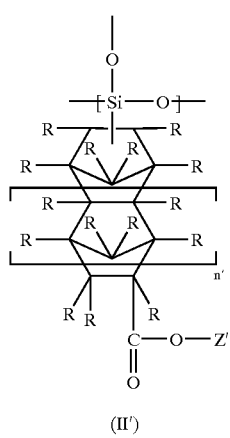

(II')

(II-I')

wherein R individually represents a hydrogen atom or a methyl group, $R^1$ represents a hydrogen atom, a monovalent hydrocarbon group having 1–20 carbon atoms, a monovalent halogenated hydrocarbon group having 1–20 carbon atoms, a halogen atom, or a primary, secondary, or tertiary amino group, Z' represents a monovalent organic group dissociating by the action of acid to produce hydrogen atoms, and n' is an integer from 1–3, the silicon atom binding with the 2 or 3 position of the uppermost bicyclo[2.2.1] heptane ring; and having a polystyrene-reduced weight average molecular weight determined by gel permeation chromatography (GPC) in the range of 500–1,000,000 (hereinafter referred to as "Polysiloxane (3')"), and an alkali soluble or alkali low soluble polysiloxane comprising at least one structural unit selected from the structural unit (1–2) and the structural unit (11–2), shown above, and having a polystyrene-reduced weight average molecular weight determined by gel permeation chromatography (GPC) in the range of 500–1,000,000, the resin becoming soluble in alkali when the acid-dissociable group dissociates; and (b) a photoacid generator.

The present invention further provides a method of preparing a polysiloxane having the structural unit (I) and/or structural unit (II) and structural unit (III), shown above, and having a polystyrene-reduced weight average molecular weight determined by gel permeation chromatography (GPC) in the range of 500–1,000,000, the method comprising a step of polycondensing at least one component selected from the group consisting of a compound shown by the following formula (6) or a linear of cyclic oligomer prepared by partial condensation of this compound and/or at least one component selected from the group consisting of a compound shown by the following formula (7) or a linear of cyclic oligomer prepared by partial condensation of this compound, and at least one component selected from the group consisting of a compound shown by the following formula (8) or a linear of cyclic oligomer prepared by partial condensation of this compound in the presence of an acidic catalyst:

(6)

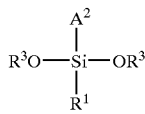
(7)

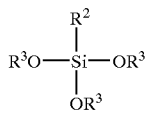
(8)

wherein $A^1$ and $A^2$ individually represent a monovalent organic group having an acid-dissociable group which dissociates by an action of an acid, $R^1$ represents a hydrogen atom, a monovalent hydrocarbon group having 1–20 carbon atoms, a monovalent halogenated hydrocarbon group having 1–20 carbon atoms, a halogen atom, or a primary, secondary, or tertiary amino group, $R^2$ represents a monovalent hydrocarbon group having 1–20 carbon atoms, a monovalent halogenated hydrocarbon group having 1–20 carbon atoms, a halogen atom, or a primary, secondary, or tertiary amino group, and $R^3$ individually represents a monovalent hydrocarbon group having 1–20 carbon atoms, a monovalent halogenated hydrocarbon group having 1–20 carbon atoms, or the group of the following formula (i):

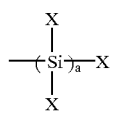
(i)

wherein X individually represents a hydrogen atom, a monovalent hydrocarbon group having 1–20 carbon atoms, a monovalent halogenated hydrocarbon group having 1–20 carbon atoms, or a linear, branched, or cyclic alkoxyl group having 1–20 carbon atoms, and a indicates an integer of 1–10.

The present invention further provides a method of preparing a polysiloxane having the structural unit (I-1) and/or structural unit (II-1), shown above, and having a polystyrene-reduced weight average molecular weight determined by gel permeation chromatography (GPC) in the range of 500–1,000,000, the method comprising a step of polycondensing at least one component selected from the group consisting of the silicon-containing alicyclic compounds having the above-described formulas (2-A) or (2-B) or a linear or cyclic oligomer prepared by partial condensation of this silicon-containing alicyclic compound in the presence of an acidic catalyst.

The present invention further provides a method of preparing a polysiloxane having the structural unit (I-2) and/or structural unit (II-2), shown above, and having a polystyrene-reduced weight average molecular weight determined by gel permeation chromatography (GPC) in the range of 500–1,000,000, the method comprising a step of polycondensing at least one component selected from the group consisting of the silicon-containing alicyclic compounds having the above-described formulas (4-A) or (4-B) or a linear or cyclic oligomer prepared by partial condensation of this silicon-containing alicyclic compound in the presence of an acidic catalyst.

Other objects, features and advantages of the invention will hereinafter become more readily apparent from the following description.

DETAILED DESCRIPTION OF THE INVENTION AND PREFERRED EMBODIMENTS

The present invention will be described in more detail below.

Polysiloxane (1)

Polysiloxane (1) has the structural unit (I) and/or structural unit (II) and structural unit (III), each having a formula shown above.

As the monovalent organic group having an acid-dissociable group dissociable by the action of an acid, represented by $A^1$ and $A^2$ in the structural unit (I) and/or structural unit (II), groups which dissociate in the presence of an acid to produce a carboxyl group, phenolic hydroxyl group, or alcoholic hydroxyl group, and are stable under the reaction conditions for preparing the polysiloxane (1) can be given. As preferable specific examples, the groups shown by the following formula (9) (hereinafter referred to as "an acid-dissociable group (α)"), the following formula (10) (hereinafter referred to as "an acid-dissociable group (β)"), the following formula (11) (hereinafter referred to as "an acid-dissociable group (γ)"), and the like can be given.

(9)

wherein p indicates a single bond, methylene group, difluoromethylene group, alkylene group having 2–20 carbon atoms, fluoroalkylene group having 2–20 carbon atoms, divalent aromatic group having 6–20 carbon atoms, or divalent alicyclic group having 3–20 carbon atoms, Q represents a group —O— or —COO—, and Z' represents a monovalent organic group dissociating by the action of acid to produce hydrogen atoms.

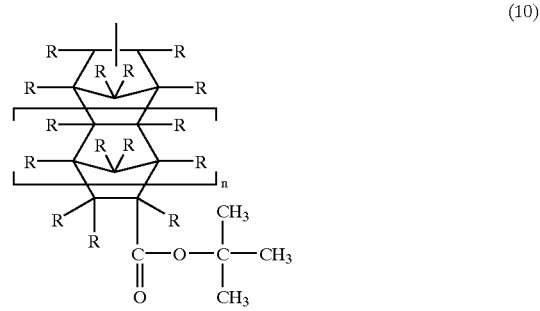
(10)

wherein R individually represents a hydrogen atom or a methyl group and n is integer of 0–3, the free bonding hands binding with the 2 or 3 position of the uppermost bicyclo [2.2.1]heptane ring.

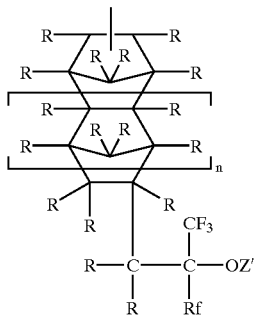

(11)

wherein R individually represents a hydrogen atom or a methyl group, Rf represents a hydrogen atom, methyl group, or trifluoromethyl group, V represents a monovalent organic group dissociating by the action of acid to produce hydrogen atoms, and n is an integer of 0–3, the free bonding hands binding with the 2 or 3 position of the uppermost bicyclo [2.2.1]heptane ring.

As examples of the alkylene group having 2–20 carbon atoms represented by P in the acid-dissociable group ($\alpha$), ethylene group, n-propylene group, i-propylene group, n-butylene group, and the like can be given.

As examples of the fluoroalkylene group having 2–20 carbon atoms represented by P, a tetrafluoroethylene group, hexafluoro-n-propylene group, octafluoro-n-butylene group, and the like can be given.

As examples of the divalent aromatic group having 6–20 carbon atoms represented by P, a phenylene group, naphthylene group, perfluorophenylene group, perfluoronaphthylene group, and the like can be given.

As examples of the divalent alicyclic group having 3–20 carbon atoms represented by P, a divalent hydrocarbon group having a norbornene skeleton, tricyclodecane skeleton, or adamantane skeleton and a halide of such a hydrocarbon group can be given.

As the group P in the acid-dissociable group ($\alpha$), a single bond, methylene group, difluoromethylene group, a divalent hydrocarbon group having a norbornene skeleton, its halide derivative, a divalent hydrocarbon group having an adamantine skeleton, its halide derivative, and the like are preferable.

As examples of the monovalent organic group dissociating a hydrogen atom by the action of an acid represented by Z' in the acid-dissociable group ($\alpha$) and acid-dissociable group ($\gamma$), a tertiary alkyl group, a group forming an acetal group together with the oxygen atom with which the group Z' binds (hereinafter referred to as an "acetal-forming group"), a substituted methyl group, 1-substituted ethyl group, 1-branched alkyl group (excluding tertiary alkyl groups), silyl group, germyl group, alkoxycarbonyl group, acyl group, cyclic acid-dissociable group, and the like can be given.

As examples of the tertiary alkyl group, a t-butyl group, 1,1-dimethylpropyl group, 1-methyl-1-ethylpropyl group, 1,1-dimethylbutyl group, 1-methyl-1-ethylbutyl group, 1,1-dimethylpentyl group, 1-methyl-1-ethylpentyl group, 1,1-dimethylhexyl group, 1,1-dimethylheptyl group, 1,1-dimethyloctyl group, and the like can be given.

As examples of the acetal-forming group, a methoxymethyl group, ethoxymethyl group, n-propoxymethyl group, i-propoxymethyl group, n-butoxymethyl group, t-butoxymethyl group, n-pentyloxymethyl group, n-hexyloxymethyl group, cyclopentyloxymethyl group, cyclohexyloxymethyl group, 1-methoxyethyl group, 1-ethoxyethyl group, 1-n-propoxyethyl group, 1-i-propoxyethyl group, 1-n-butoxyethyl group, 1-t-butoxyethyl group, 1-n-pentyloxyethyl group, 1-n-hexyloxyethyl group, 1-cyclopentyloxyethyl group, 1-cyclohexyloxyethyl group, 1-methoxypropyl group, 1-ethoxypropyl group, (cyclohexyl)(methoxy)methyl group, (cyclohexyl)(ethoxy)methyl group, (cyclohexyl)(n-propoxy)methyl group, (cyclohexyl)(i-propoxy)methyl group, (cyclohexyl)(cyclohexyloxy)methyl group, and the like can be given.

As examples of the substituted methyl group, a phenacyl group, p-bromophenacyl group, p-methoxyphenacyl group, p-methylthiophenacyl group, $\alpha$-methylphenacyl group, cyclopropylmethyl group, benzyl group, diphenylmethyl group, triphenylmethyl group, p-bromobenzyl group, p-nitrobenzyl group, p-methoxybenzyl group, p-methylthiobenzyl group, p-ethoxybenzyl group, p-ethylthiobenzyl group, piperonyl group, methoxycarbonylmethyl group, ethoxycarbonylmethyl group, n-propoxycarbonylmethyl group, i-propoxycarbonylmethyl group, n-butoxycarbonylmethyl group, t-butoxycarbonylmethyl group, and the like can be given.

As examples of the 1-substituted ethyl group, a 1-cyclopropylethyl group, 1-phenylethyl group, 1,1-diphenylethyl group, 1-methoxycarbonylethyl group, 1-ethoxycarbonylethyl group, 1-n-propoxycarbonylethyl group, 1-i-propoxycarbonylethyl group, 1-n-butoxycarbonylethyl group, 1-t-butoxycarbonylethyl group, and the like can be given.

As examples of the 1-branched alkyl group, i-propyl group, sec-butyl group, 1-methylbutyl group, and the like can be given.

As examples of the silyl group, a trimethylsilyl group, ethyldimethylsilyl group, methyldiethylsilyl group, triethylsilyl group, i-propyldimethylsilyl group, methyldi-i-propylsilyl group, tri-i-propylsilyl group, t-butyldimethylsilyl group, methyldi-t-butylsilyl group, tri-t-butylsilyl group, phenyldimethylsilyl group, methyldiphenylsilyl group, triphenylsilyl group, and the like can be given.

As examples of the germyl group, a trimethylgermyl group, ethyldimethylgermyl group, methyldiethylgermyl group, triethylgermyl group, i-propyldimethylgermyl group, methyldi-i-propylgermyl group, tri-i-propylgermyl group, t-butyldimethylgermyl group, methyldi-t-butylgermyl group, tri-t-butylgermyl group, phenyldimethylgermyl group, methyldiphenylgermyl group, triphenylgermyl group, and the like can be given.

As examples of the alkoxycarbonyl group, a methoxycarbonyl group, ethoxycarbonyl group, i-propoxycarbonyl group, t-butoxycarbonyl group, and the like can be given.

As examples of the acyl group, an acetyl group, propionyl group, butyryl group, heptanoyl group, hexanoyl group, valeryl group, pivaloyl group, isovaleryl group, lauryloyl group, myristoyl group, palmitoyl group, stearoyl group, oxalyl group, malonyl group, scucinyl group, glutaryl group, adipoyl group, piperoyl group, suberoyl group, azelaoyl group, sebacoyl group, acryloyl group, propioloyl group, methacryloyl group, crotonoyl group, oleoyl group, maleoyl group, fumaroyl group, mesaconoyl group, campholoyl group, benzoyl group, phthaloyl group, isophthaloyl group, terephthaloyl group, naphthoyl group, toluoyl group, hydroatropoyl group, atropoyl group, cinnamoyl group, furoyl group, thenoyl group, nicotinoyl group, isonicotinoyl group, p-toluenesulfonyl group, mesyl group, and the like can be given.

As examples of the cyclic acid-dissociable group, an 3-oxocyclohexyl group, tetrahydropyranyl group, tetrahydrofuranyl group, tetrahydrothiopyranyl group, tetrahydrothiofuranyl group, 3-bromotetrahydropyranyl group, 4-methoxytetrahydropyranyl group, 2-oxo-4-methyl-4-tetrahydropyranyl group, 4-methoxytetrahydrothiopyranyl group, 3-tetrahydrothiophene-1,1-dioxide group, and the like can be given.

As the monovalent organic group dissociating a hydrogen atom by the action of an acid represented by Z' in the acid-dissociable group (α) and acid-dissociable group (γ), a t-butyl group, t-butoxycarbonyl group, tetrahydropyranyl group, tetrahydrofuranyl group, methoxymethyl group, ethoxymethyl group, 1-methoxyethyl group, 1-ethoxyethyl group, t-butyldimethylsilyl group, and the like are preferable.

As the group R in the acid-dissociable group (β) and acid-dissociable group (γ), both the hydrogen atom and methyl group are preferable. n is preferably 0 or 1.

As the group Rf in the acid-dissociable group (γ), any of the hydrogen atom, methyl group, and trifluoromethyl group are preferable.

In polysiloxane (1), an acid-dissociable group (β) is particularly preferable as the group $A^1$, with an acid-dissociable group (β) in which n is 1–3 being ideal. As the group $A^2$, an acid-dissociable group (γ) is particularly preferable.

In the group $R^1$ in the structural unit (II) and the group $R^2$ in the structural unit (III), given as examples of the monovalent hydrocarbon groups having 1–20 carbon atoms are a linear or branched alkyl groups such as a methyl group, ethyl group, n-propyl group, i-propyl group, n-butyl group, 2-methylpropyl group, 1-methylpropyl group, t-butyl group, n-pentyl group, neopentyl group, n-hexyl group, n-heptyl group, n-octyl group, 2-ethylhexyl group, n-nonyl group, n-decyl group, n-dodecyl group, n-tetradecyl group, n-hexadecyl group, n-octadecyl group, n-eicosyl group, and the like; cycloalkyl groups such as a cyclobutyl group, cyclopentyl group, cyclohexyl group, and the like; aromatic hydrocarbon group such as a phenyl group, o-tolyl group, m-tolyl group, p-tolyl group, benzyl group, phenethyl group, 1-naphthyl group, 2-naphthyl group, and the like; and bridged hydrocarbon groups such as norbornyl group, tricyclodecanyl group, tetracyclodecanyl group, adamantyl group, and the like.

Of these monovalent hydrocarbon groups, a methyl group and ethyl group are preferable.

As examples of the monovalent halogenated hydrocarbon group having 1–20 carbon atoms, a monovalent hydrocarbon group having 1–20 carbon atoms in which one or more hydrogen atoms are replaced by one or more halogen atoms, preferably a fluorine atom, can be given. Specific examples include a trifluoromethyl group, pentafluoroethyl group, 3,3,3,2,2-pentafluoro-n-propyl group, perfluoro-n-propyl group, perfluoro-i-propyl group, and the group shown by the following formula (ii):

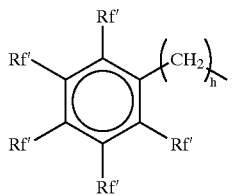

(ii)

wherein Rf' individually represents a hydrogen atoms or fluorine atom, with at least one of the Rf's being a fluorine atom, and b is an integer of 0–4, 2-(pentafluorophenyl) hexafluoro-n-propyl group, 3-(pentafluorophenyl) hexafluoro-n-propyl group, perfluoronorbornyl group, and the like can be given.

Among these monovalent halogenated hydrocarbon groups, a trifluoromethyl group, a pentafluoroethyl group, a group of the formula (ii) in which 5 Rf's are fluorine atoms and b is 0, a group of the formula (ii) in which 5 Rf's are fluorine atoms and b is 1, a group of the formula (ii) in which 5 Rf's are fluorine atoms and b is 2,3-(pentafluorophenyl) hexafluoro-n-propyl group, and the like are preferable.

As examples of halogen atoms, a fluorine atom, chlorine atom, and bromine atom can be given, with a chlorine atom being particularly preferable.

Given as examples of secondary or tertiary amino groups are methylamino group, ethylamino group, n-propylamino group, i-propylamino group, n-butylamino group, cyclopentylamino group, cyclohexylamino group, phenylamino group, benzylamino group, dimethylamino group, diethylamino group, di-i-propylamino group, dicyclopentylamino group, dicyclohexylamino group, diphenylamino group, dibenzylamino group, and the like.

As the amino groups for $R^1$ and $R^2$, an amino group, dimethylamino group, diethylamino group, dicyclopentylamino group, dicyclohexylamino group, diphenylamino group, and the like are preferable.

As $R^1$ in the structural unit (II) and $R^2$ in the structural unit (III), a methyl group, ethyl group, cyclohexyl group, trifluoromethyl group, pentafluoroethyl group, perfluorophenethyl group, 3-(pentafluorophenyl)hexafluoro-n-propyl group, chlorine atom, dimethylamino group, and the like are preferable.

The structural unit (I), structural unit (II), and structural unit (III) maybe used in the polysiloxane (1) either individually or in combination of two or more.

The specific content of these structural units in the polysiloxane (1) may vary according to the types and combinations of the structural units, the application of the polysiloxane (1), and the like. A preferable specific content of each unit may be suitably determined by experiments and the like. The amount of the structural unit (I) is usually 1–95 mol %, preferably 5–80 mol %, and particularly preferably 10–60 mol % of the total amount of the structural units. The amount of the structural unit (II) is usually 95 mol % or less, preferably 0–50 mol %, and particularly preferably 0–30 mol % of the total amount of the structural units. The amount of the structural unit (III) is usually 5–95 mol %, preferably 20–95 mol %, and particularly preferably 40–90 mol % of the total amount of the structural units. The total of the structural unit (I) and the structural unit (II) is usually 1–95 mol %, preferably 5–80 mol %, and particularly preferably 10–60 mol % of the total amount of the structural units.

If the amount of the structural unit (I) is less than 1 mol %, resolution of the radiation-sensitive resin composition tends to decrease. If the amount exceeds 95 mol %, transparency tends to decrease. If the amount of the structural unit (II) is more than 95 mol %, the glass transition temperature and transparency of the resulting polymer tends to decrease. If the amount of the recurring unit (III) is less than 5 mol, transparency tends to decrease. If the amount exceeds 95 mol %, on the other hand, resolution of the radiation-sensitive resin composition tends to decrease. If the total amount of the structural unit (I) and the structural unit (II) is less than 1 mol %, solubility of the resulting resin composition in an alkaline developer tends to decrease. If the amount exceeds 95 mol %, solubility of the resulting resin composition in an alkaline developer tends to increase.

In either case, it may become difficult for the resulting radiation-sensitive resin composition to form a highly accurate resist pattern shape.

The amount of the structural units other than structural units (I)–(III) is usually 90 mol % or less, and preferably 95 mol % or less of the total amount of all structural units.

The total amount of bi-functional structural units in the polycondensation reaction is usually 0–100 mol %, and preferably 1–100 mol %. The total amount of tri-functional structural units in the polycondensation reaction is usually 1–100 mol %, and preferably 2–100 mol %. The total amount of tetra-functional structural units in the polycondensation reaction is usually 90 mol % or less, and preferably 50 mol % or less.

Usually, polysiloxane (1) has a ladder structure as part of the molecular structure. The ladder structure is principally introduced by a raw material having tri- or greater functional structure with respect to the polycondensation reaction.

A typical ladder structure in polysiloxane (1) has a structural unit in which two or more of the recurring units (IV) to (VI) shown in the following formula (12) are combined together.

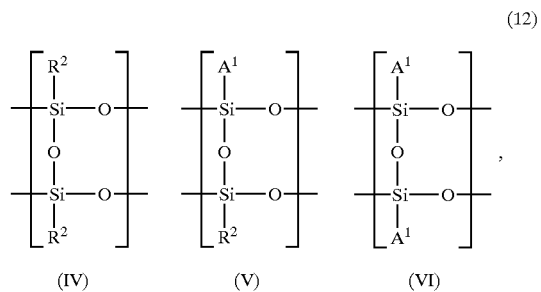

(12)

wherein $A^1$ and $R^2$ are the same as previously defined in the above formula (1).

The polystyrene-reduced weight average molecular weight (hereinafter referred to as "Mw") of the polysiloxane (1) determined by gel permeation chromatography (GPC) is 500–1,000,000, preferably 500–500,000, and particularly preferably 1,000–100,000. If the Mw is less than 500, the glass transition temperature of the resulting polymer tends to decrease. If the Mw exceeds 1,000,000, on the other hand, solubility of the resulting polymer in solvents tends to decrease.

The glass transition temperature (Tg) of polysiloxane (1) is usually from −50 to 500° C., and preferably from 0 to 300° C. If the glass transition temperature (Tg) of polysiloxane (1) is less than −50° C., pattern formation using the resulting radiation-sensitive resin composition tends to be difficult. If more than 500° C., solubility of the polymer in solvents tends to decrease.

Polysiloxane (1) is usually insoluble or scarcely soluble in alkali, but becomes alkali-soluble when the acid-dissociable group dissociates. Thus, the polymer is particularly useful as an acid-dissociable group-containing resin component in radiation-sensitive resin compositions for microprocessing using various types of radiation such as deep ultraviolet radiation, electron beams, and X-rays.

Polysiloxane (1) is also useful as a material for fabricating formed articles and films, and as laminating materials, components for coating compositions, and the like.

Silicon-containing alicyclic compound (2)

In the silicon-containing alicyclic compound (2), as examples of the monovalent hydrocarbon group having 1–20 carbon atoms, monovalent halogenated hydrocarbon group having 1–20 carbon atoms, halogen atom, or primary, secondary, or tertiary amino group represented by $R^1$, the corresponding groups previously mentioned in connection with the group $R^1$ in the structural unit (II) of the polysiloxane (1) can be given.

A methyl group, ethyl group, cyclopentyl group, cyclohexyl group, norbornyl group, tetracyclodecanyl group, and the like can be given as preferable monovalent hydrocarbon groups having 1–20 carbon atoms represented by $R^1$. Given as examples of preferable monovalent halogenated hydrocarbon groups having 1–20 carbon atoms represented by $R^1$ are a trifluoromethyl group, pentafluoroethyl group, 3,3,3,2,2-pentafluoro-n-propyl group, pentafluorophenyl group, o-fluorophenyl group, m-fluorophenyl group, p-fluorophenyl group, 2,3-difluorophenyl group, 2,4-difluorophenyl group, 2,5-difluoro phenyl group, 2,6-difluorophenyl group, 3,4-difluoro phenyl group, 3,5-difluorophenyl group, 2,3,4-trifluorophenyl group, 2,3,5-trifluorophenyl group, 2,3,6-trifluorophenyl group, 2,4,6-trifluorophenyl group, 3,4,5-trifluorophenyl group, a group of the formula (ii) in which 5 Rf's are fluorine atoms and b is 1, a group of the formula (ii) in which 5 Rf's are fluorine atoms and b is 2, and the like. A chlorine atom is preferable as a halogen atom represented by $R^1$, and an amino group, dimethylamino group, diethylamino group, dicyclopentylamino group, dicyclohexylamino group, diphenylamino group, and the like are preferable as amino groups represented by $R^1$.

Particularly preferable groups represented by $R^1$ in the silicon-containing alicyclic compound (2) are a methyl group, ethyl group, cyclohexyl group, phenyl group, pentafluorophenyl group, chlorine atom, dimethylamino group, and the like.

As examples of the monovalent hydrocarbon group having 1–20 carbon atoms and monovalent halogenated hydrocarbon group having 1–20 carbon atoms represented by $R^3$, the corresponding groups previously mentioned in connection with the group $R^1$ in the structural unit (II) of the polysiloxane (1) can be given.

A methyl group, ethyl group, n-propyl group, i-propyl group, and the like can be given as preferable monovalent hydrocarbon groups having 1–20 carbon atoms represented by $R^3$. Given as examples of preferable monovalent halogenated hydrocarbon groups having 1–20 carbon atoms represented by $R^3$ are a trifluoromethyl group, pentafluoroethyl group, 3,3,3,2,2-pentafluoro-n-propyl group, pentafluorophenyl group, o-fluorophenyl group, m-fluorophenyl group, p-fluorophenyl group, 2,3-difluorophenyl group, 2,4-difluorophenyl group, 2,5-difluoro phenyl group, 2,6-difluorophenyl group, 3,4-difluoro phenyl group, 3,5-difluorophenyl group, 2,3,4-trifluorophenyl group, 2,3,5-trifluorophenyl group, 2,3,6-trifluorophenyl group, 2,4,6-trifluorophenyl group, 3,4,5-trifluorophenyl group, a group of the formula (ii) in which 5 Rf's are fluorine atoms and b is 1, a group of the formula (ii) in which 5 Rf's are fluorine atoms and b is 2, and the like.

As examples of the monovalent hydrocarbon group having 1–20 carbon atoms and monovalent halogenated hydrocarbon group having 1–20 carbon atoms represented by X in the formula (i), which shows an example of the group $R^3$, the corresponding groups previously mentioned in connection with the group $R^1$ in the structural unit (II) of the polysiloxane (1) can be given.

As examples of the linear, branched, or cyclic alkoxyl groups having 1–20 carbon atoms represented by X, a methoxy group, ethoxy group, n-propoxy group, i-propoxy group, i-butoxy group, sec-butoxy group, t-butoxy group, cyclopentyloxy group, cyclohexyloxy group, and the like can be given.

Particularly preferable groups for the group X in the formula (i) are a methyl group, phenyl group, methoxy group, and the like. a in the formula (i) is preferably 1–5.

As examples of the hydrocarbon group having 1–20 carbon atoms, halogenated hydrocarbon group having 1–20 carbon atoms, halogen atom, or primary, secondary, or tertiary amino group represented by Y, the corresponding groups previously mentioned in connection with the group $R^1$ in the structural unit (II) of the polysiloxane (1) can be given.

Particularly preferable groups represented by $R^3$ in the silicon-containing alicyclic compound (2) are a methyl group, ethyl group, t-butyl group, trimethylsilyl group, and the like.

As the group R in the silicon-containing alicyclic compound (2), both the hydrogen atom and methyl group are preferable. A preferable integer for m and n is 0 or 1.

The compounds shown by the following formulas (2-1) to (2-92) (wherein Me indicates a methyl group) can be given as preferable examples of the silicon-containing alicyclic compound (2):

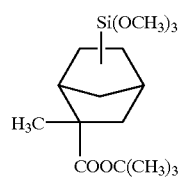 (2-15)
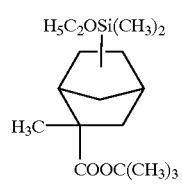 (2-16)
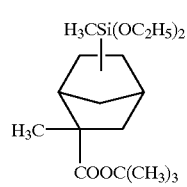 (2-17)
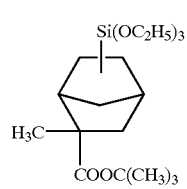 (2-18)
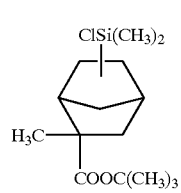 (2-19)
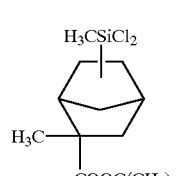 (2-20)
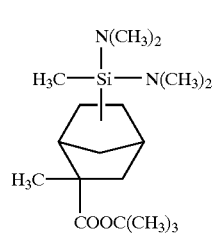 (2-21)
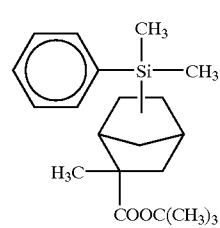 (2-22)
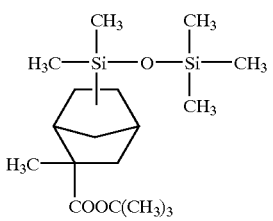 (2-23)
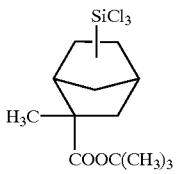 (2-24)
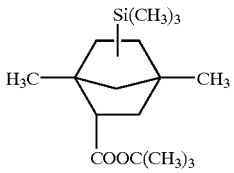 (2-25)
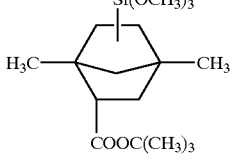 (2-26)
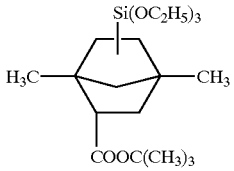 (2-27)
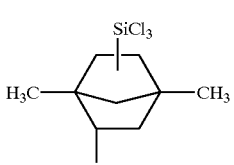 (2-28)
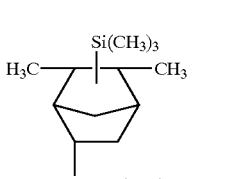 (2-29)
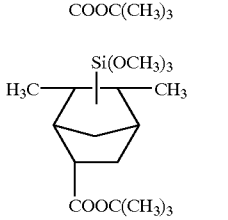 (2-30)

(2-31) 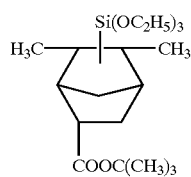
(2-32) 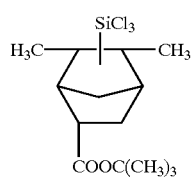
(2-33) 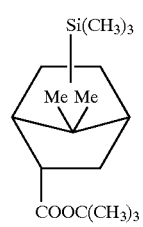
(2-34) 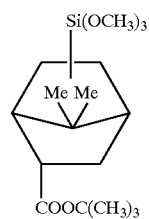
(2-35) 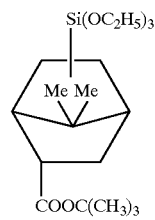
(2-36) 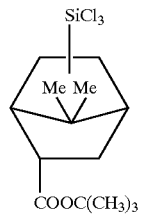
(2-37) 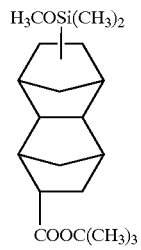
(2-38) 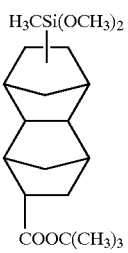
(2-39) 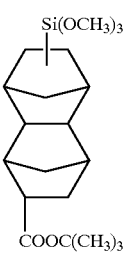
(2-40) 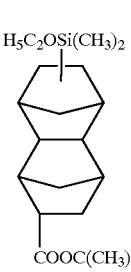
(2-41) 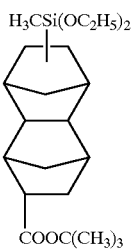
(2-42) 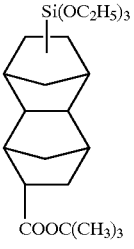
(2-43) 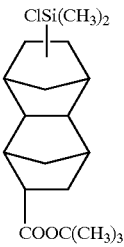

-continued
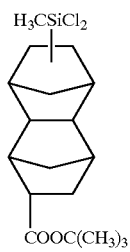
(2-44)
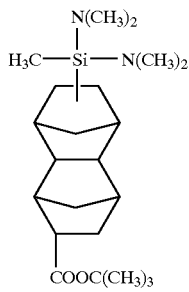
(2-45)
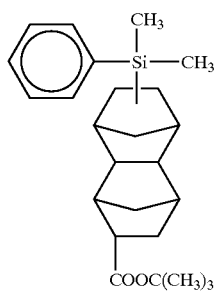
(2-46)
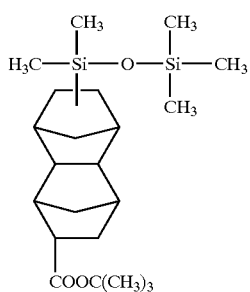
(2-47)
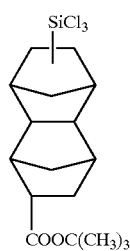
(2-48)
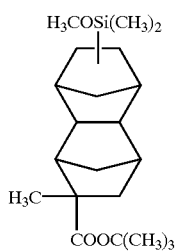
(2-49)
-continued
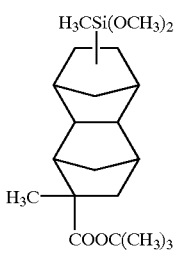
(2-50)
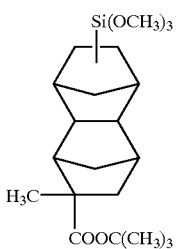
(2-51)
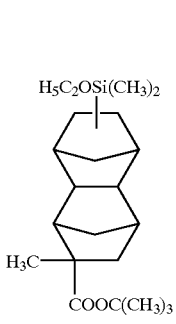
(2-52)
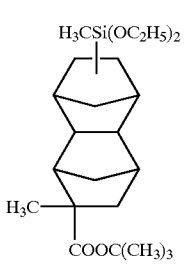
(2-53)
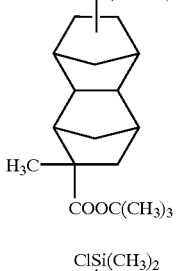
(2-54)
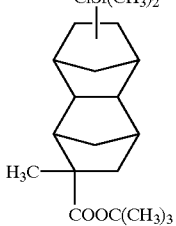
(2-55)

(2-56)
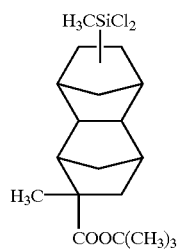
(2-57)
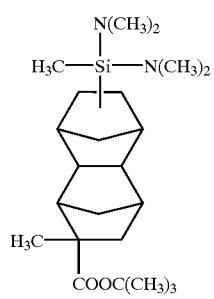
(2-58)
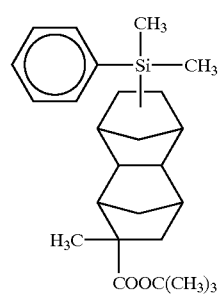
(2-59)
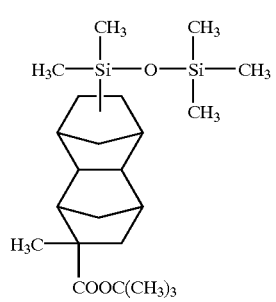
(2-60)
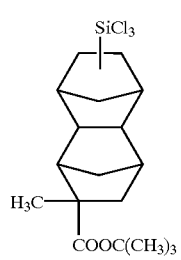
(2-61)
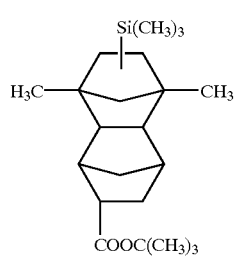
(2-62)
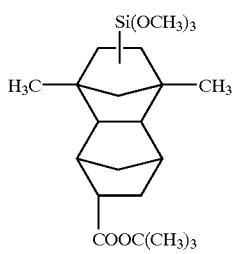
(2-63)
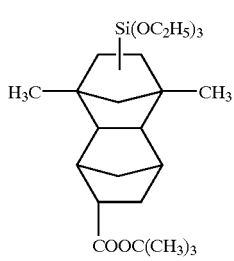
(2-64)
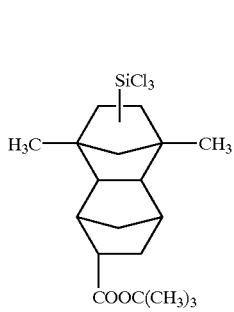
(2-65)
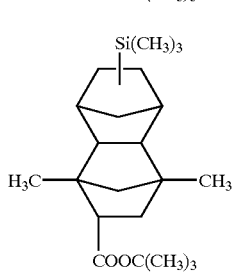
(2-66)
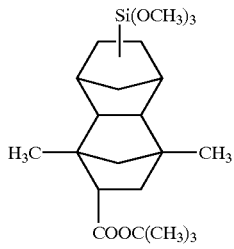
(2-67)
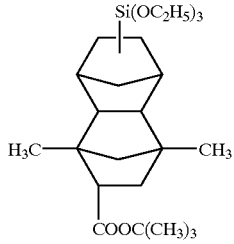

(2-68) 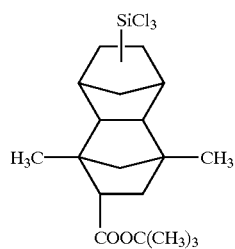
(2-69) 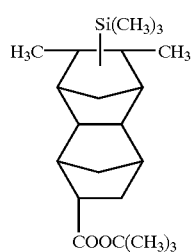
(2-70) 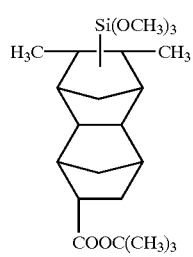
(2-71) 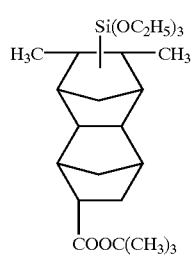
(2-72) 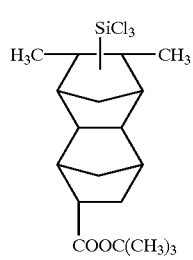
(2-73) 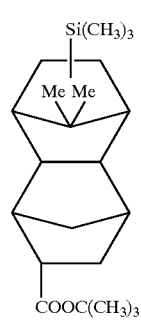
(2-74) 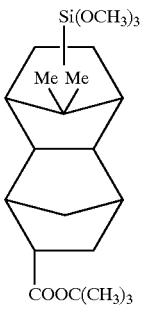
(2-75) 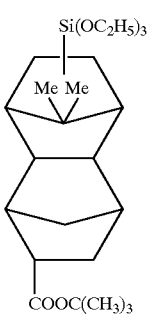
(2-76) 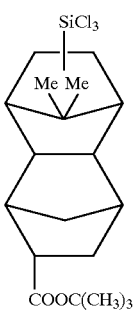
(2-77) 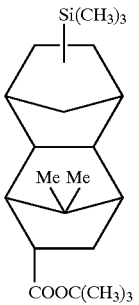
(2-78) 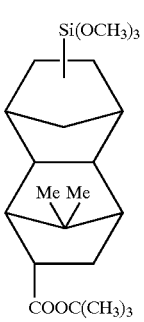

(2-79) 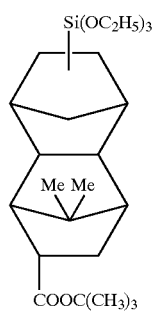
(2-80) 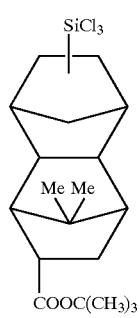
(2-81) 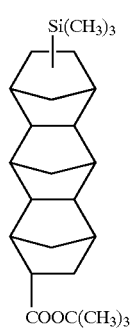
(2-82) 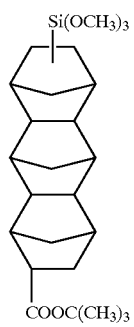
(2-83) 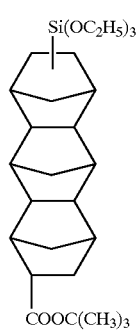
(2-84) 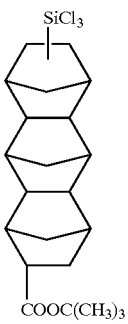
(2-85) 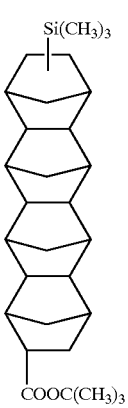
(2-86) 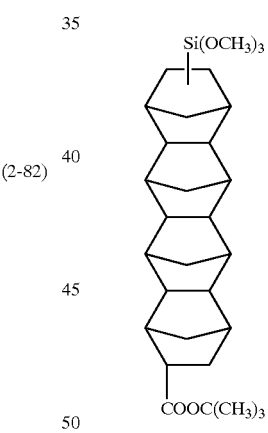
(2-87) 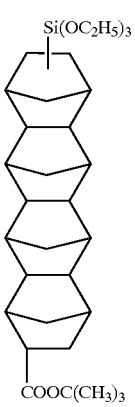

-continued (2-88)

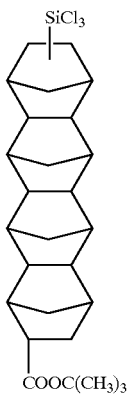

(2-89)

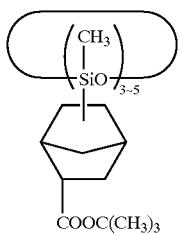

(2-90)

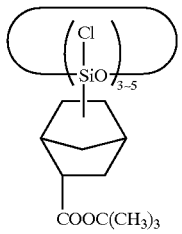

(2-91)

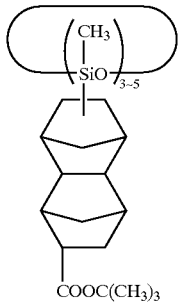

(2-92)

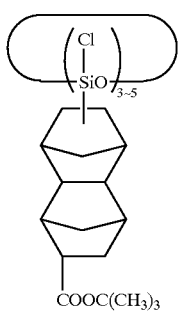

Of the above silicon-containing alicyclic compound (2), compounds shown by the formulas (2-2), (2-3), (2-5), (2-6), (2-8), (2-9), (2-10), (2-11), and (2-12) are particularly preferable.

The silicon-containing alicyclic compound (2) of the above formula (2-A) is very useful as a raw material for producing the polysiloxane (3) having an acid-dissociable group, when the total number of the halogen atom for $R^1$ and the group $-OR^3$ in the formula (2-A) is two or three, or when m in the formula (2-A) is 0 or 1. The other silicon-containing alicyclic compounds (2), i.e. those having the formula (2-A) wherein the total number of the halogen atom for $R^1$ and the group $-OR^3$ is one, or m is 2, or those having the above the formula (2-B), or their hydrolysis products, may also be used in the polycondensation reaction to adjust the molecular weight or molecular structure of polysiloxane (3).

The silicon-containing alicyclic compound (2) is also useful as a raw material for producing common polysiloxane resins and other silicon-containing alicyclic compounds having similar norbornane-type cyclic structure.

Polysiloxane (3)

Polysiloxane (3) has the above structural unit (I-1) or structural unit (II-1), or both.

As examples of the monovalent hydrocarbon group having 1–20 carbon atoms, monovalent halogenated hydrocarbon group having 1–20 carbon atoms, halogen atom, or secondary or tertiary amino group represented by $R^1$ in the structural unit (II-1), the corresponding groups previously mentioned in connection with the group $R^1$ in the structural unit (II) of the polysiloxane (1) can be given.

A methyl group, ethyl group, cyclopentyl group, cyclohexyl group, norbornyl group, tetracyclodecanyl group, and the like can be given as preferable monovalent hydrocarbon groups having 1–20 carbon atoms represented by $R^1$ in the structural unit (II-1). Given as examples of preferable halogenated hydrocarbon groups having 1–20 carbon atoms represented by $R^1$ are a trifluoromethyl group, pentafluoroethyl group, 3,3,3,2,2-pentafluoro-n-propyl group, pentafluorophenyl group, o-fluorophenyl group, m-fluorophenyl group, p-fluorophenyl group, 2,3-difluorophenyl group, 2,4-difluorophenyl group, 2,5-difluoro phenyl group, 2,6-difluorophenyl group, 3,4-difluoro phenyl group, 3,5-difluorophenyl group, 2,3,4-trifluorophenyl group, 2,3,5-trifluorophenyl group, 2,3,6-trifluorophenyl group, 2,4,6-trifluorophenyl group, 3,4,5-trifluorophenyl group, pentafluorophenyl group, a group of the formula (ii) in which 5 Rf's are fluorine atoms and b is 1, a group of the formula (ii) in which 5 Rf's are fluorine atoms and b is 2, and the like. A chlorine atom is a preferable halogen represented by $R^1$, and an amino group, dimethylamino group, diethylamino group, dicyclopentylamino group, dicyclohexylamino group, diphenylamino group, and the like are preferable amino-groups represented by $R^1$.

Particularly preferable groups represented by $R^1$ in the structural unit (II-1) are a methyl group, ethyl group, cyclopentyl group, cyclohexyl group, phenyl group, pentafluorophenyl group, chlorine atom, dimethylamino group, and the like.

As the group R in the structural unit (I-1) and structural unit (II-1) of the polysiloxane (3), both the hydrogen atom and methyl group are preferable. One is a preferable integer for n'. The n' in the structural unit (I-1) and n' in the structural unit (II-1) may be either the same or different.

The structural unit shown by the following formula (I-1-1) can be given as a specific example of the structural unit (I-1):

(I-1-1)

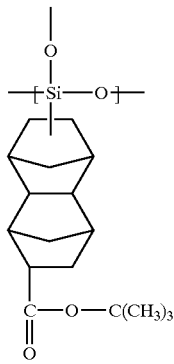

The structural units shown by the following formulas (II-1-1) to (II-1-4) can be given as specific examples of the structural unit (II-1):

(II-1-1)

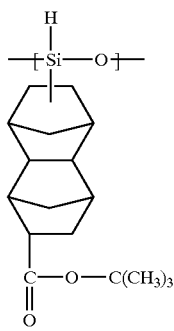

(II-1-2)

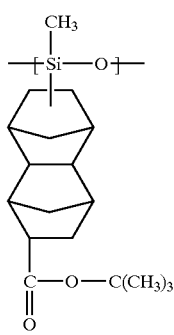

(II-1-3)

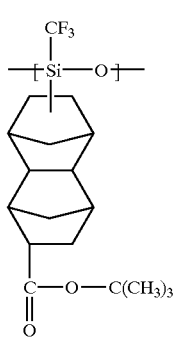

(II-1-4)

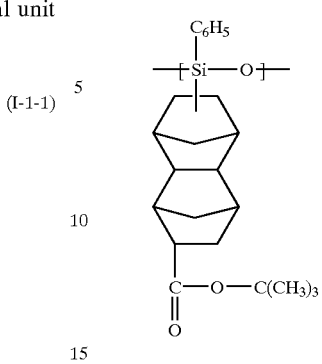

In the polysiloxane (3), the t-butoxycarbonyl group in the structural units (I-1) and (II-1) is an acid-dissociable group which dissociates in the presence of an acid and produces a carboxyl group.

The structural unit (I-1) and the structural unit (II-1) may be used in the polysiloxane (3) either individually or in combination of two or more.

The content of these structural units in the polysiloxane (3) may vary according to the types and combinations of the structural units, the application of the polysiloxane (3), and the like. A preferable specific content of each unit may be suitably determined by experiments. The amount of the structural unit (I-1) is usually 1–100 mol %, preferably 2–100 mol %, and particularly preferably 5–100 mol % of the total amount of the structural units. The amount of the structural unit (II-1) is usually 0–100 mol %, preferably 1–100 mol %, and particularly preferably 2–100 mol % of the total amount of the structural units. The total of the structural units (I-1) and (II-1) is usually 1–100 mol %, preferably 2–100 mol %, and particularly preferably 5–100 mol % of the total amount of the structural units.

If the amount of the structural unit (I-1) is less than 1 mol %, resolution of the resulting radiation-sensitive resin composition tends to decrease. If the total amount of the structural unit (I-1) and structural unit (II-1) is less than 1 mol %, the resulting radiation-sensitive resin composition may have poor solubility in an alkaline developer.

The amount of the structural units other than structural units (I-1) and (II-1) is usually 99 mol % or less, and preferably 95 mol % or less, of the total amount of structural units.

The total amount of bi-functional structural units in the polycondensation reaction is usually 0–100 mol %, and preferably 1–100 mol %. The total amount of tri-functional structural units in the polycondensation reaction is usually 1–100 mol %, and preferably 2–100 mol %. The total amount of tetra-functional structural units in the polycondensation reaction is usually 98 mol % or less, and preferably 95 mol % or less.

Usually, polysiloxane (3) has a ladder structure as part of the molecular structure. The ladder structure is principally introduced by a raw material having tri- or greater functional structure with respect to the polycondensation reaction.

Mw of Polysiloxane (3) is usually 500–1,000,000, preferably 500–500,000, and particularly preferably 1,000–100,000. If the Mw is less than 500, the glass transition temperature of the resulting polymer tends to decrease. If the Mw exceeds 1,000,000, solubility of the polymer in solvents tends to decrease.

The glass transition temperature (Tg) of polysiloxane (3) is usually from −50 to 500° C., and preferably from 0 to 300° C. If the glass transition temperature (Tg) of polysiloxane (3) less than −50° C., pattern formation using the resulting radiation-sensitive resin composition may be difficult. If more than 500° C., solubility of the polymer in solvents tends to decrease.

Polysiloxane (3) is usually insoluble or scarcely soluble in alkali, but becomes alkali-soluble when the acid-dissociable group dissociates in the presence of an acid. Thus, the polymer is particularly useful as an acid-dissociable group-containing resin component in radiation-sensitive resin compositions for microprocessing using various types of radiation such as deep ultraviolet radiation, electron beams, and X-rays.

Polysiloxane (3) is also useful as a material for fabricating formed articles and films, and as laminating materials, components for coating compositions, and the like.

Silicon-containing Alicyclic Compound (4)

In the silicon-containing alicyclic compound (4), as examples of the monovalent hydrocarbon group having 1–20 carbon atoms, monovalent halogenated hydrocarbon group having 1–20 carbon atoms, halogen atom, or secondary or tertiary amino group represented by $R^1$, the corresponding groups previously mentioned in connection with the group $R^1$ in the structural unit (II) of the polysiloxane (1) can be given.

A methyl group, ethyl group, cyclopentyl group, cyclohexyl group, norbornyl group, tetracyclodecanyl group, and the like can be given as preferable monovalent hydrocarbon groups having 1–20 carbon atoms represented by $R^1$. Given as examples of preferable halogenated hydrocarbon groups having 1–20 carbon atoms represented by $R^1$ are a trifluoromethyl group, pentafluoroethyl group, 3,3,3,2,2-pentafluoro-n-propyl group, pentafluorophenyl group, o-fluorophenyl group, m-fluorophenyl group, p-fluorophenyl group, 2,3-difluorophenyl group, 2,4-difluorophenyl group, 2,5-difluoro phenyl group, 2,6-difluorophenyl group, 3,4-difluoro phenyl group, 3,5-difluorophenyl group, 2,3,4-trifluorophenyl group, 2,3,5-trifluorophenyl group, 2,3,6-trifluorophenyl group, 2,4,6-trifluorophenyl group, 3,4,5-trifluorophenyl group, a group of the formula (ii) in which 5 Rf's are fluorine atoms and b is 1, a group of the formula (ii) in which 5 Rf's are fluorine atoms and b is 2, and the like. A chlorine atom is a preferable halogen represented by $R^1$, and an amino group, dimethylamino group, diethylamino group, dicyclopentylamino group, dicyclohexylamino group, diphenylamino group, and the like are preferable amino groups represented by $R^1$.

Particularly preferable groups represented by $R^1$ in the silicon containing alicyclic compound (4) are a methyl group, ethyl group, cyclohexyl group, phenyl group, pentafluorophenyl group, chlorine atom, dimethylamino group, and the like.

As examples of the monovalent hydrocarbon group having 1–20 carbon atoms and monovalent halogenated hydrocarbon group having 1–20 carbon atoms represented by $R^3$, the corresponding groups previously mentioned in connection with the group $R^1$ in the structural unit (II) of the polysiloxane (1) can be given.

A methyl group, ethyl group, n-propyl group, i-propyl group, and the like can be given as preferable monovalent hydrocarbon groups having 1–20 carbon atoms represented by $R^3$. Given as examples of preferable halogenated hydrocarbon groups having 1–20 carbon atoms represented by $R^3$ are a trifluoromethyl group, pentafluoroethyl group, 3,3,3,2,2-pentafluoro-n-propyl group, pentafluorophenyl group, o-fluorophenyl group, m-fluorophenyl group, p-fluorophenyl group, 2,3-difluorophenyl group, 2,4-difluorophenyl group, 2,5-difluoro phenyl group, 2,6-difluorophenyl group, 3,4-difluoro phenyl group, 3,5-difluorophenyl group, 2,3,4-trifluorophenyl group, 2,3,5-trifluorophenyl group, 2,3,6-trifluorophenyl group, 2,4,6-trifluorophenyl group, 3,4,5-trifluorophenyl group, a group of the formula (ii) in which 5 Rf's are fluorine atoms and b is 1, a group of the formula (ii) in which 5 Rf's are fluorine atoms and b is 2, and the like.

As the group represented by the formula (i) in $R^3$, the corresponding groups given as examples relating to $R^3$ of the silicon-containing alicyclic compound (2) can be given.

Particularly preferable groups as the group X in the formula (i) are a methyl group, phenyl group, methoxy group, and the like. The integer represented by a in the formula (i) is preferably 1 to 5.

Particularly preferable groups represented by $R^3$ in the silicon containing alicyclic compound (4) are a methyl group, ethyl group, t-butyl group, trimethylsilyl group, and the like.

As the group R in the silicon containing alicyclic compound (4), both the hydrogen atom and methyl group are preferable. As the group Rf, a hydrogen atom, methyl group, and trifluoromethyl group are preferable. A preferable integer for m and n is 0 or 1.

As examples of the hydrocarbon group having 1–20 carbon atoms, halogenated hydrocarbon group having 1–20 carbon atoms, halogen atom, or primary, secondary, or tertiary amino group represented by Y, the corresponding groups previously mentioned in connection with the group $R^1$ in the structural unit (II) of the polysiloxane (1) can be given.

As preferable examples of silicon containing alicyclic compound (4) in which Z is a hydrogen atom, compounds shown by the following formulas (4-1) to (4-100) can be given. In the following formulas, Rf represents a hydrogen atom, methyl group, or trifluoromethyl group, and Me indicates a methyl group.

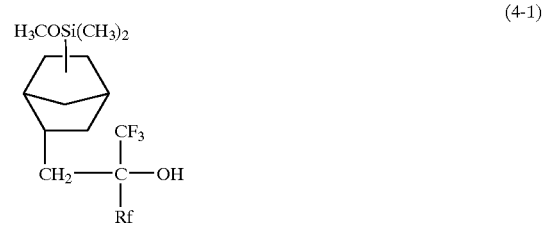

(4-1)

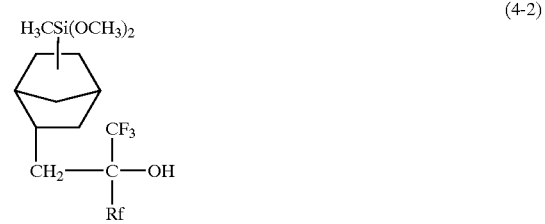

(4-2)

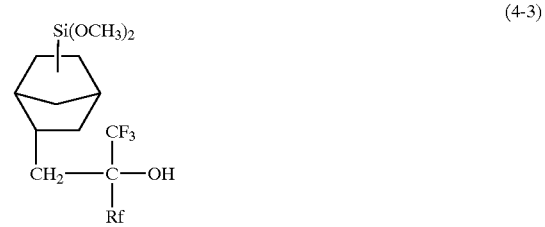

(4-3)

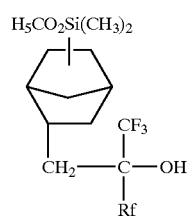 (4-4)
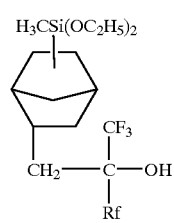 (4-5)
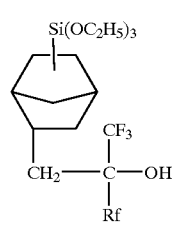 (4-6)
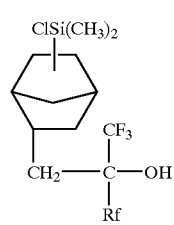 (4-7)
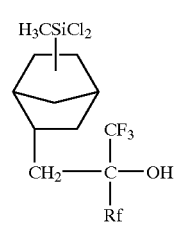 (4-8)
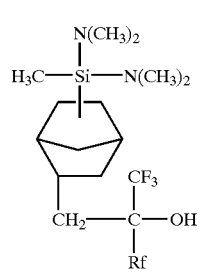 (4-9)
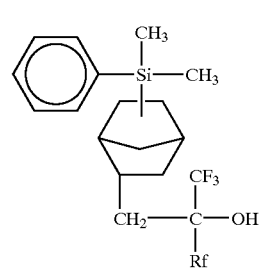 (4-10)
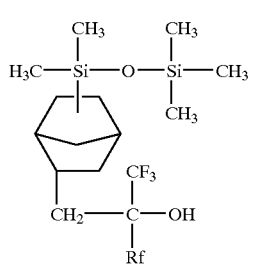 (4-11)
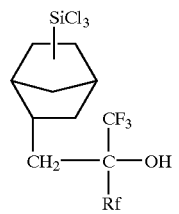 (4-12)
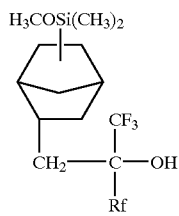 (4-13)
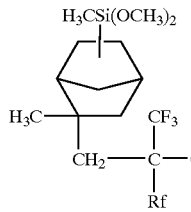 (4-14)
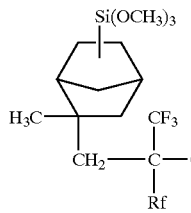 (4-15)
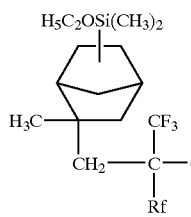 (4-16)
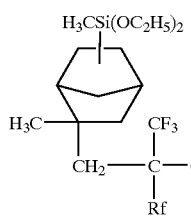 (4-17)

(4-18) 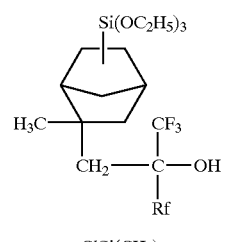
(4-19) 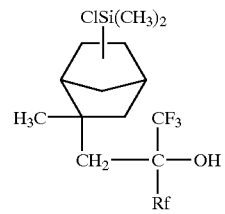
(4-20) 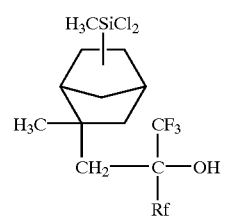
(4-21) 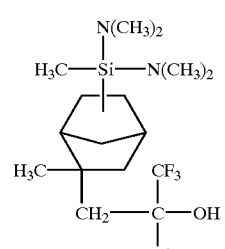
(4-22) 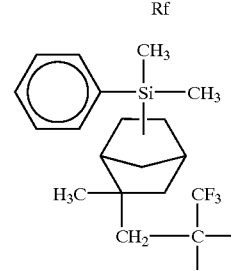
(4-23) 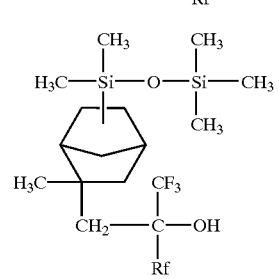
(4-24) 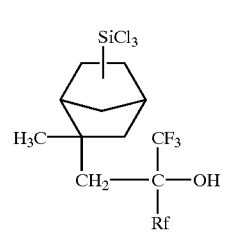
(4-25) 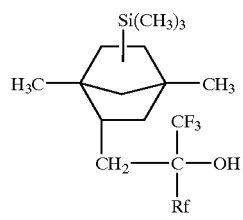
(4-26) 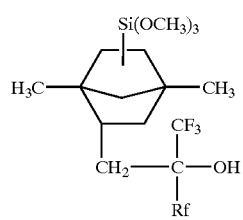
(4-27) 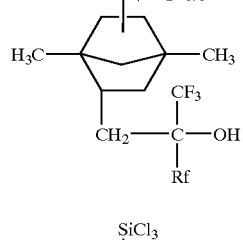
(4-28) 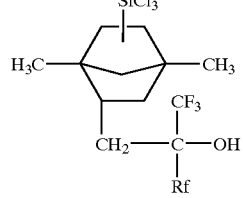
(4-29) 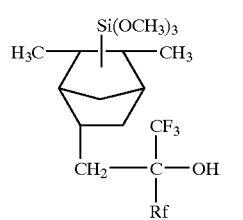
(4-30) 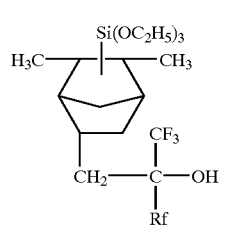
(4-31)

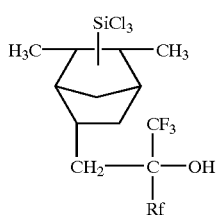
(4-32)
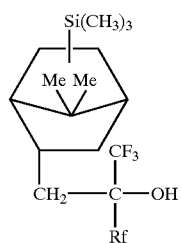
(4-33)
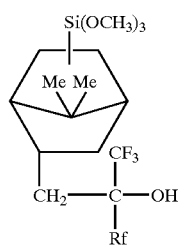
(4-34)
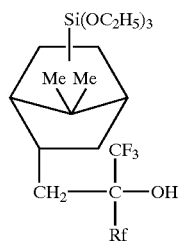
(4-35)
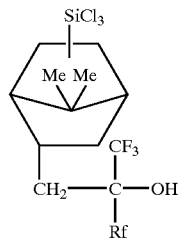
(4-36)
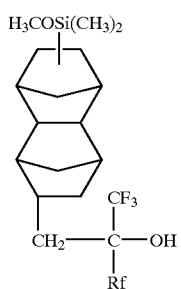
(4-37)
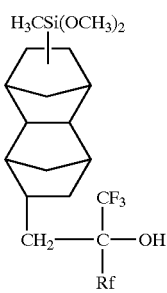
(4-38)
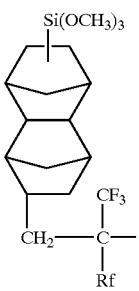
(4-39)
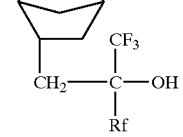
(4-40)
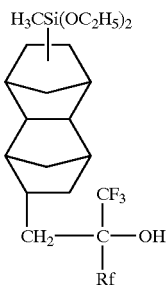
(4-41)
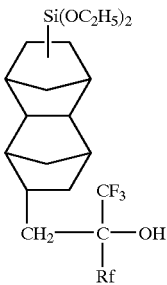
(4-42)

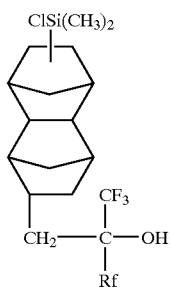 (4-43)
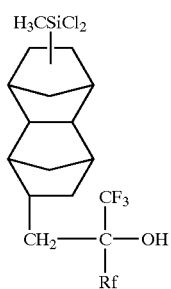 (4-44)
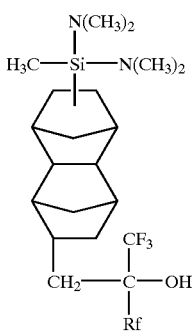 (4-45)
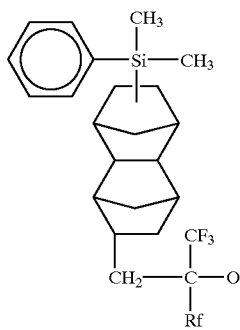 (4-46)
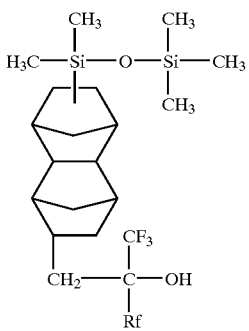 (4-47)
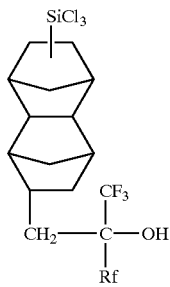 (4-48)
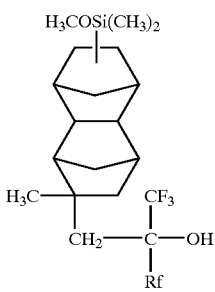 (4-49)
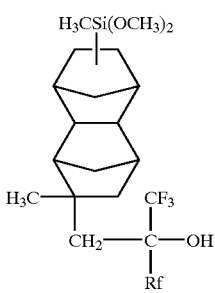 (4-50)
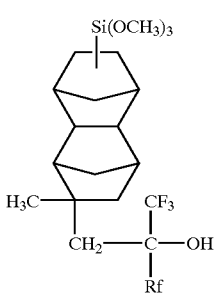 (4-51)
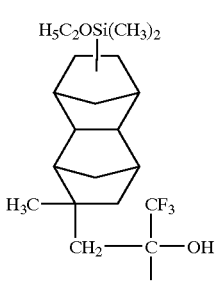 (4-52)

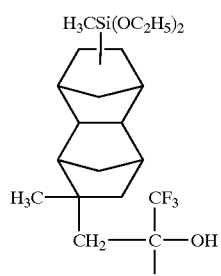
(4-53)
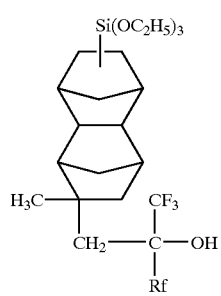
(4-54)
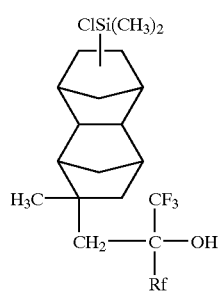
(4-55)
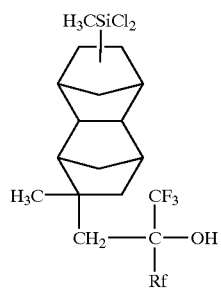
(4-56)
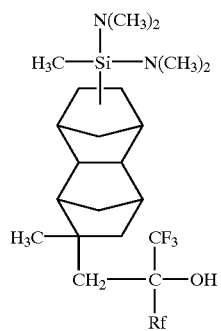
(4-57)
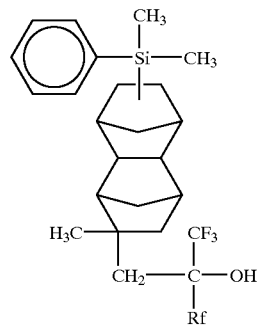
(4-58)
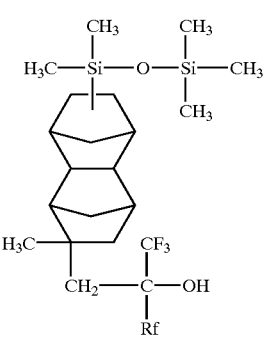
(4-59)
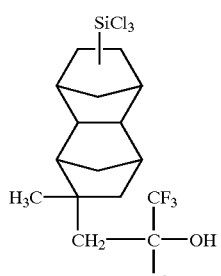
(4-60)
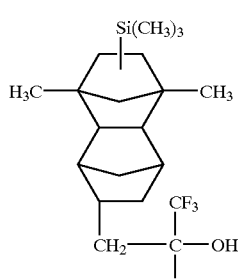
(4-61)
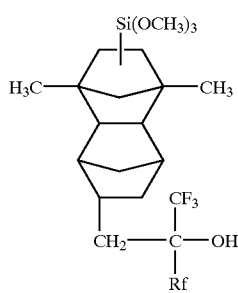
(4-62)

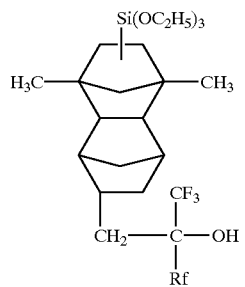
(4-63)
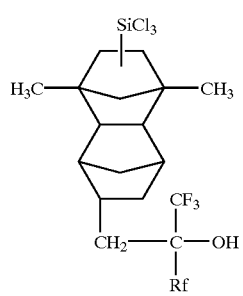
(4-64)
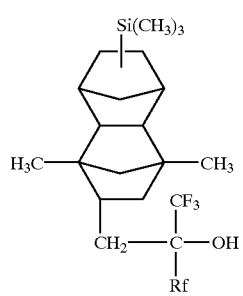
(4-65)
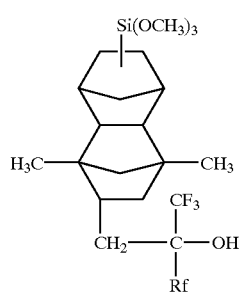
(4-66)
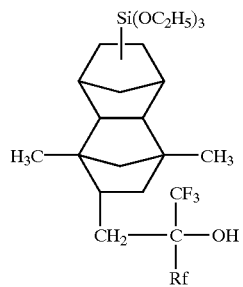
(4-67)
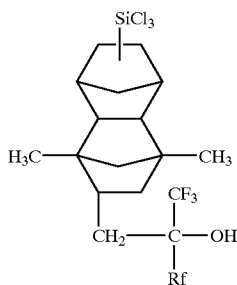
(4-68)
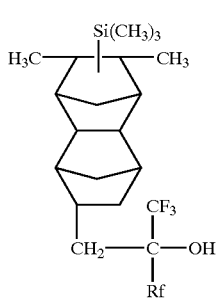
(4-69)
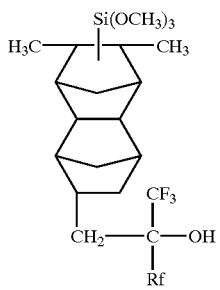
(4-70)
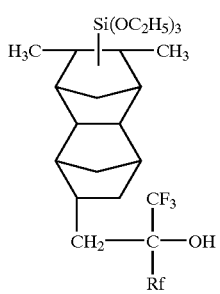
(4-71)
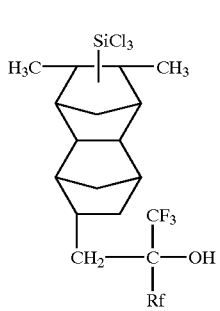
(4-72)

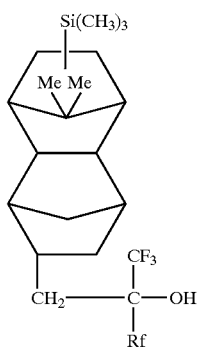
(4-73)
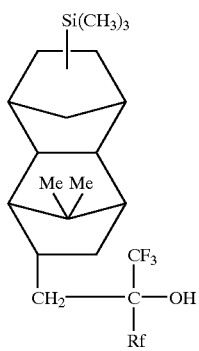
(4-77)
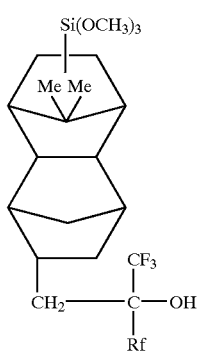
(4-74)
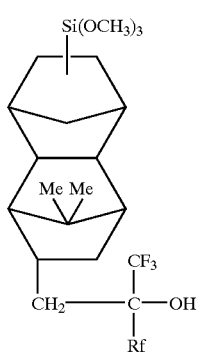
(4-78)
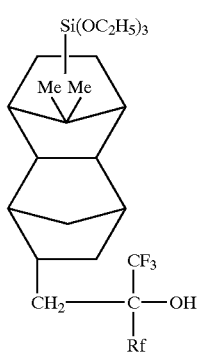
(4-75)
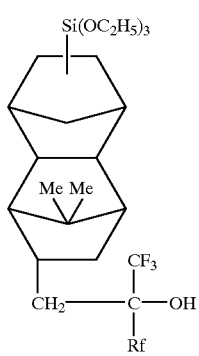
(4-79)
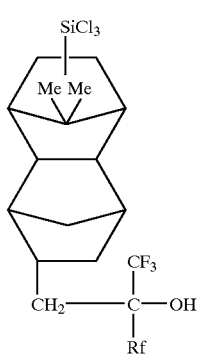
(4-76)
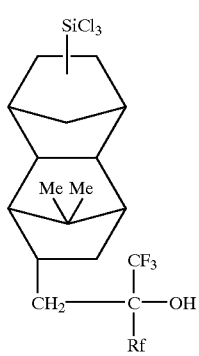
(4-80)

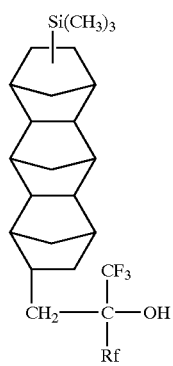 (4-81)
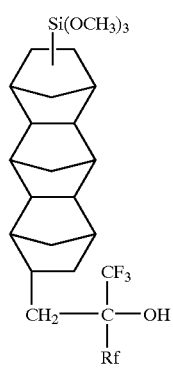 (4-82)
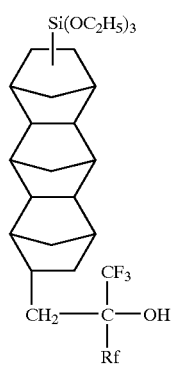 (4-83)
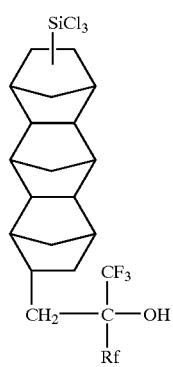 (4-84)
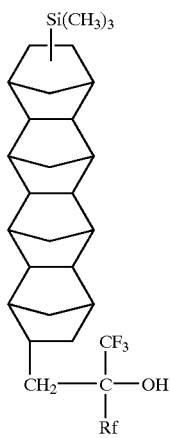 (4-85)
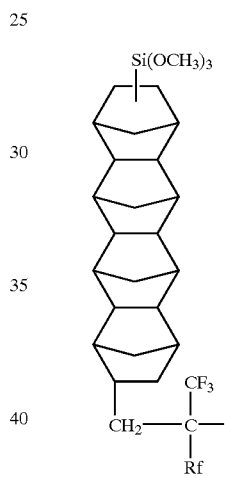 (4-86)
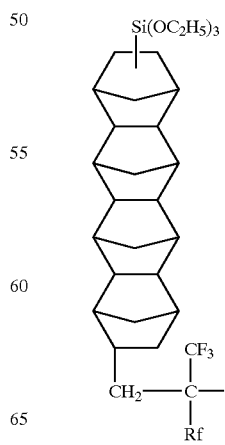 (4-87)

(4-88)
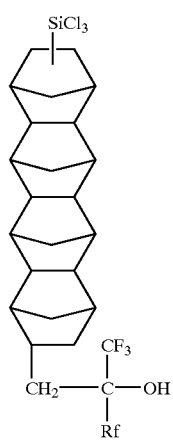
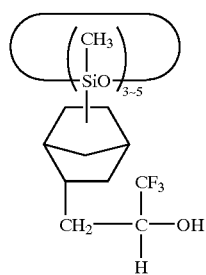
(4-89)
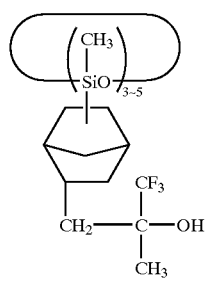
(4-90)
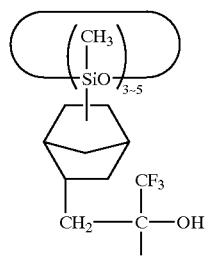
(4-91)
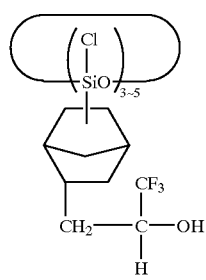
(4-92)
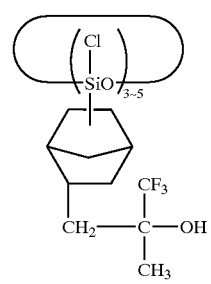
(4-93)
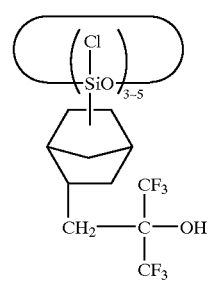
(4-94)
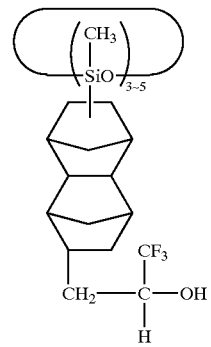
(4-95)
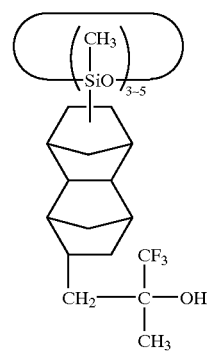
(4-96)
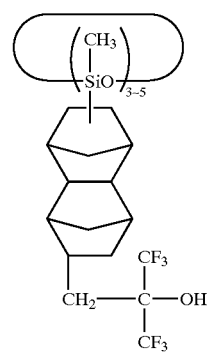
(4-97)

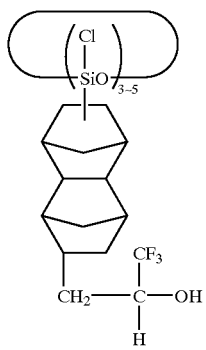

(4-98)

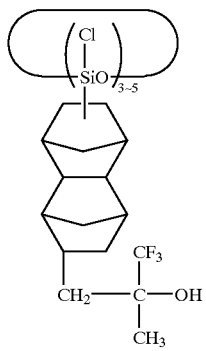

(4-99)

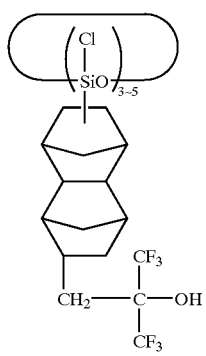

(4-100)

Of the above silicon containing alicyclic compound (4), compounds shown by the formulas (4-2), (4-3), (4-5), (4-6), (4-8), (4-9), (4-10), (4-11), and (4-12) are particularly preferable (provided that Rf in these formulas represents a trifluoromethyl group).

The following compounds can be given as preferable examples of the silicon containing alicyclic compound (4), wherein Z is a monovalent organic group dissociating hydrogen atoms by the action of an acid.

Compounds derived from the compound shown by the above formulas (4-1) to (4-100) (provided that Rf in these formulas is a hydrogen atom) by replacing the hydrogen atom in the hydroxyl group with a t-butyl group, t-butoxycarbonyl group, tetrahydropyranyl group, tetrahydrofuranyl group, methoxymethyl group, ethoxymethyl group, 1-methoxyethyl group, or 1-ethoxyethyl group.

Compounds derived from the compound shown by the above formulas (4-1) to (4-100) (provided that Rf in these formulas is a methyl group) by replacing the hydrogen atom in the hydroxyl group with a t-butyl group, t-butoxycarbonyl group, tetrahydropyranyl group, tetrahydrofuranyl group, methoxymethyl group, ethoxymethyl group, 1-methoxyethyl group, or 1-ethoxyethyl group.

Compounds derived from the compound shown by the above formulas (4-1) to (4-100) (provided that Rf in these formulas is a trifluoromethyl group) by replacing the hydrogen atom in the hydroxyl group with a t-butyl group, t-butoxycarbonyl group, tetrahydropyranyl group, tetrahydrofuranyl group, methoxymethyl group, ethoxymethyl group, 1-methoxyethyl group, or 1-ethoxyethyl group.

Of the above silicon containing alicyclic compound (4), wherein Z is a monovalent organic group dissociating hydrogen atoms by the action of an acid, particularly preferable compounds are the compounds derived from the compound shown by the above formulas (4-2), (4-3), (4-5), (4-6), (4-8), (4-9), (4-10), (4-11), or (4-12) (provided that Rf in these formulas represents a trifluoromethyl group)) by replacing the hydrogen atom in the hydroxyl group with a t-butyl group, t-butoxycarbonyl group, tetrahydropyranyl group, tetrahydrofuranyl group, methoxymethyl group, ethoxymethyl group, 1-methoxyethyl group, or 1-ethoxyethyl group.

The silicon containing alicyclic compound (4) having a hydrogen atom for the group Z is particularly useful as a raw material for synthesizing the silicon containing alicyclic compound (4), wherein Z is a monovalent organic group dissociating hydrogen atoms by the action of an acid.

The silicon containing alicyclic compound (4), in which Z is a hydrogen atom and the total number of the halogen atom for $R^1$ and the group $—OR^3$ is two or three, or the silicon containing alicyclic compound (4), in which m is 0 or 1, is very useful as a raw material for producing the alkali-soluble polysiloxane (5). The silicon containing alicyclic compounds (4), in which Z is a hydrogen atom and the total number of the halogen atom for $R^1$ and the group $—OR^3$ is one, or the silicon containing alicyclic compounds (4), in which Z is a hydrogen atom and m is 2, or the products obtained by previous hydrolysis of these compounds may also be used in the polycondensation reaction to adjust the molecular weight or molecular structure of polysiloxane (5).

In addition, the silicon-containing alicyclic compound (4) in which Z is a hydrogen atom is also useful as a raw material for producing common polysiloxane resins and other silicon-containing alicyclic compounds having similar norbornane-type cyclic structure.

The silicon-containing alicyclic compound (4) in which Z is a monovalent organic group dissociating hydrogen atoms by the action of an acid and m is 0 or 1 is very useful as a raw material for producing the polysiloxane (5) resins having an acid-dissociable group. The silicon-containing alicyclic compound (4) in which Z is a monovalent organic group dissociating hydrogen atoms by the action of an acid and m is 2, or its hydrolysis products may also be used in the polycondensation reaction to adjust the molecular weight or molecular structure of polysiloxane (5).

In addition, the silicon-containing alicyclic compound (4) in which Z is a monovalent organic group dissociating hydrogen atoms by the action of an acid is also useful as a raw material for producing common polysiloxane resins and other silicon-containing alicyclic compounds having similar norbornane-type cyclic structure.

Polysiloxane (5)

Polysiloxane (5) has the above structural unit (I-2) and/or structural unit (II-2) shown in the above formula (5).

As examples of the monovalent organic group dissociating hydrogen atoms by the action of an acid represented by Z in the structural unit (I-2) or structural unit (II-2), a tertiary alkyl group, a group forming an acetal group together with the oxygen atom with which the group Z binds (hereinafter referred to as an "acetal-forming group"), a substituted methyl group, 1-substituted ethyl group, 1-branched alkyl group (excluding tertiary alkyl groups), silyl group, germyl group, alkoxycarbonyl group, acyl group, cyclic acid-dissociating group, and the like can be given.

As examples of the tertiary alkyl group, acetal-forming group, substituted methyl group, 1-substituted ethyl group, 1-branched alkyl group, silyl group, germyl group, alkoxycarbonyl group, acyl group, and cyclic acid-dissociating group, the corresponding groups previously given as examples of Z' in the acid-dissociable group (γ) of polysiloxane (1) can be given.

As the group Z in the structural unit (I-2) or structural unit (II-2), a hydrogen atom, t-butyl group, t-butoxycarbonyl group, tetrahydropyranyl group, tetrahydrofuranyl group, methoxymethyl group, ethoxymethyl group, 1-methoxyethyl group, 1-ethoxyethyl group, and the like are preferable.

The Z in the structural unit (I-2) and Z in the structural unit (II-2) may be either the same or different.

As examples of the monovalent hydrocarbon group having 1–20 carbon atoms, monovalent halogenated hydrocarbon group having 1–20 carbon atoms, halogen atom, or secondary or tertiary amino group represented by $R^1$ in the structural unit (II-2), the corresponding groups previously mentioned in connection with the group $R^1$ in the structural unit (II) of the polysiloxane (1) can be given.

A methyl group, ethyl group, cyclopentyl group, cyclohexyl group, norbornyl group, tetracyclodecanyl group, and the like can be given as preferable monovalent hydrocarbon groups having 1–20 carbon atoms represented by $R^1$. Given as examples of preferable monovalent halogenated hydrocarbon groups having 1–20 carbon atoms represented by $R^1$ are a trifluoromethyl group, pentafluoroethyl group, 3,3,3,2,2-pentafluoro-n-propyl group, pentafluorophenyl group, o-fluorophenyl group, m-fluorophenyl group, p-fluorophenyl group, 2,3-difluorophenyl group, 2,4-difluorophenyl group, 2,5-difluoro phenyl group, 2,6-difluorophenyl group, 3,4-difluoro phenyl group, 3,5-difluorophenyl group, 2,3,4-trifluorophenyl group, 2,3,5-trifluorophenyl group, 2,3,6-trifluorophenyl group, 2,4,6-trifluorophenyl group, 3,4,5-trifluorophenyl group, pentafluorophenyl group, a group of the formula (ii) in which 5 Rf's are fluorine atoms and b is 1, a group of the formula (ii) in which 5 Rf's are fluorine atoms and b is 2, and the like. A chlorine atom is a preferable halogen represented by $R^1$, and an amino group, dimethylamino group, diethylamino group, dicyclopentylamino group, dicyclohexylamino group, diphenylamino group, and the like are preferable amino groups represented by $R^1$.

Particularly preferable groups represented by $R^1$ in the structural unit (II-2) are a methyl group, ethyl group, cyclopentyl group, cyclohexyl group, pentafluoroethyl group, chlorine atom, dimethylamino group, and the like.

As the group R in the structural unit (I-2) and structural unit (II-2) of the polysiloxane (5), both the hydrogen atom and methyl group are preferable. As the group Rf, any one of the hydrogen atom, methyl group, and trifluoromethyl group is preferable. 0 or 1 is preferable as the integer n. The Rf in the structural unit (I-2) and Rf in the structural unit (II-2) may be either the same or different. Also, n in the structural unit (I-2) and n in the structural unit (II-2) may be either the same or different.

The structural units shown by the following formulas (I-2-1) to (I-2-24) can be given as specific examples of the structural unit (I-2):

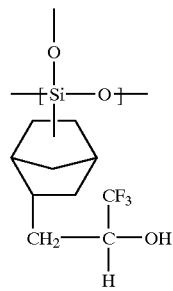

(I-2-1)

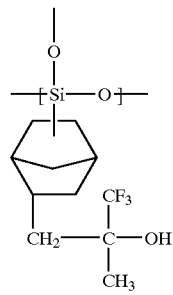

(I-2-2)

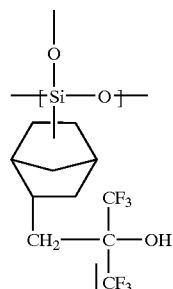

(I-2-3)

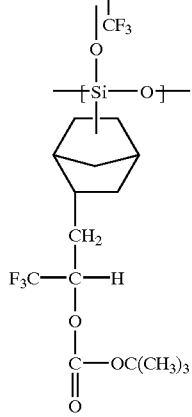

(I-2-4)

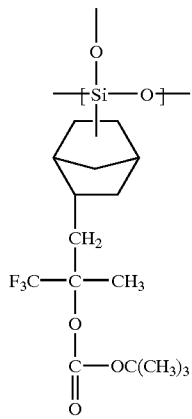

(I-2-5)

(I 2-6)
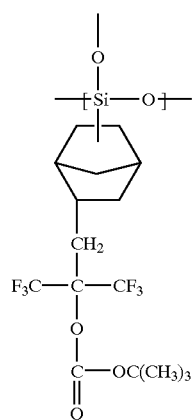
(I-2-7)
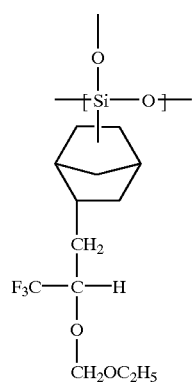
(I-2-8)
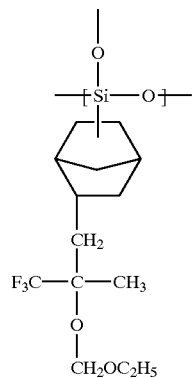
(I-2-9)
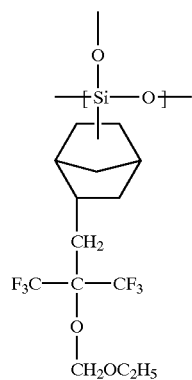
(I-2-10)
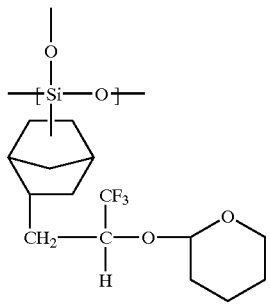
(I-2-11)
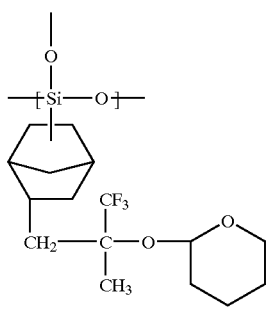
(I-2 12)
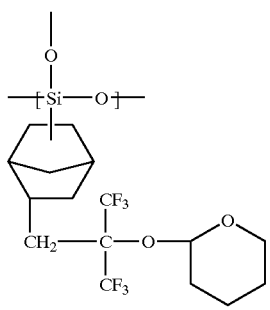
(I-2-13)
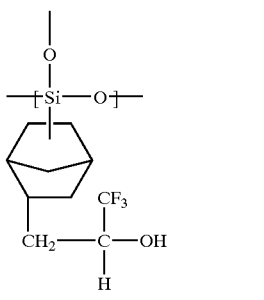
(I-2-14)
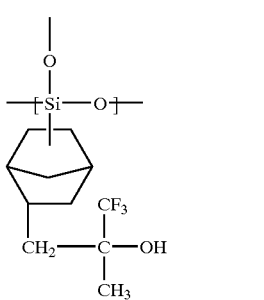

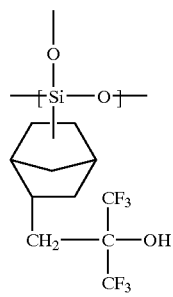 (I-2-15)
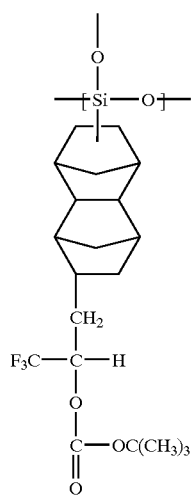 (I-2-16)
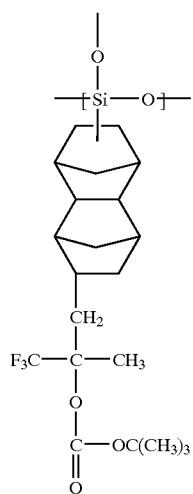 (I-2-17)
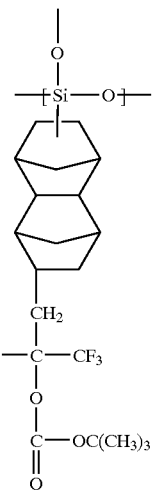 (I-2-18)
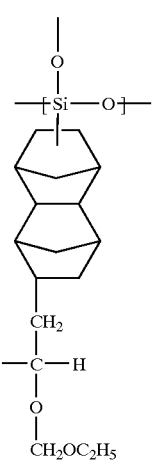 (I-2-19)
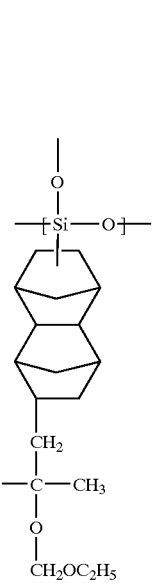 (I-2-20)

-continued
(I-2-21)
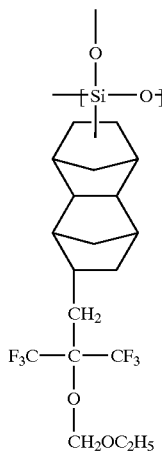
(I-2-22)
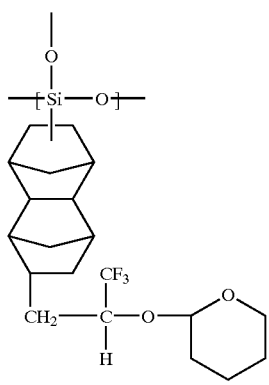
(I-2-23)
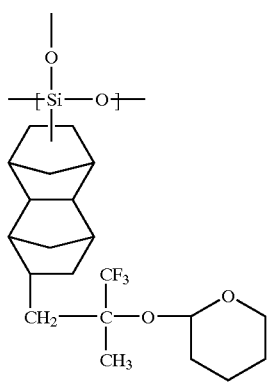
(I-2-24)
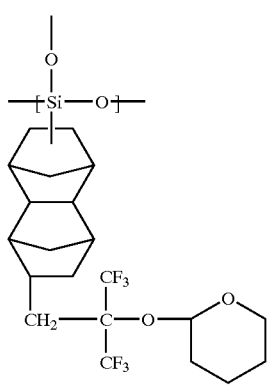
Of the above examples of structural unit (I-2), the structural units shown by the formulas (I-2-2), (1-2-3), (I-2-5), (I-2-6), (I-2-8), (I-2-9), (I-2-14), (I-2-15), (I-2-17), (I-2-18), (I-2-20), and (I-2-21) are particularly preferable.
The structural units shown by the following formulas (II-2-1) to (II-2-96) can be given as specific examples of the structural unit (II-2):
(II-2-1)
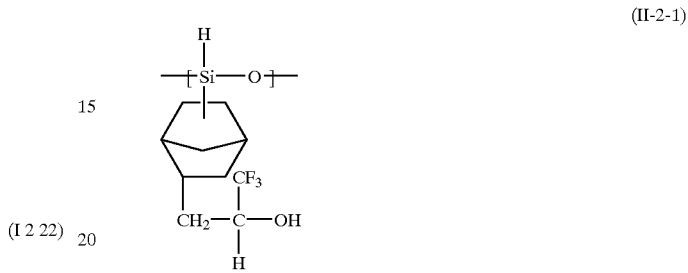
(II-2-2)
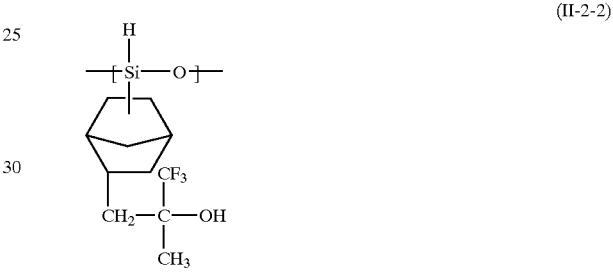
(II-2-3)
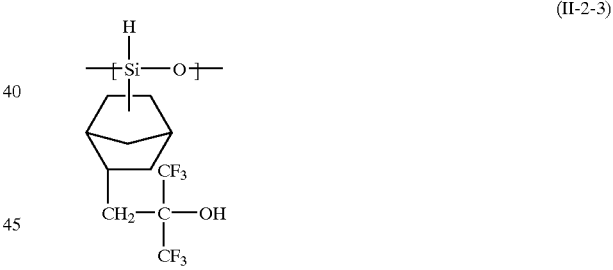
(II-2-4)
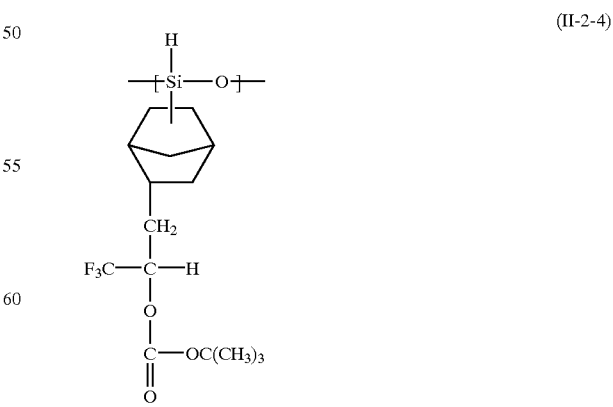

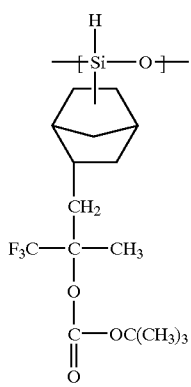 (II-2-5)
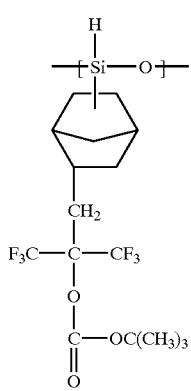 (II-2-6)
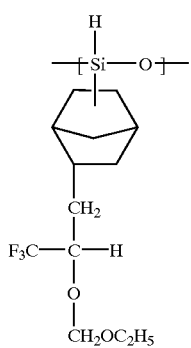 (II-2-7)
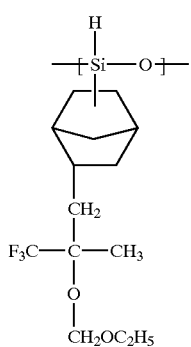 (II-2-8)
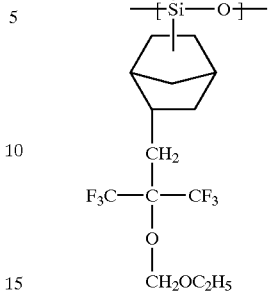 (II-2-9)
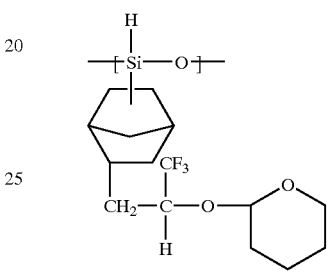 (II-2-10)
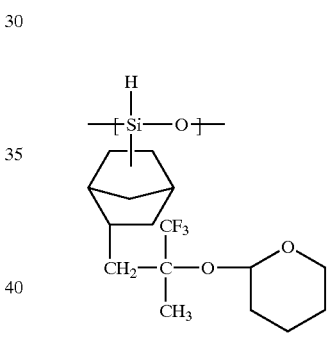 (II-2-11)
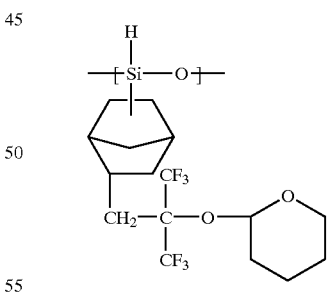 (II-2-12)
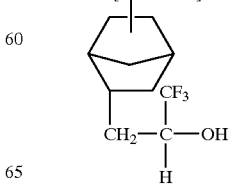 (II-2-13)

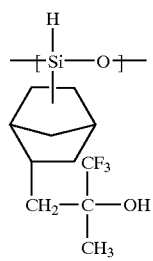 (II-2-14)
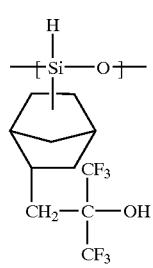 (II-2-15)
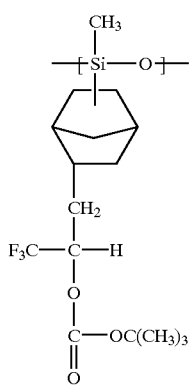 (II-2-16)
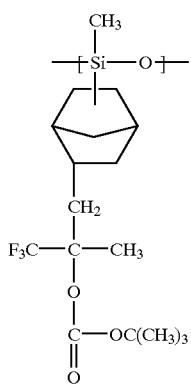 (II-2-17)
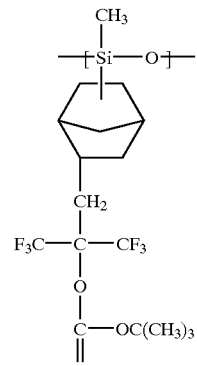 (II-2-18)
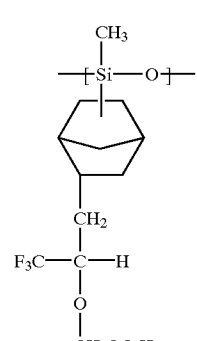 (II-2-19)
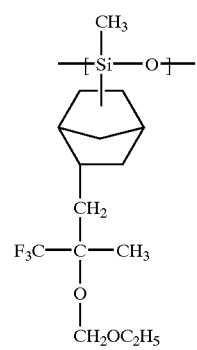 (II-2-20)
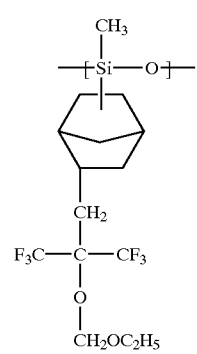 (II-2-21)

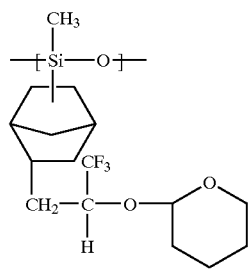
(II-2-22)
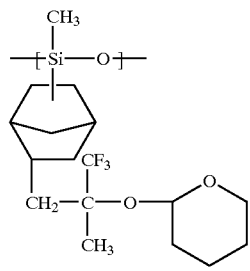
(II-2-23)
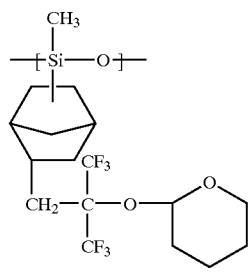
(II-2-24)
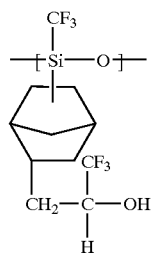
(II-2-25)
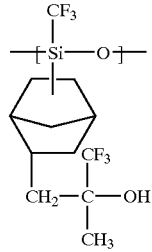
(II-2-26)
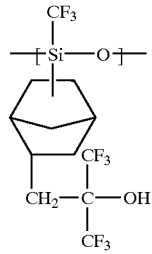
(II-2-27)
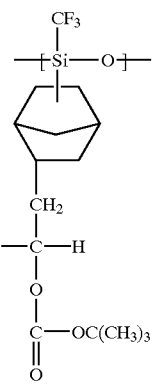
(II-2-28)
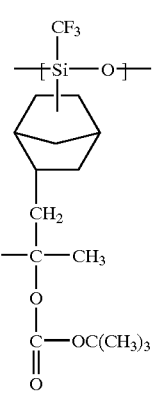
(II-2-29)
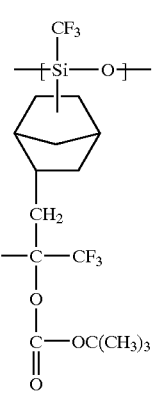
(II-2-30)
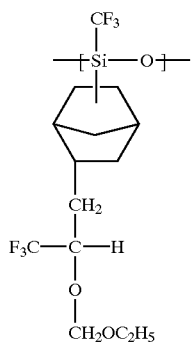
(II-2-31)

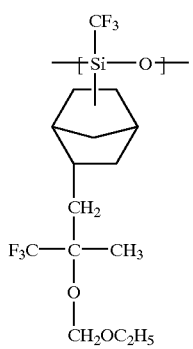
(II-2-32)
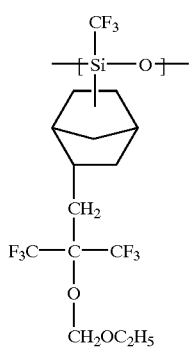
(II-2-33)
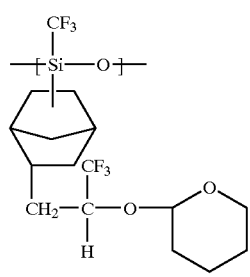
(II-2-34)
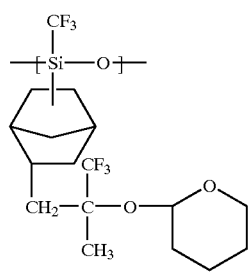
(II-2-35)
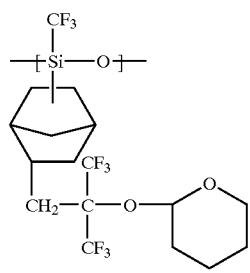
(II-2-36)
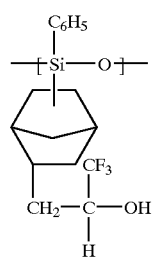
(II-2-37)
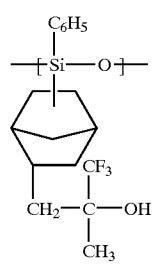
(II-2-38)
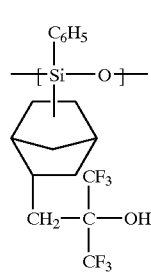
(II-2-39)
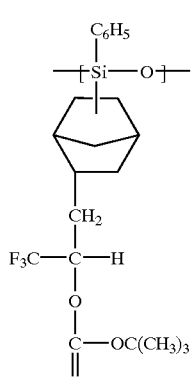
(II-2-40)
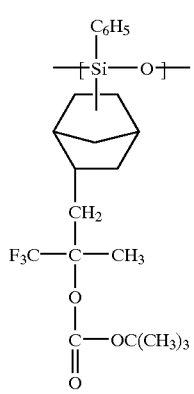
(II-2-41)

(II-2-42) 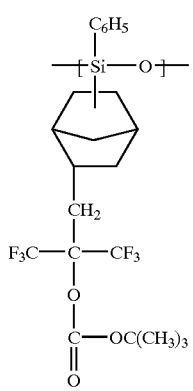
(II-2-43) 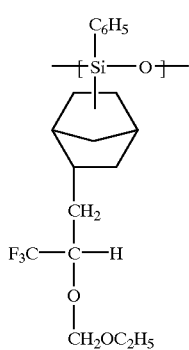
(II-2-44) 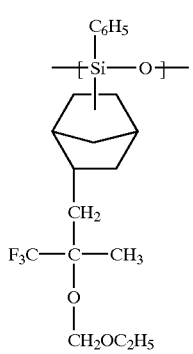
(II-2-45) 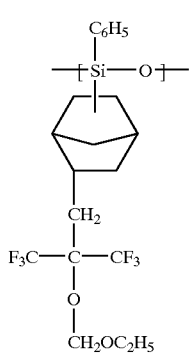
(II-2-46) 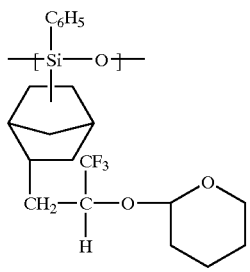
(II-2-47) 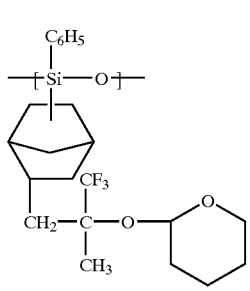
(II-2-48) 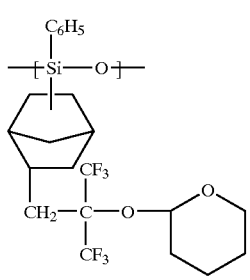
(II-2-49) 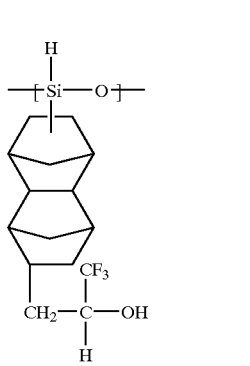
(II-2-50) 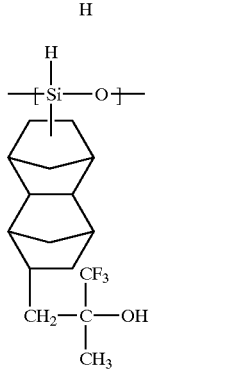

(II-2-51) 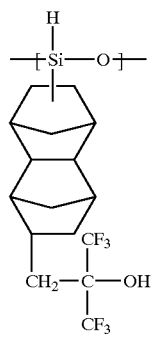
(II-2-52) 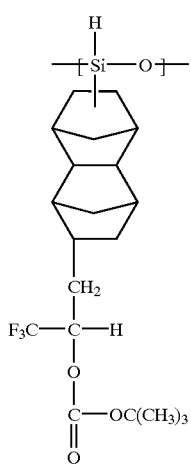
(II-2-53) 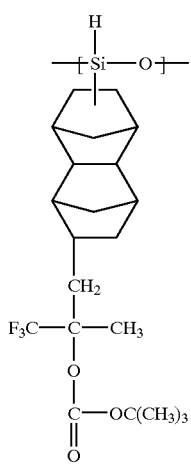
(II-2-54) 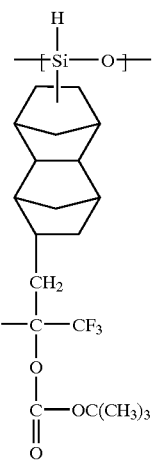
(II-2-55) 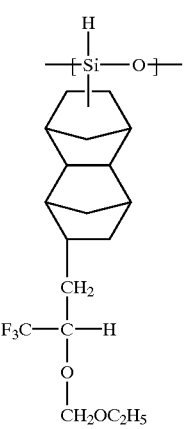
(II-2-56) 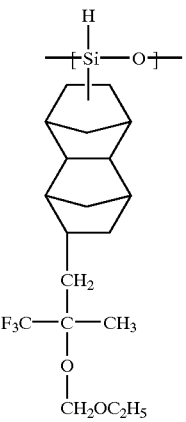

(II-2-57) 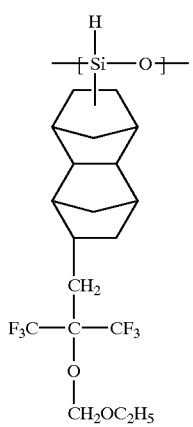
(II-2-58) 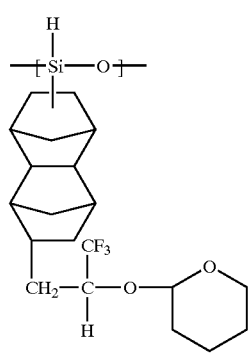
(II-2-59) 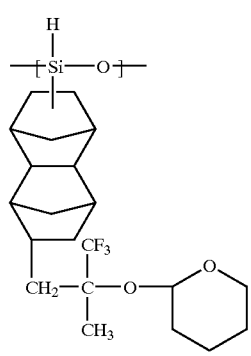
(II-2-60) 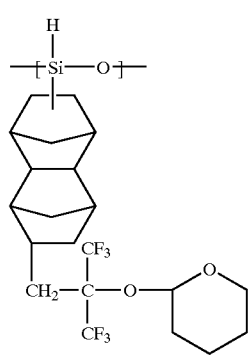
(II-2-61) 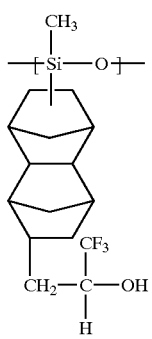
(II-2-62) 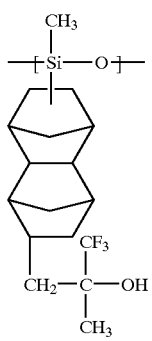
(II-2-63) 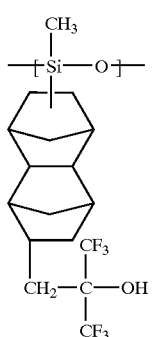
(II-2-64) 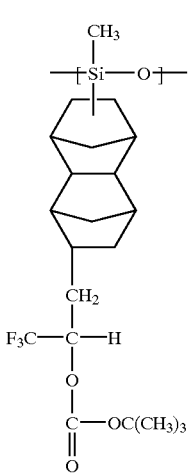

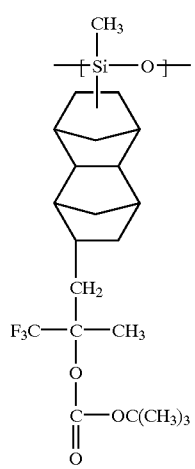
(II-2-65)
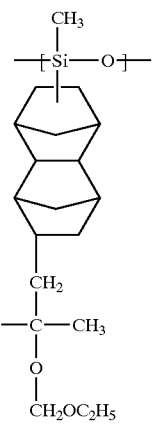
(II-2-68)
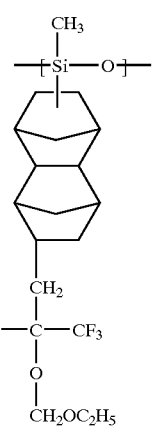
(II-2-69)
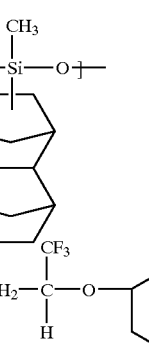
(II-2-70)
(II-2-66)
(II-2-67)
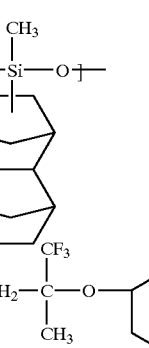
(II-2-71)

(II-2-72)
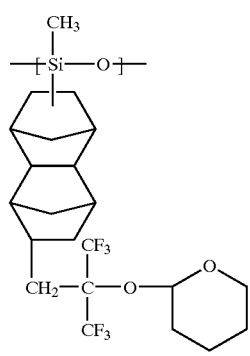
(II-2-73)
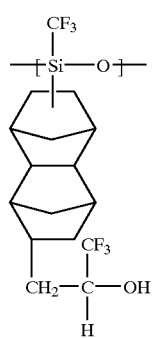
(II-2-74)
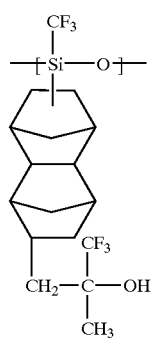
(II-2-75)
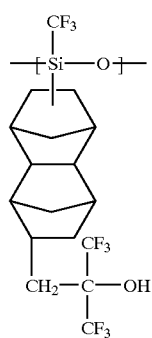
(II-2-76)
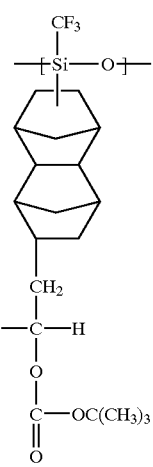
(II-2-77)
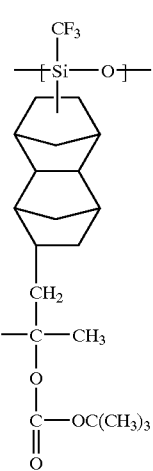
(II-2-78)
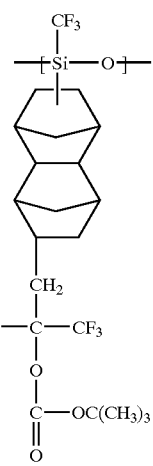

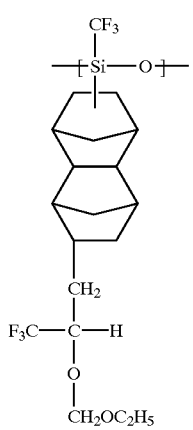 (II-2-79)
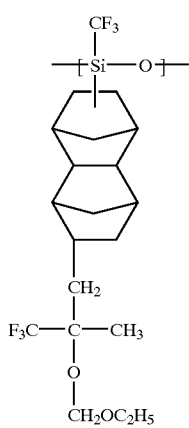 (II-2-80)
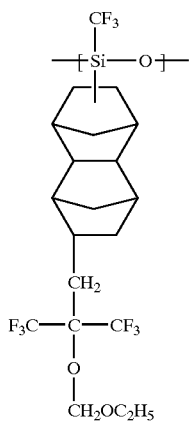 (II-2-81)
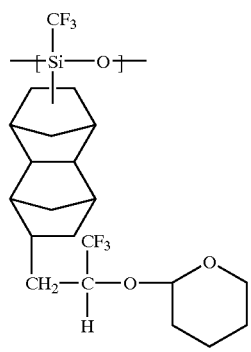 (II-2-82)
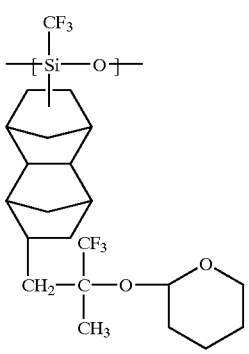 (II-2-83)
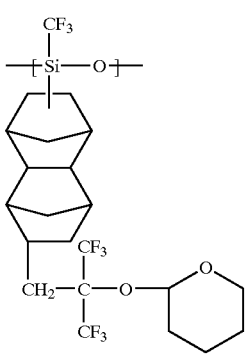 (II-2-84)
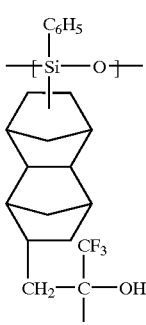 (II-2-85)
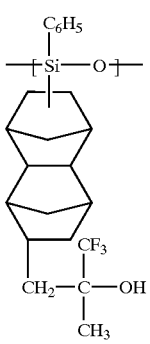 (II-2-86)

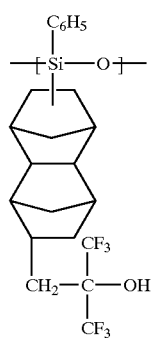 (II-2-87)
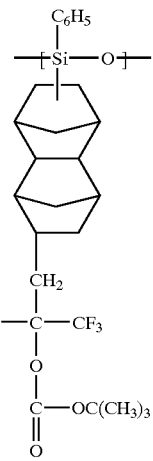 (II-2-90)
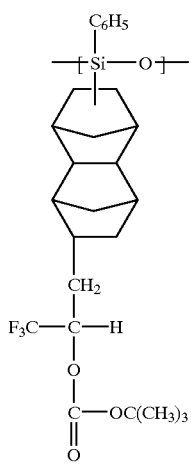 (II-2-88)
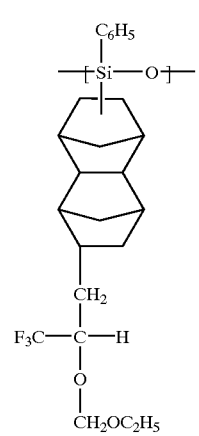 (II-2-91)
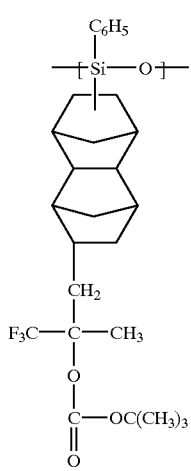 (II-2-89)
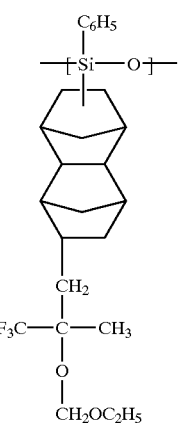 (II-2-92)

-continued

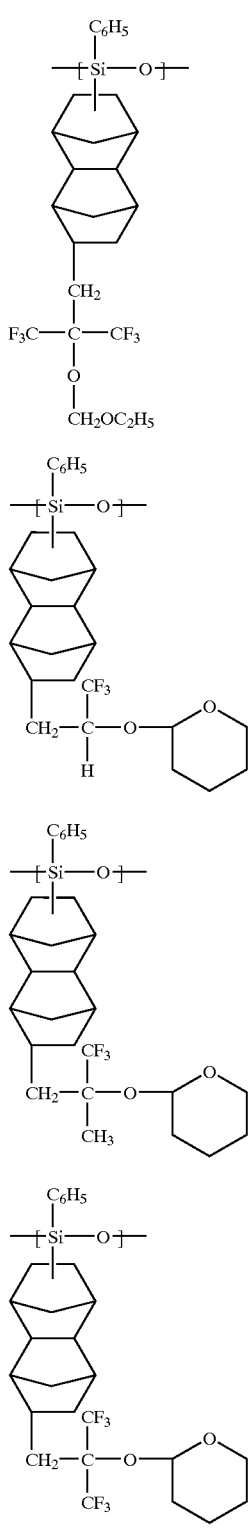

(II-2-93)

(II-2-94)

(II-2-95)

(II-2-96)

Of the above examples of structural unit (II), the structural units shown by the formulas: (II-2-14), (II-2-15), (II-2-17), (II-2-18), (II-2-20), (II-2-21), (II-2-26), (II-2-27), (II-2-29), (II-2-30), (II-2-32), (II-2-33), (II-2-62), (II-2-63), (II-2-65), (II-2-66), (II-2-68), (II-2-69), (II-2-74), (II-2-75), (II-2-77), (II-2-78), (II-2-80), and (II-2-81) are particularly preferable.

The structural unit (I-2) and the structural unit (II-2) may be used in the polysiloxane (5) either individually or in combination of two or more.

Usually, polysiloxane (5) has a ladder structure as part of the molecular structure. The ladder structure is principally introduced by a raw material having tri- or greater functional structure with respect to the polycondensation reaction.

The content of these structural units in the polysiloxane (5) may vary according to the types and combinations of the structural units, the application of the polysiloxane (5), and the like. A preferable specific content of each unit may be suitably determined by experiments. The amount of the structural unit (I-2) is usually 1–100 mol %, preferably 2–100 mol %, and particularly preferably 5–100 mol % of the total amount of the structural units. The amount of the structural unit (II-2) is usually 0–100 mol %, preferably 1–100 mol %, and particularly preferably 2–100 mol % of the total amount of the structural units. The total of the structural units (I-2) and (II-2) is usually 1–100 mol %, preferably 2–100 mol %, and particularly preferably 5–100 mol % of the total amount of the structural units.

If the amount of the structural unit (I-2) is less than 1 mol %, resolution of the resulting radiation-sensitive resin composition tends to decrease. If the total amount of the structural unit (I-2) and structural unit (II-2) is less than 1 mol %, the resulting radiation-sensitive resin composition may have poor solubility in an alkaline developer.

The amount of the structural units other than structural units (I-1) and (II-1) is usually 99 mol % or less, and preferably 95 mol % or less, of the total amount of structural units.

The total amount of bi-functional structural units in the polycondensation reaction is usually 0–100 mol %, and preferably 1–100 mol %. The total amount of tri-functional structural units in the polycondensation reaction is usually 1–100 mol %, and preferably 2–100 mol %. The total amount of tetra-functional structural units in the polycondensation reaction is usually 98 mol % or less, and preferably 95 mol % or less.

Mw of Polysiloxane (5) is usually 500–1,000,000, preferably 500–500,000, and particularly preferably 800–100,000. If the Mw is less than 500, the glass transition temperature of the resulting polymer tends to decrease. If the Mw exceeds 1,000,000, solubility of the polymer in solvents tends to decrease.

The glass transition temperature (Tg) of polysiloxane (5) is usually from −50 to 500° C., and preferably from 0 to 300° C. If the glass transition temperature (Tg) of polysiloxane (5) less than −50° C., pattern formation using the resulting radiation-sensitive resin composition may be difficult. If more than 500° C., solubility of the polymer in solvents tends to decrease.

The polysiloxane (5) having a hydrogen atom for Z is usually soluble in alkali and very useful as an alkali-soluble component in radiation-sensitive resin compositions for microprocessing using various types of radiation such as deep ultraviolet radiation, electron beams, and X-rays.

The polysiloxane (5) having a hydrogen atom for the group Z is also useful as a raw material for synthesizing the polysiloxane (5), wherein Z is a monovalent organic group dissociating hydrogen atoms by the action of an acid.

Polysiloxane (5), in which Z is a monovalent organic group dissociating hydrogen atoms by the action of an acid, is usually insoluble or scarcely soluble in alkali, but becomes alkali-soluble when the acid-dissociable group dissociates. Thus, the polymer is particularly useful as an acid-dissociable group-containing resin component in radiation-sensitive resin compositions for microprocessing using various types of radiation such as deep ultraviolet radiation, electron beams, and X-rays.

The polysiloxane (5) is also useful as a material for fabricating formed articles and films, and as laminating materials, components for coating compositions, and the like.

Synthesis of silicon-containing alicyclic compound (2) and silicon-containing alicyclic compound (4)

The silicon-containing alicyclic compound (2) and silicon-containing alicyclic compound (4) can be synthesized by the following method, for example.

① A method of reacting a corresponding norbornene derivative and corresponding hydrosilane compound in accordance with a conventional hydrosilyl-formation reaction using a hydrosilyl-formation catalyst in the presence or absence of a suitable solvent.

This reaction is shown by the following reaction formula in the case of the silicon-containing alicyclic compound (2) having the above-described formula (2-A):

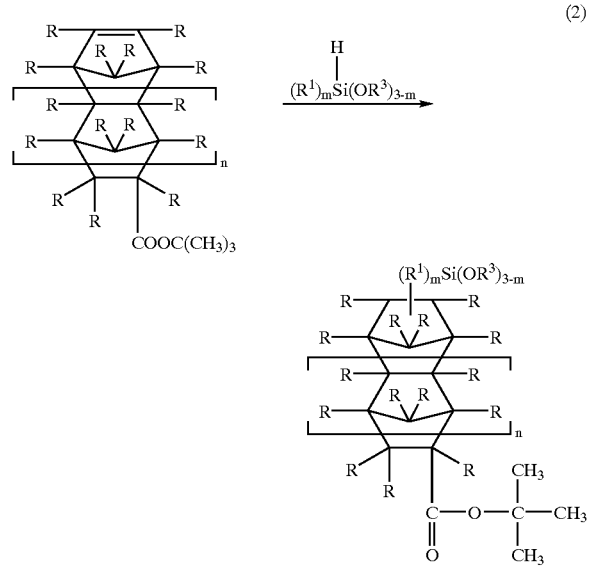

wherein R, $R^1$, $R^3$, m, and n have the same meanings as defined for the corresponding symbols in the formula (2-A). As examples of the hydrosilyl-forming catalyst, a transition metal catalyst, radical reaction initiator, and the like can be given.

Examples of a transition metal catalyst used as the hydrosilyl-forming catalyst include the following compounds: platinum catalysts such as $H_2PtCl_6$, $K_2PtCl_6$, $Na_2PtCl_6$, $(NH_4)_2PtCl_6$, $K_2PtCl_4$, $Na_2PtCl_4$, $(NH_4)_2PtCl_4$, $PtCl_2$, $H_2PtBr_6$, $K_2PtBr_6$, $Na_2PtBr_6$, $PtBr_4$, $K_2PtBr_4$, $PtBr_2$, $K_2PtI_6$, $Na_2PtI_6$, $PtI_4$, $PtI_2$, $PtCl_2(C_6H_5CN)$, $PtCl_2(CH_3CN)_2$, $PtCl_2[P(C_6H_5)_3]_2$, cis-$PtCl_2(styrene)_2$, cis-$PtCl_2(p$-chlorostyrene$)_2$, $KPtCl_3(styrene)_2$, $(n$-$Bu)_4NPtCl_3$ $(styrene)_2$ (provided that n-Bu indicates n-butyl group, hereinafter the same), the compound shown by the following formula (iii):

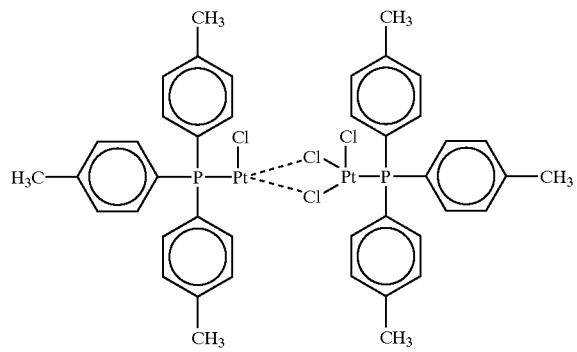

trans-$PtCl_2(NH_3)_2$, cis-$PtCl_2[P(C_2H_5)_3]_2$, cis-$PtCl_2[P(n$-$Bu)_3]_2$, $[(n$-$Bu)4N]_2PtCl_6$, $[P(C_6H_5)_4]_2PtCl_4$, $(n$-$Bu)_4NPtI_3(CO)$, $[(n$-$Bu)4N]_2$-cis-$PtCl_2(SnCl_3)_2$, $[(CH_3)_4N]_3Pt(SnCl_3)_5$, [bis(triphenylphosphine)imminum], $Pt(SnCl_3)_3[As(C_2H_5)_3]_2$, $(C_2H_5)_4NPt(SnCl_3)_3(1,5$-cyclooctadiene), platinum-activated carbon, platinum black, etc.; palladium catalysts such as $PdCl_2[P(C_6H_5)_3]_2$, $PdCl_2$ (1,5-cyclooctadiene), palladium-activated carbon, palladium black, etc.; rhodium catalysts such as $HRh[P(C_6H_5)_3]_4$, rhodium-activated carbon, etc.; iridium catalysts such as $IrCl_3$, etc.; ruthenium catalysts such as $RuCl_3$, etc.; cobalt catalysts such as $Co_2(CO)_8$, etc.; nickel catalysts such as $NiCl_2$, $NiBr_2$, $Ni(CN)_2$, etc.; and copper catalysts such as $CuCl_2$, $CuBr_2$, CuCl, CuBr, CuCN, etc.

Of these transition metal catalysts, platinum catalysts such as $H_2PtCl_6$, $K_2PtCl_6$, $Na_2PtCl_6$, $K_2PtCl_4$, $Na_2PtCl_4$, $PtCl_2$, $H_2PtBr_6$, $K_2PtBr_6$, $Na_2PtBr_6$, $K_2PtBr_4$, and platinum-activated carbon are preferable.

These transition metal catalysts may be used either individually or in combination of two or more.

The transition metal catalysts may be added as a solution in an organic solvent such as i-propyl alcohol.

These transition metal catalysts are usually used in the amount of 0.00001–1,000 parts by weight for 100 parts by weight of the hydrosilane compound.

As examples of the above-mentioned radical reaction initiator, benzoylperoxide, lauroylperoxide, diisopropylperoxydicarbonate, t-butylhydroperoxide, cumenehydroperoxide, di-t-butylperoxide, dicumylperoxide, azobisisobutyronitrile, azobis(2,4-dimethylvaleronitrile), azobis(4-methoxy-2,4-dimethylvaleronitrile), and the like can be given.

These radical reaction initiators may be used either individually or in combinations of two or more.

The radical reaction initiators are usually used in the amount of 0.01–1,000 parts by weight for 100 parts by weight of the hydrosilane compound.

The following solvents can be given as the solvent used in the hydrosilyl-forming reaction: aromatic hydrocarbons such as benzene, toluene, and xylene; aliphatic hydrocarbons such asn-hexane, n-heptane, and n-octane; ethers such as benzyl ethyl ether, di-n-hexyl ether, and tetrahydrofuran; halogenated hydrocarbons such as dichloromethane, chloroform, and 1,2-dichloroethane; linear or branched ketones such as 2-butanone, 2-pentanone, 3-methyl-2-butanone, 2-hexanone, 4-methyl-2-pentanone, 3-methyl-2-pentanone, 3,3-dimethyl-2-butanone, 2-heptanone, and 2-octanone; cyclic ketones such as cyclopentanone, 3-methylcyclopentanone, cyclohexanone, 2-methylcyclohexanone, 2,6-dimethylcyclohexanone, and isophorone; propylene glycol monoalkyl ether acetates such as propylene glycol monomethyl ether acetate, propylene glycol monoethyl ether acetate, propylene glycol mono-n-propyl ether acetate, propylene glycol mono-i-propyl ether acetate, propylene glycol mono-n-butyl ether acetate, propylene glycol mono-i-butyl ether acetate, propylene glycol mono-sec-butyl ether acetate, and propylene glycol mono-t-butyl ether acetate; alkyl 2-hydroxypropionates such as methyl 2-hydroxypropionate, ethyl 2-hydroxypropionate, n-propyl 2-hydroxypropionate, i-propyl 2-hydroxypropionate, n-butyl 2-hydroxypropionate, i-butyl 2-hydroxypropionate, sec-butyl 2-hydroxypropionate, and t-butyl 2-hydroxypropionate; alkyl 3-alkoxypropionates such as methyl 3-methoxypropionate, ethyl 3-methoxypropionate, methyl 3-ethoxypropionate, and ethyl 3-ethoxypropionate; alcohols such as n-propylalcohol, i-propylalcohol, n-butylalcohol, t-butylalcohol, 1-octanol, 1-nonanol, benzyl alcohol, cyclohexanol, ethylene glycol monomethyl ether, ethylene glycol monoethyl ether, ethylene glycol mono-n-propyl ether, ethylene glycol mono-n-butyl ether, propylene glycol monomethyl ether, propylene glycol monoethyl ether, and propylene glycol mono-n-propyl ether; dialkylene glycol dialkyl ethers such as diethylene glycol dimethyl ether, diethylene glycol diethyl ether, diethylene glycol di-n-propyl ether, diethylene glycol di-n-butyl ether; ethylene glycol monoalkyl ether acetates such as ethylene glycol monomethyl ether acetate, ethylene glycol monoethyl ether acetate, and ethylene glycol mono-n-propyl ether acetate; other esters such as ethyl 2-hydroxy-2-methylpropionate, ethyl ethoxyacetate, ethyl hydroxyacetate, methyl 2-hydroxy-3-methylbutyrate, 3-methoxybutylacetate, 3-methyl-3-methoxybutylacetate, 3-methyl-3-methoxybutylpropionate, 3-methyl-3-methoxybutyrate, ethyl acetate, n-propyl acetate, n-butyl acetate, methyl acetoacetate, ethyl acetoacetate, methyl pyruvate, ethyl pyruvate; N-methylpyrrolidone, N,N-dimethylformamide, N,N-dimethylacetamide, diethylene glycol monomethyl ether, diethylene glycol monoethyl ether, caproic acid, caprylic acid, benzyl acetate, ethyl benzoate, diethyl oxalate, diethyl maleate, γ-butyrolactone, ethylene carbonate, propylene carbonate; and the like.

These solvents may be used either individually or in combination of two or more.

These solvents are usually used in the amount of 2,000 parts by weight or less for 100 parts by weight of the hydrosilane compound.

The hydrosilyl-forming reaction is preferably carried out in the absence of a solvent or in the presence of a solvent such as toluene, xylene, n-hexane, tetrahydrofuran, dichloromethane, or the like.

The hydrosilyl-forming reaction is also preferably carried out in a nitrogen or argon stream and under anhydrous conditions.

The hydrosilyl-forming reaction is carried out at a temperature of usually −50 to 300° C., and preferably 0 to 200° C. for usually five minutes to 1,000 hours.

Although a common hydrosilyl-forming reaction is thought to be preferably carried out usually under normal pressure or under pressure, the hydrosilyl-forming reaction for synthesizing the silicon-containing alicyclic compound (2) or silicon-containing alicyclic compound (4) can be carried out at a pressure less than the normal pressure, without requiring a special reaction vessel. This is an advantage of this reaction.

In this hydrosilyl-forming reaction, the compounds in which the silicon atom, shown in formulas (2-A), (2-B), (4-A), or (4-B), binds at the 2 or 3 position of the uppermost bicyclo[2.2.1]heptane ring are produced at the same time. The mixture can be used as is as a raw material for producing the polysiloxane (3) and polysiloxane (5), for example. As required, the two compounds may be separated by a suitable means such as distillation, recrystallization, liquid chromatography, gas chromatography, and the like.

The compound (2) of the above formula (2-B) or (4-B) can be synthesized by a conventional condensation reaction of a compound derived from the compound having the total number of the group $R^1$ as a halogen atom and the group —$OR^3$ in the formula (2-A) or (4-A) of two or three, by introducing a silanol group by hydrolyzing the halogen atom or at least part of the group —$OR^3$, in the presence of an acid catalyst or alkaline catalyst.

The silicon-containing alicyclic compound (4) in which Z is a monovalent organic group dissociating hydrogen atoms by the action of an acid can be synthesized from the silicon-containing alicyclic compound (4) in which Z is a hydrogen atom by replacing the hydrogen atom of the hydroxyl group of this compound with a monovalent organic group dissociating hydrogen atoms by the action of an acid.

More particularly, the above method can be carried out as follows, for example.

②  When Z is a t-butoxycarbonyl group, a method of esterifying the hydroxyl group in the raw material with di-t-butyl carbonate in the presence of a catalytic amount of 4-dimethylaminopyridine.

③  When Z is a tetrahydropyranyl group, a method of effecting an addition reaction to the hydroxyl group in the raw material with 2,3-dihydro-4H-pyrane according to a conventional method.

④  When Z is an acetal group such as a 1-alkoxyethyl group, a method of effecting an addition reaction to the hydroxyl group in the raw material with a corresponding alkylvinyl ether according to a conventional method.

The above methods ② to ④ can be carried out either using a suitable solvent or without using a solvent. The solvents previously given in the description relating to the method ① can be given as examples of the solvent used here. The reaction conditions, such as a reaction temperature and reaction time, are appropriately determined according to the method employed, types of reagents used, and the like.

In particular, the method ② can efficiently produce the silicon-containing alicyclic compound (4) in which the group Z is a monovalent organic group dissociating hydrogen atoms by the action of an acid. On the other hand, it is difficult to obtain the target compound by using a sodium hydride catalyst which is used to replace a hydroxyl group in common organic compounds with a t-butoxycarbonyl group.

Preparation of Polysiloxane (1)

Polysiloxane (1) can be prepared by a method comprising a step of polycondensing at least one component selected from the group consisting of a compound shown by the above-described formula (6) (hereinafter referred to as "silane compound (6)") or a linear of cyclic oligomer prepared by partial condensation of the silane compound (6) and/or at least one component selected from the group consisting of a compound shown by the above-described formula (7) (hereinafter referred to as "silane compound (7)") or a linear of cyclic oligomer prepared by partial condensation of the silane compound (7), and at least one component selected from the group consisting of a compound shown by the above-described formula (8) (hereinafter referred to as "silane compound (8)") or a linear of cyclic oligomer prepared by partial condensation of the silane compound (8) in the presence of an acidic catalyst, according to a conventional method, using or without using a solvent, in the presence of an acidic catalyst or a basic catalyst. The process preferably includes a polycondensation reaction step using an acidic catalyst.

Here, "the linear of cyclic oligomer prepared by partial condensation of the silane compound (6)", "the linear of cyclic oligomer prepared by partial condensation of the silane compound (7)", and "the linear of cyclic oligomer prepared by partial condensation of the silane compound (8)" denote oligomers of usually 2–10 molecules, preferably 2–5 molecules, in the case of linear oligomers, and usually 3–10 molecules, preferably 3–5 molecules, in the case of the cyclic oligomers, each oligomer being formed by the condensation of the Si—$OR^3$ groups in the silane compounds.

In the formula (6), $A^1$ is the same as defined for the above formula (1). As examples of the monovalent hydrocarbon group having 1–20 carbon atoms and monovalent halogenated hydrocarbon group having 1–20 carbon atoms represented by $R^3$, the corresponding groups previously mentioned in connection with the group $R^1$ in the structural unit (II) of the polysiloxane (1) can be given. As the group represented by the formula (i), the groups corresponding to $R^3$ of the silicon-containing alicyclic compound (2) can be given, for example.

In the formula (7), $A^2$ and $R^1$ are respectively the same as those defined in the above formula (1).

As examples of the monovalent hydrocarbon group having 1–20 carbon atoms and monovalent halogenated hydrocarbon group having 1–20 carbon atoms represented by $R^3$, the corresponding groups previously mentioned in connection with the group $R^1$ in the structural unit (II) of the polysiloxane (1) can be given. As the group represented by the formula (i), the groups corresponding to $R^3$ of the silicon-containing alicyclic compound (2) can be given, for example.

In the formula (8), $R^2$ is the same as defined for the above formula (1). As examples of the monovalent hydrocarbon group having 1–20 carbon atoms and monovalent halogenated hydrocarbon group having 1–20 carbon atoms represented by $R^3$, the corresponding groups previously mentioned in connection with the group $R^1$ in the structural unit (II) of the polysiloxane (1) can be given. As the group represented by the formula (i), the groups corresponding to $R^3$ of the silicon-containing alicyclic compound (2) can be given, for example.

In the formulas (6) to (8), given as examples of preferable monovalent hydrocarbon groups having 1–20 carbon atoms represented by $R^3$ are a methyl group, ethyl group, n-propyl group, i-propyl group, and the like; and as examples of preferable halogenated hydrocarbon groups having 1–20 carbon atoms represented by $R^3$ are a trifluoromethyl group, pentafluoroethyl group, 3,3,3,2,2-pentafluoro-n-propyl group, pentafluorophenyl group, o-fluorophenyl group, m-fluorophenyl group, p-fluorophenyl group, 2,3-difluorophenyl group, 2,4-difluorophenyl group, 2,5-difluorophenyl group, 2,6-difluorophenyl group, 3,4-difluorophenyl group, 3,5-difluorophenyl group, 2,3,4-trifluorophenyl group, 2,3,5-trifluorophenyl group, 2,3,6-trifluorophenyl group, 2,4,6-trifluorophenyl group, 3,4,5-trifluorophenyl group, a group of the formula (ii) in which 5 Rf's are fluorine atoms and b is 1, a group of the formula (ii) in which 5 Rf's are fluorine atoms and b is 2, and the like.

As examples of the linear, branched, or cyclic alkoxyl groups having 1–20 carbon atoms represented by X in the formula (i), which represents the group $R^3$, a methoxy group, ethoxy group, n-propoxygroup, i-propoxygroup, n-butoxygroup, i-butoxy group, sec-butoxy group, t-butoxy group, cyclopentyloxy group, cyclohexyloxy group, and the like can be given. Particularly preferable groups are a methyl group, phenyl group, methoxy group, and the like. a is preferably an integer of 1–5.

Particularly preferable groups represented by $R^3$ in the formulas (6), (7), and (8) are a methyl group, ethyl group, t-butyl group, trimethylsilyl group, and the like.

In preparing the polysiloxane (1), the silane compounds (6), (7), and (8) may be used either individually or in combination of two or more.

As examples of the inorganic acids among the above-mentioned acidic catalysts, hydrochloric acid, sulfuric acid, nitric acid, boric acid, phosphoric acid, titanium tetrachloride, zinc chloride, and aluminum chloride can be given. As examples of organic acids, formic acid, acetic acid, n-propionic acid, butyric acid, valeric acid, oxalic acid, malonic acid, succinic acid, maleic acid, fumaric acid, adipic acid, phthalic acid, terephthalic acid, acetic anhydride, maleic anhydride, citric acid, benzenesulfonic acid, p-toluenesulfonic acid, and methanesulfonic acid can be given.

Of these acidic catalysts, hydrochloric acid, sulfuric acid, acetic acid, oxalic acid, malonic acid, maleic acid, fumaric acid, acetic anhydride, and maleic anhydride are particularly preferable.

These acidic catalysts may be used either individually or in combination of two or more.

The acidic catalysts are usually used in the amount of 0.01–10,000 parts by weight, preferably 0.1~10, for 100 parts by weight of the silane compound.

As examples of inorganic bases among the above basic catalysts, lithium hydroxide, sodium hydroxide, potassium hydroxide, calcium hydroxide, barium hydroxide, sodium hydrogencarbonate, potassium hydrogencarbonate, sodium carbonate, and potassium carbonate can be given.

The following compounds can be given as examples of organic bases: linear, branched, or cyclic monoalkylamines such as n-hexylamine, n-heptylamine, n-octylamine, n-nonyamine, n-decylamine, and cyclohexylamine; linear, branched, or cyclic dialkylamines such as di-n-butylamine, di-n-pentylamine, di-n-hexylamine, di-n-heptylamine, di-n-octylamine, di-n-nonylamine, di-n-decylamine, cyclohexylmethylamine, and dicyclohexylamine; linear, branched, or cyclic trialkylamines such as triethylamine, tri-n-propylamine, tri-n-butylamine, tri-n-pentylamine, tri-n-hexylamine, tri-n-heptylamine, tri-N-octylamine, tri-n-nonylamine, tri-n-decylamine, cyclohexyldimethylamine, dicyclohexylmethylamine, and tricyclohexylamine; aromatic amines such as aniline, N-methylaniline, N,N-dimethylaniline, 2-methylaniline, 3-methylaniline, 4-methylaniline, 4-nitroaniline, diphenylamine, triphenylamine, and naphthylamine; aromatic diamines such as N,N,N',N'-tetramethylethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, 2,2-bis (4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, and 1,3-bis[1-(4-aminophenyl)-1-methylethyl]benzene; imidazoles such as imidazole, benzimidazole, 4-methylimidazole, and 4-methyl-2-phenylimidazole; pyridines such as pyridine, 2-methylpyridine, 4-methylpyridine, 2-ethylpyridine, 4-ethylpyridine, 2-phenylpyridine, 4-phenylpyridine, 2-methyl-4-phenylpyridine, nicotine, nicotinic acid, nicotinamide, quinoline, 8-oxyquinoline, and acridine; piperazines such as piperazine and 1-(2-hydroxyethyl) piperazine; as well as other nitrogen-containing heterocyclic compounds such as pyrazine, pyrazole, pyridazine, quinoxaline, purine, pyrrolidine, piperidine, morpholine, 4-methylmorpholine, 1,4-dimethylpiperazine, and 1,4-diazabicyclo[2.2.2]octane.

Of these basic catalysts, triethylamine, tri-n-propylamine, tri-n-butylamine, pyridine, and the like are preferable.

These basic catalysts may be used either individually or in combination of two or more. The basic catalysts are usually used in the amount of 0.01–10,000 parts by weight, preferably 0.1~10, for 100 parts by weight of the silane compound.

The use of an acidic catalyst in the preparation of polysiloxane (1) ensures a uniform and rapid polycondensation reaction accompanying hydrolysis, reducing the amount of hydrolysable groups in the raw material left unreacted in the resulting polymer, thereby minimizing absorption of radiation by the hydrolysable groups. Therefore, polycondensation under acidic conditions is more advantageous than polycondensation under basic conditions also with regard to the radiation transmittance in the wavelength range less than 193 nm.

Another advantage of carrying out the polycondensation under acidic conditions is that the resulting polysiloxane (1) has a narrow molecular weight distribution. The radiation-sensitive resin composition prepared from such a polysiloxane (1) is less susceptible to a negative-tone reaction when exposed to radiation having a wavelength less than the deep ultraviolet region, whereby the resin composition exhibits improved adhesion properties to resist pattern substrates. Furthermore, resist patterns with a fine and excellent configuration can be obtained also in the case where the resist is developed using a common developer due to homogeneous dissolution of resist films. This is a feature manifestly observed when the resist is exposed to radiation with a wavelength of 193 nm or less.

Moreover, the polycondensation of a raw material silane compound under acidic conditions, followed by the addition of a basic catalyst to continue the reaction under basic conditions increases the degree of polymerization of the resulting polysiloxane (1). Such a polysiloxane has a higher Tg and exhibits more excellent characteristics as a result of increased crosslinking. However, when the polysiloxane (1) is used as a material for the radiation-sensitive resin composition, which is discussed later in this specification, it should be noted that the problem as to which type of polysiloxane (1), i.e. the polysiloxane (1) obtained only by the polycondensation under acidic conditions and the polysiloxane (1) obtained by the polycondensation under acidic conditions followed by basic conditions is preferred depends on the type of the radiation-sensitive resin composition.

The polycondensation reaction under acidic conditions or basic conditions is preferably carried out in an inert gas atmosphere such as nitrogen or argon, whereby an advantage of a resist less susceptible to a negative-tone reaction can be ensured when forming a resist pattern using the radiation-sensitive resin composition.

The following solvents can be given as the solvent used in the polycondensation reaction: linear or branched ketones such as 2-butanone, 2-pentanone, 3-methyl-2-butanone, 2-hexanone, 4-methyl-2-pentanone, 3-methyl-2-pentanone, 3,3-dimethyl-2-butanone, 2-heptanone, and 2-octanone; cyclic ketones such as cyclopentanone, 3-methylcyclopentanone, cyclohexanone, 2-methylcyclohexanone, 2,6-dimethylcyclohexanone, and isophorone; propylene glycol monoalkyl ether acetates such as propylene glycol monomethyl ether acetate, propylene glycol monoethyl ether acetate, propylene glycol mono-n-propyl ether acetate, propylene glycol mono-i-propyl ether acetate, propylene glycol mono-n-butyl ether acetate, propylene glycol mono-i-butyl ether acetate, propylene glycol mono-sec-butyl ether acetate, and propylene glycol mono-t-butyl ether acetate; alkyl 2-hydroxypropionates such as methyl 2-hydroxypropionate, ethyl 2-hydroxypropionate, n-propyl-2-hydroxypropionate, i-propyl 2-hydroxypropionate, n-butyl 2-hydroxypropionate, i-butyl 2-hydroxypropionate, sec-butyl 2-hydroxypropionate, and t-butyl 2-hydroxypropionate; alkyl 3-alkoxypropionates such as methyl 3-methoxypropionate, ethyl 3-methoxypropionate, methyl 3-ethoxypropionate, and ethyl 3-ethoxypropionate; alcohols such as n-propylalcohol, i-propylalcohol, n-butylalcohol, t-butylalcohol, cyclohexanol, ethylene glycol monomethyl ether, ethylene glycol monoethyl ether, ethylene glycol mono-n-propyl ether, ethylene glycol mono-n-butyl ether, propylene glycol monomethyl ether, propylene glycol monoethyl ether, and propylene glycol mono-n-propyl ether; dialkylene glycol dialkyl ethers such as diethylene glycol dimethyl ether, diethylene glycol diethyl ether, diethylene glycol di-n-propyl ether, diethylene glycol di-n-butyl ether; ethylene glycol monoalkyl ether acetates such as ethylene glycol monomethyl ether acetate, ethylene glycol monoethyl ether acetate, and ethylene glycol mono-n-propyl ether acetate; aromatic hydrocarbons such as toluene and xylene; other esters such as ethyl 2-hydroxy-2-methylpropionate, ethyl ethoxyacetate, ethyl hydroxyacetate, methyl 2-hydroxy-3-methylbutyrate, butyl 3-methoxyacetate, butyl 3-methyl-3-methoxyacetate, butyl 3-methyl-3-methoxypropionate, butyl 3-methyl-3-methoxybutyrate, ethyl acetate, n-propyl acetate, n-butyl acetate, methyl acetoacetate, ethyl acetoacetate, methyl pyruvate, ethyl pyruvate; N-methylpyrrolidone, N,N-dimethylformamide, N,N-dimethylacetamide, benzyl ethyl ether, di-n-hexyl ether, diethylene glycol monomethyl ether, diethylene glycol monoethyl ether, caproic acid, caprylic acid, 1-octanol, 1-nonanol, benzylalcohol, benzyl acetate, ethyl benzoate, diethyl oxalate, diethyl maleate, γ-butyrolactone, ethylene carbonate, propylene carbonate; and the like.

These solvents may be used either individually or in combination of two or more.

These solvents are usually used in the amount of 2,000 parts by weight or less for 100 parts by weight of all of the silane compounds.

In addition, water may be added to the reaction mixture of the polycondensation reaction. The amount of water to be added is usually 10,000 parts by weight or less for 100 parts by weight of all of the silane compounds.

Furthermore, hexamethyldisiloxane may be added to the reaction mixture of the polycondensation reaction to control the molecular weight of the polysiloxane (1) and to increase stability.

The amount of hexamethyldisiloxane added is usually 500 parts by weight or less, and preferably 50 parts by weight or less, for 100 parts by weight of all of the silane compounds. If the amount of hexamethyldisiloxane exceeds 500 parts by weight, the resulting polymer tens to have a small molecular weight and a low glass transition temperature (Tg).

The polycondensation reaction is carried out at a temperature of usually −50 to 300° C., and preferably 20 to 100° C., usually for a period of one minute to 100 hours.

In preparing the polysiloxane (1), one or more other silane compounds may be used together with the above-described silane compounds (6), (7), and (8), or their partial condensates.

As examples of the other silane compounds, a silane compound of the following formula (12) (hereinafter referred to as "silane compound (12)"), a silane compound of the following formula (13) (hereinafter referred to as "silane compound (13)"), a silane compound of the following formula (14) (hereinafter referred to as "silane compound (14)"), and partial condensates of these silane compounds can be given.

"Partial condensate" herein indicates a linear oligomer formed from 2–10, preferably 2–5, silane molecules, or a cyclic oligomer formed from 3–10, preferably 3–5, silane molecules.

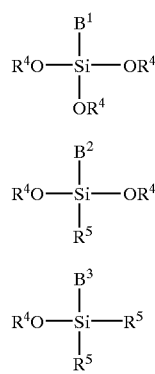

In the formulas (12)–(14), $B^1$, $B^2$, and $B^3$ individually represent a hydrogen atom, hydroxyl group, halogen atom, a substituted or unsubstituted alkyl group having 1–10 carbon atoms, a substituted or unsubstituted alkoxyl group having 1–10 carbon atoms, a substituted or unsubstituted acetoxy group, substituted or unsubstituted aryl group having 6–15 carbon atoms, substituted or unsubstituted aralkyl group having 7–20 carbon atoms, or other monovalent organic groups having an oxygen atom; and $R^4$ and $R^5$ individually represent an alkyl group having 1–10 carbon atoms or halogenated alkyl group having 1–10 carbon atoms; provided that $B^1$, $B^2$, and $B^3$ do not include $A^1$ in the formula (6) nor $A^2$ in the formula (7).

As examples of the halogen atom shown by $B^1$, $B^2$, and $B^3$ in the formulas (12) to (14), chlorine atom, bromine atom, and iodine atom can be given.

The following groups can be given as examples of the substituted or unsubstituted alkyl group having 1–10 carbon atoms represented by the group $B^1$, $B^2$, or $B^3$: methyl group, ethyl group, n-propyl group, i-propyl group, n-butyl group, i-butyl group, sec-butyl group, t-butyl group, n-pentyl group, n-hexyl group, n-heptyl group, n-octyl group, n-nonyl group, n-decyl group, cyclopentyl group, cyclohexyl group, hydroxymethyl group, 2-hydroxyethyl group, 3-hydroxypropyl group, 4-hydroxybutyl group, 4-hydroxycyclohexyl group, carboxymethyl group, 2-carboxyethyl group, 3-carboxypropyl group, 4-carboxybutyl group, 4-carboxycyclohexyl group, methoxymethyl group, 2-methoxyethyl group, 3-methoxypropyl group, 4-methoxybutyl group, 4-methoxycyclohexyl group, acetoxymethyl group, 2-acetoxyethyl group, 3-acetoxypropyl group, 4-acetoxybutyl group, 4-acetoxycyclohexyl group, mercaptomethyl group, 2-mercaptoethyl group, 3-mercaptopropyl group, 4-mercaptobutyl group, 4-mercaptocyclohexyl group, cyanomethyl group, 2-cyanoethyl group, 3-cyanopropyl group, 4-cyanobutyl group, 4-cyanocyclohexyl group, 3-glycidoxypropyl group, 2-(3,4-epoxy)cyclohexyl group, 2-(3,4-epoxy)cyclohexylethyl group, and 3-morpholinopropyl group.

As examples of the substituted or unsubstituted alkoxyl group having 1–10 carbon atoms represented by $B^1$, $B^2$, or $B^3$, methoxy group, ethoxy group, n-propoxy group, i-propoxy group, n-butoxy group, i-butoxy group, sec-butoxy group, t-butoxy group, cyclohexyloxy group, fluoromethoxy group, chloromethoxy group, 2-chloroethoxy group, 2-bromoethoxy group, 3-chloropropoxy group, 3-bromopropoxy group, 3-glycidoxypropoxy group, 4-fluorocyclohexyloxy group, and 3,4-epoxycyclohexyloxy group can be given.

As examples of the substituted or unsubstituted aceoxy group represented by $B^1$, $B^2$, or $B^3$, acetoxy group, trifluoroacetoxy group, chloroacetoxy group, and bromoacetoxy group can be given.

As examples of the as substituted or unsubstituted aryl group having 6–15 carbon atoms represented by $B^1$, $B^2$, or $B^3$, phenyl group, o-tolyl group, m-tolyl group, p-tolyl group, α-naphthyl group, β-naphthyl group, 2-fluorophenyl group, 3-fluorophenyl group, 4-fluorophenyl group, 4-chlorophenyl group, 4-bromophenyl group, 2-hydroxyphenyl group, 3-hydroxyphenyl group, 4-hydroxyphenyl group, 2-carboxyphenyl group, 3-carboxyphenyl group, 4-carboxyphenyl group, 2-methoxyphenyl group, 3-methoxyphenyl group, 4-methoxyphenyl group, 2-acetoxyphenyl group, 3-acetoxyphenyl group, 4-acetoxyphenyl group, 2-trimethylsiloxphenyl group, 3-trimethylsiloxyphenyl group, and 4-trimethylsiloxyphenyl group can be given.

As examples of the as substituted or unsubstituted aralkyl group having 7–20 carbon atoms represented by $B^1$, $B^2$, or $B^3$, benzyl group, phenethyl group, 2-fluorobenzyl group, 3-fluorobenzyl group, 4-fluorobenzyl group, 4-chlorobenzyl group, 4-bromobenzyl group, 2-hydroxybenzyl group, 3-hydroxybenzyl group, 4-hydroxybenzyl group, 2-methoxybenzyl group, 3-methoxybenzyl group, 4-methoxybenzyl group, 2-acetoxybenzyl group, 3-acetoxybenzyl group, 4-acetoxybenzyl group, 2-trimethylsiloxybenzyl group, 3-trimethylsiloxybenzyl group, and 4-trimethylsiloxybenzyl group can be given.

As examples of the other oxygen-containing monovalent groups represented by $B^1$, $B^2$, and $B^3$, the groups shown by the formulas (15) and (16) can be given:

$$-P'-OH \qquad (15)$$

$$-P'-COOH \qquad (16)$$

wherein P' indicates a methylene group, difluoromethylene group, fluoroalkylene group having 2–20 carbon atoms, divalent aromatic group having 6–20 carbon atoms, or other divalent alicyclic groups having 3–20 carbon atoms.

As examples of the fluoroalkylene groups having 2–20 carbon atoms, divalent aromatic groups having 6–20 carbon atoms, and other divalent alicyclic groups having 3–20 carbon atoms represented by P' in the formulas (15) and (16), the same corresponding groups previously given as examples of the group P in the formula (9) can be given.

As the group P' in the formulas (15) and (16), a difluoromethylene group, a divalent hydrocarbon group having an adamantine skeleton, its halide derivative, a divalent hydrocarbon group having a norbornene skeleton, its halide derivative, and the like are preferable. The group represented by the following formula (17) is particularly preferable:

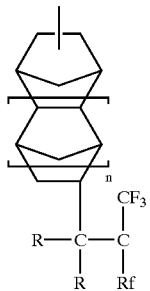

(17)

wherein R individually represents a hydrogen atom or a methyl group, Rf represents a hydrogen atom, methyl group, or trifluoromethyl group, and n is an integer of 0–3.

As examples of the alkyl group or halogenated alkyl groups having 1–10 carbon atoms represented by $R^4$ or $R^5$ in the formulas (12) to (14), a methyl group, ethyl group, n-propyl group, i-propyl group, n-butyl group, i-butyl group, sec-butyl group, t-butyl group, n-pentyl group, n-hexyl group, n-heptyl group, n-octyl group, n-nonyl group, n-decyl group, cyclopentyl group, cyclohexyl group, fluoromethyl group, chloromethyl group, bromomethyl group, difluoromethyl group, dichloromethyl group, and trifluoromethyl group can be given.

If at least one compound selected from the group consisting of the silane compounds (12)–(14) and their partial condensates is condensed together with the silane compound (6) and/or silane compound (7), or their partial condensates, the molecular weight and glass transition temperature (Tg) of the resulting polysiloxane (1) can be adequately controlled so that transparency at the wavelength of 193 nm, particularly preferable 157 nm, can be further improved.

The total amount of the silane compound (12), silane compound (13), and silane compound (14) is usually 80 wt % or less, preferably ~50 wt %, and particularly preferably ~wt %, for 100 wt % of all silane compounds. If this total amount exceeds 80 wt %, resolution of the resulting radiation-sensitive resin composition tends to be impaired.

Preparation of Polysiloxane (3)

Polysiloxane (3) can be prepared by the polycondensation of at least one component selected from the group consisting of the silicon-containing alicyclic compound (2) having m=0 or 1 and n=1–3 in the formula (2-A) (hereinafter referred to as "silicon-containing alicyclic compound (2')") and a linear or cyclic oligomer prepared by partial condensation of the silicon-containing alicyclic compound (2'), in the presence of an acidic catalyst or a basic catalyst using or without using a solvent in the same manner as in the case of polysiloxane (1). The process preferably includes a polycondensation reaction step using an acidic catalyst.

Here, "the linear of cyclic oligomer prepared by partial condensation of the silicon-containing alicyclic compound (2')" indicates oligomers of usually 2–10 molecules, preferably 2–5 molecules, in the case of linear oligomers, and usually 3–10 molecules, preferably 3–5 molecules, in the case of the cyclic oligomers, each oligomer being formed by the condensation of the Si—$OR^3$ groups in the silicon-containing alicyclic compounds.

In preparing the polysiloxane (3), silicon containing alicyclic compound (2') may be used either individually or in combination of two or more.

The use of an acidic catalyst in the preparation of polysiloxane (3) ensures a uniform and rapid polycondensation reaction accompanying hydrolysis, reducing the amount of hydrolysable groups in the raw material left unreacted in the resulting polymer, thereby minimizing absorption of radiation by the hydrolysable groups. Therefore, polycondensation under acidic conditions is more advantageous than polycondensation under basic conditions also with regard to the radiation transmittance in the wavelength range less than 193 nm.

Another advantage of carrying out the polycondensation under acidic conditions is that the resulting polysiloxane (3) has a narrow molecular weight distribution. The radiation-sensitive resin composition prepared from such a polysiloxane (3) is less susceptible to a negative-tone reaction when exposed to radiation having a wavelength less than the deep ultraviolet region, whereby the resin composition exhibits improved adhesion properties to resist pattern substrates. Furthermore, resist patterns with a fine and excellent configuration can be obtained also in the case where the resist is developed using a common developer due to homogeneous dissolution of resist films. This is a feature manifestly observed when the resist is exposed to radiation with a wavelength of 193 nm or less.

Moreover, in the preparation of polysiloxane (3), the polycondensation of a raw material compound under acidic conditions, followed by the addition of a basic catalyst to continue the reaction under acidic conditions increases the degree of polymerization of the resulting polysiloxane (3). Such a polysiloxane has a higher Tg and exhibits more excellent characteristics as a result of increased crosslinking. However, when the polysiloxane (3) is used as a material for the radiation-sensitive resin composition, which is discussed later in this specification, it should be noted that the problem as to which type of polysiloxane (3), i.e. the polysiloxane (3) obtained only by the polycondensation under acidic conditions and the polysiloxane (3) obtained by the polycondensation under acidic conditions followed by basic conditions is preferred depends on the type of the radiation-sensitive resin composition.

In preparing the polysiloxane (3), one or more other silane compounds may be used together with the silicon containing alicyclic compound (2') or their partial condensates.

As above-described other silane compounds, the silicon-containing alicyclic compound (2) having m=0 or 1 and n=0 in the formula (2-A), silicon-containing alicyclic compound (2) having m=2 in the formula (2-A), silicon-containing alicyclic compound (4), silane compound (8), silane compound (12), silane compound (13), and silane compound (14), and their partial condensates can be given.

Use of these other silane compounds, particularly the silane compound (12) or its partial condensates, in the polycondensation reaction ensures adequate control of the molecular weight and glass transition temperature (Tg) of the resulting polysiloxane (3), whereby transparency at the wavelength of 193 nm, particularly preferable 157 nm, can be further improved. The total amount of the other silane compounds is usually 80 wt % or less, preferably 50 wt % or less, and particularly preferably 20 wt % or less of the total amount of the silicon-containing alicyclic compound (2') and the other silane compounds. If this total amount exceeds 80 wt %, resolution of the resulting radiation-sensitive resin composition tends to be impaired.

Preparation of Polysiloxane (5)

Polysiloxane (5) can be prepared by the polycondensation of at least one component selected from the group consisting of the silicon-containing alicyclic compound (4) having m=0 or 1 in the formula (4-A) (hereinafter referred to as "silicon-containing alicyclic compound (4')") and a linear or cyclic oligomer prepared by partial condensation of the silicon-containing alicyclic compound (2'), in the presence of an acidic catalyst or a basic catalyst using or without using a solvent in the same manner as in the case of polysiloxane (1). The process preferably includes a polycondensation reaction step using an acidic catalyst.

Here, "the linear of cyclic oligomer prepared by partial condensation of the silicon-containing alicyclic compound (4')" indicates oligomers of usually 2–10 molecules, preferably 2–5 molecules, in the case of linear oligomers, and usually 3–10 molecules, preferably 3–5 molecules, in the case of the cyclic oligomers, each oligomer being formed by the condensation of the Si—OR$^3$ groups in the silicon-containing alicyclic compounds.

In preparing the polysiloxane (5), silicon containing alicyclic compound (4') may be used either individually or in combination of two or more.

The use of an acidic catalyst in the preparation of polysiloxane (5) ensures a uniform and rapid polycondensation reaction accompanying hydrolysis, reducing the amount of hydrolysable groups in the raw material left unreacted in the resulting polymer, thereby minimizing absorption of radiation by the hydrolysable groups. Therefore, polycondensation under acidic conditions is more advantageous than polycondensation under basic conditions also with regard to the radiation transmittance in the wavelength range less than 193 nm.

Another advantage of carrying out the polycondensation under acidic conditions is that the resulting polysiloxane (5) has a narrow molecular weight distribution. The radiation-sensitive resin composition prepared from such a polysiloxane (5) is less susceptible to a negative-tone reaction when exposed to radiation having a wavelength less than the deep ultraviolet region, whereby the resin composition exhibits improved adhesion properties to resist pattern substrates. Furthermore, resist patterns with a fine and excellent configuration can be obtained also in the case where the resist is developed using a common developer due to homogeneous dissolution of resist films. This is a feature manifestly observed when the resist is exposed to radiation with a wavelength of 193 nm or less.

Moreover, in the preparation of polysiloxane (5), the polycondensation of a raw material compound under acidic conditions, followed by the addition of a basic catalyst to continue the reaction under acidic conditions increases the degree of polymerization of the resulting polysiloxane (5). Such a polysiloxane has a higher Tg and exhibits more excellent characteristics as a result of increased crosslinking. However, when the polysiloxane (5) is used as a material for the radiation-sensitive resin composition, which is discussed later in this specification, it should be noted that the problem as to which type of polysiloxane (5), i.e. the polysiloxane (5) obtained only by the polycondensation under acidic conditions and the polysiloxane (3) obtained by the polycondensation under acidic conditions followed by basic conditions is preferred depends on the type of the radiation-sensitive resin composition.

In preparing the polysiloxane (5), one or more other silane compounds may be used together with the silicon containing alicyclic compound (4') or their partial condensates.

As the above-described other silane compounds, the silicon-containing alicyclic compound (2), the silicon-containing alicyclic compound (4) having m=2 in the formula (4-A), silane compound (8), silane compound (12), silane compound (13), and silane compound (14), and their partial condensates can be given.

Use of these other silane compounds, particularly the silane compound (12) or its partial condensates, in the polycondensation reaction ensures adequate control of the molecular weight and glass transition temperature (Tg) of the resulting polysiloxane (5), whereby transparency at the wavelength of 193 nm, particularly preferable 157 nm, can be further improved. The total amount of the other silane compounds is usually 80 wt % or less, preferably 50 wt % or less and particularly preferably 20 wt % or less of the total amount of the silicon-containing alicyclic compound (4') and the other. silane compounds. If this total amount exceeds 80 wt %, resolution as a resist tends to be impaired.

The silicon-containing alicyclic compound (5) in which Z is a monovalent organic group dissociating hydrogen atoms by the action of an acid can be synthesized from polysiloxane (5) in which Z is a hydrogen atom by replacing the hydrogen atom of the hydroxyl group of this compound with a monovalent organic group dissociating hydrogen atoms by the action of an acid.

More particularly, the above method can be carried out as follows, for example.

⑤ When Z is a t-butoxycarbonyl group, a method of esterifying the hydroxyl group in the raw polymer with di-t-butyl carbonate in the presence of a catalytic amount of 4-dimethylaminopyridine.

⑥ When Z is a tetrahydropyranyl group, a method of effecting an addition reaction to the hydroxyl group in the raw polymer with 2,3-dihydro-4H-pyrane according to a conventional method.

⑦ When Z is an acetal group such as a 1-alkoxyethyl group, a method of effecting an addition reaction to the hydroxyl group in the raw polymer with a corresponding alkylvinyl ether according to a conventional method.

The above methods ⑤ to ⑦ can be carried out usually using a suitable solvent. The solvents previously given in the description relating to the method ① for the preparation of the silicon containing alicyclic compound (2) and silicon containing alicyclic compound (4) can be given as examples of the solvent used here. The reaction conditions, such as a reaction temperature and reaction time, are appropriately determined according to the method employed, types of reagents used, and the like.

In particular, the method ⑤ can efficiently produce the polysiloxane (4) in which the group Z is a monovalent organic group dissociating hydrogen atoms by the action of an acid. On the other hand, it is difficult to obtain the target compound by using a sodium hydride catalyst which is used to replace a hydroxyl group in common organic compounds with a t-butoxycarbonyl group.

Radiation-sensitive Resin Composition

The following compositions can be given as examples of the preferable radiation-sensitive resin composition of the present invention.

(1) A radiation-sensitive resin composition containing (a) a resin comprising an alkali insoluble or alkali low soluble polysiloxane (1), which becomes soluble in alkali when an acid-dissociable group dissociates, and (b) a photoacid generator (hereinafter referred to as "radiation-sensitive resin composition (1)").

(2) A radiation-sensitive resin composition containing (a) a resin comprising an alkali insoluble or alkali low soluble polysiloxane (3') and/or an alkali insoluble or alkali low soluble polysiloxane (5), which becomes soluble in alkali when an acid-dissociable group dissociates, and (b) a photoacid generator (hereinafter referred to as "radiation-sensitive resin composition (2)").

The component (a) in the radiation-sensitive resin composition (1) preferably comprises a polysiloxane which comprises at least one of the structural units (I-1) and (I-2) and/or a polysiloxane which comprises at least one of the structural units (II-1) and (II-2).

The polysiloxane (3') in the radiation-sensitive resin composition (3') comprises the structural unit (I-1') and/or the structural unit (I-2') and has a Mw of 500–1,000,000. The group shown by the following formula (iii) can be given as an example of the monovalent organic group dissociating hydrogen atoms by the action of an acid represented by Z' in the formula (3'):

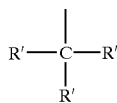

(iii)

wherein R' individually represents a linear or branched alkyl group having 1–4 carbon atoms or a monovalent alicyclic hydrocarbon group having 3–20 carbon atoms or a derivative thereof, or any two of R's form in combination a divalent alicyclic hydrocarbon group having 3–20 carbon atoms or a derivative thereof, with the remaining R' being a linear or branched alkyl group having 1–4 carbon atoms or a monovalent alicyclic hydrocarbon group having 3–20 carbon atoms or a derivative thereof.

As examples of the linear or branched alkyl group having 1–4 carbon atoms represented by R' in the formula (iii), a methyl group, ethyl group, n-propyl group, i-propyl group, n-butyl group, 2-methylpropyl group, 1-methylpropyl group, and t-butyl group can be given.

As examples of the monovalent alicyclic hydrocarbon group having 3–20 carbon atoms and the divalent alicyclic hydrocarbon group having 3–20 carbon atoms formed by two R's in combination, alicyclic groups derived from a cycloalkane such as norbornane, tricyclodecane, tetracyclododecane, adamantine, cyclopropane, cyclobutane, cyclopentane, cyclohexane, cycloheptane, or cyclooctane, and groups obtained by replacing hydrogen atoms on these alicyclic groups with above-mentioned one or more alkyl groups having 1–4 carbon atoms can be given.

Of these groups of the formula (iii), the group having a methyl group for R' (corresponding to the recurring unit forming the polysiloxane (3)) is ideal.

Acid Generator (b)

The acid generator (b) used in the radiation-sensitive resin composition (1) or the radiation-sensitive resin composition (2) is a component generating an acid by exposure to radiation. The acid causes an acid-dissociable group in the resin to dissociate. As a result, an exposed part of the resist film becomes readily soluble in an alkaline developer, thereby forming a positive-tone resist pattern.

As examples of the acid generator (b), onium salts, halogen-containing compounds, diazoketone compounds, sulfone compounds, and sulfonate compounds can be given.

Examples of the acid generator (b) are given below.
Onium Salts:

As examples of onium salts, iodonium salts, sulfonium salts (including tetrahydrothiophenium salts), phosphonium salts, diazonium salts, and pyridinium salts can be given.

Specific examples of preferable onium salts include: diphenyliodonium trifluoromethanesulfonate, diphenyliodonium nonafluoro-n-butanesulfonate, diphenyliodonium heptadecafluoro-n-octanesulfonate, diphenyliodonium pyrenesulfonate, diphenyliodonium n-dodecylbenzenesulfonate, diphenyliodonium hexafluoroantimonate, diphenyliodonium naphthalenesulfonate, bis(4-t-butylphenyl)iodonium trifluoromethanesulfonate, bis(4-t-butylphenyl)iodonium nonafluoro-n-butanesulfonate, bis(4-t-butylphenyl) iodonium heptadecafluoro-n-octanesulfonate, bis(4-t-butylphenyl)n-dodecylbenzenesulfonate, bis(4-t-butylphenyl)iodonium hexafluoroantimonate, bis(4-t-butylphenyl)iodonium naphthalenesulfonate, triphenylsulfonium trifluoromethanesulfonate, triphenylsulfonium nonafluoro-n-butanesulfonate, triphenylsulfonium heptadecafluoro-n-octanesulfonate, triphenylsulfonium pyrenesulfonate, triphenylsulfonium n-dodecylbenzenesulfonate, triphenylsulfonium hexafluoroantimonate, triphenylsulfonium naphthalenesulfonate, triphenylsulfonium 10-camphorsulfonate, 4-hydroxyphenyl.phenyl.methylsulfonium, p-toluenesulfonate, cyclohexyl.2-oxocyclohexyl.methylsulfonium trifluoromethanesulfonate, cyclohexyl.2-oxocyclohexyl.methylsulfonium nonafluoro-n-butanesulfonate, cyclohexyl.2-oxocyclohexyl.methylsulfonium heptadecafluoro-n-octanesulfonate, dicyclohexyl.2-oxocyclohexylsulfonium trifluoromethanesulfonate, dicyclohexyl.2-oxocyclohexylsulfonium nonafluoro-n-butanesulfonate, dicyclohexyl.2-oxocyclohexylsulfonium heptadecafluoro-n-octanesulfonate, 2-oxocyclohexyldimethylsulfonium trifluoromethanesulfonate, 2-oxocyclohexyldimethylsulfonium nonafluoro-n-butanesulfonate, 2-oxocyclohexyldimethylsulfonium heptadecafluoro-n-octanesulfonate, 4-hydroxyphenyl.benzyl.methylsulfonium p-toluenesulfonate, triphenylsulfonium perfluoro-n-octanesulfonate, 1-naphthyldimethylsulfonium trifluoromethanesulfonate, 1-naphthyldimethylsulfonium nonafluoro-n-butanesulfonate, 1-naphthyldimethylsulfonium heptadecafluoro-n-octanesulfonate, 1-naphthyldiethylsulfonium trifluoromethanesulfonate, 1-naphthyldiethylsulfonium nonafluoro-n-butanesulfonate, 1-naphthyldiethylsulfonium heptadecafluoro-n-octanesulfonate, 4-cyano-1-naphthyldimethylsulfonium trifluoromethanesulfonate, 4-cyano-1-naphthyldimethylsulfonium nonafluoro-n-butanesulfonate, 4-cyano-1-naphthyldimethylsulfonium heptadecafluoro-n-octanesulfonate, 4-cyano-1-naphthyldiethylsulfonium trifluoromethanesulfonate, 4-cyano-1-naphthyldiethylsulfonium nonafluoro-n-butanesulfonate, 4-cyano-1-naphthyldiethylsulfonium heptadecafluoro-n-octanesulfonate, 4-nitro-1-naphthyldimethylsulfonium trifluoromethanesulfonate, 4-nitro-1-naphthyldimethylsulfonium nonafluoro-n-butanesulfonate, 4-nitro-1-naphthyldimethylsulfonium heptadecafluoro-n-octanesulfonate, 4-nitro-1-naphthyldiethylsulfonium trifluoromethanesulfonate, 4-nitro-1-naphthyldiethylsulfonium nonafluoro-n-butanesulfonate, 4-nitro-1-naphthyldiethylsulfonium heptadecafluoro-n-octanesulfonate, 4-methyl-1-naphthyldimethylsulfonium trifluoromethanesulfonate, 4-methyl-1-naphthyldimethylsulfonium nonafluoro-n-butanesulfonate, 4-methyl-1-naphthyldimethylsulfonium heptadecafluoro-n-octanesulfonate, 4-methyl-1-naphthyldiethylsulfonium trifluoromethanesulfonate, 4-methyl-1-naphthyldiethylsulfonium nonafluoro-n-butanesulfonate, 4-methyl-1-naphthyldiethylsulfonium heptadecafluoro-n-octanesulfonate, 4-hydroxy-1-naphthyldimethylsulfonium trifluoromethanesulfonate, 4-hydroxy-1-naphthyldimethylsulfonium nonafluoro-n-butanesulfonate, 4-hydroxy-1-naphthyldimethylsulfonium heptadecafluoro-n-octanesulfonate, 4-hydroxy-1-naphthyldiethylsulfonium trifluoromethanesulfonate, 4-hydroxy-1-naphthyldiethylsulfonium nonafluoro-n-butanesulfonate, 4-hydroxy-1-naphthyldiethylsulfonium heptadecafluoro-n-octanesulfonate, 4-hydroxy-1-naphthyltetrahydrothiophenium trifluoromethanesulfonate, 4-methoxy-1-naphthyltetrahydrothiophenium trifluoromethanesulfonate, 4-ethoxy-1-naphthyltetrahydrothiophenium trifluoromethanesulfonate, 4-methoxymethoxy-1-naphthyltetrahydrothiophenium trifluoromethanesulfonate, 4-ethoxymethoxy-1-naphthyltetrahydrothiophenium trifluoromethanesulfonate, 4-(1'-methoxyethoxy)-1-naphthyltetrahydrothiophenium trifluoromethanesulfonate, 4-(2'-methoxyethoxy)-1-naphthyltetrahydrothiophenium trifluoromethanesulfonate, 4-methoxycarbonyloxy-1-naphthyltetrahydrothiophenium trifluoromethanesulfonate, 4-ethoxycarbonyloxy-1-naphthyltetrahydrothiophenium trifluoromethanesulfonate, 4-n-propoxycarbonyloxy-1-naphthyltetrahydrothiophenium trifluoromethanesulfonate, 4-i-propoxycarbonyloxy-1-naphthyltetrahydrothiophenium trifluoromethanesulfonate, 4-n-butoxycarbonyloxy-1-naphthyltetrahydrothiophenium trifluoromethanesulfonate, 4-t-butoxycarbonyloxy-1-naphthyltetrahydrothiophenium trifluoromethanesulfonate, 4-(2'-tetrahydrofuranyloxy)-1-naphthyltetrahydrothiophenium trifluoromethanesulfonate, 4-(2'-tetrahydropyranyloxy)-1-naphthyltetrahydrothiophenium trifluoromethane sulfonate, 4-benzyl oxy-1-naphthyltetrahydrothiophenium trifluoromethanesulfonate, 1-(1'-naphthylacetomethyltetrahydrothiophenium trifluoromethane sulfonate, 4-n-butoxy-1-naphthyltetrahydrothiophenium nonafluoro-n-butanesulfonate.

Halogen-containing Compounds

As examples of halogen-containing compounds, haloalkyl group-containing hydrocarbon compounds, haloalkyl group-containing heterocyclic compounds, and the like can be given.

As specific examples of preferable halogen-containing compounds, (trichloromethyl)-s-triazine derivatives such as phenylbis(trichloromethyl)-s-triazine, 4-methoxyphenylbis(trichloromethyl)-s-triazine, and 1-naphthylbis(trichloromethyl)-s-triazine, 1,1-bis(4'-chlorophenyl)-2,2,2-trichloroethane, and the like can be given.

Diazoketone Compounds:

As examples of diazoketone compounds, 1,3-diketo-2-diazo compounds, diazobenzoquinone compounds, diazonaphthoquinone compounds, and the like can be given.

As specific examples of preferable diazoketone compounds, 1,2-naphthoquinonediazido-4-sulfonyl chloride, 1,2-naphthoquinonediazido-5-sulfonyl chloride, 1,2-naphthoquinonediazido-4-sulfonate or 1,2-naphthoquinonediazido-5-sulfonate of 2,3,4,4'-tetrahydroxybenzophenone, 1,2-naphthoquinonediazido-4-sulfonate or 1,2-naphthoquinonediazido-5-sulfonate of 1,1,1-tris(4'-hydroxyphenyl)ethane, and the like can be given.

Sulfone Compounds:

As examples of sulfone compounds, β-ketosulfone, β-sulfonylsulfone, α-diazo compounds of these compounds, and the like can be given.

As specific examples of preferable sulfone compounds, 4-trisphenacylsulfone, mesitylphenacylsulfone, bis (phenylsulfonyl)methane, and the like can be given.

Sulfonate Compounds:

As examples of sulfonate compounds, alkyl sulfonate, alkylimide sulfonate, haloalkyl sulfonate, aryl sulfonate, imino sulfonate, and the like can be given.

As specific examples of sulfonate compounds, benzointosylate, pyrogallol tris(trifluoromethanesulfonate), nitrobenzyl-9,10-diethoxyanthracene-2-sulfonate, trifluoromethanesulfonylbicyclo[2.2.1]hept-5-ene-2,3-dicarbodiimide, N-hydroxysuccinimidetrifluoromethanesulfonate, and 1,8-naphthalenedicarboxylic acid imido trifluoromethanesulfonate can be given. Of the above acid generators (b), the following compounds are preferable: diphenyliodoniumtrifluoromethanesulfonate, bis(4-t-butylphenyl)iodonium trifluoromethanesulfonate, bis(4-t-butylphenyl)iodonium nonafluoro-n-butanesulfonate, triphenylsulfonium trifluoromethanesulfonate, triphenylsulfonium nonafluoro-n-butanesulfonate, cyclohexyl-2-oxocyclohexylmethylsulfonium trifluoromethane sulfonate, dicyclohexyl-2-oxocyclohexylsulfonium trifluoromethanesulfonate, 2-oxocyclohexyldimethylsulfoniuni trifluoromethanesulfonate, 4-hydroxy-1-naphthyldimethylsulfonium trifluorornethanesulfonate, 4-hydroxy-1-naphthyltetrahydrothiophenium trifluoromethanesulfonate, 1-(1'-naphthylacetomethyl)tetrahydrothiophenium trifluoromethanesulfonate, trifluoromethanesulfonylbicyclo[2.2.1]hept-5-ene-2,3-dicarbodiimide, N-hydroxysuccinimidetrifluoromethanesulfonate, 1,8-naphthalenedicarboxylic acid imido trifluoromethanesulfonate, and the like.

The acid generator (b) may be used either individually or in combination of two or more.

The amount of the acid generator (b) to be used in the radiation-sensitive resin composition (1) and radiation-sensitive resin composition (2) is usually 0.1–10 parts by weight, and preferably 0.5–7 parts by weight for 100 parts by weight of the resin from the viewpoint of ensuring sensitivity and developability as a resist. If the amount of the acid generator (b) is less than 0.1 part by weight, sensitivity and developability tend to decrease. If the amount exceeds 10 parts by weight, a rectangular resist pattern may not be obtained due to decreased radiation transmittance.

Additives

It is preferable to add an acid diffusion controller to the radiation-sensitive resin composition (1) and radiation-sensitive resin composition (2). The acid diffusion controller controls diffusion of an acid generated from the acid generator (b) upon exposure in the resist film to suppress unfavorable chemical reactions in the unexposed area.

The addition of such an acid diffusion controller improves storage stability of the resulting composition and resolution as a resist. Moreover, the addition of the acid diffusion controller prevents the line width of the resist pattern from changing due to changes in the post-exposure delay (PED) between exposure and development, whereby a composition with remarkably superior process stability can be obtained. As the acid diffusion controller, organic compounds containing nitrogen of which the basicity does not change during exposure or heating for forming a resist pattern are preferable.

As examples of such nitrogen-containing organic compounds, a compound shown by the following formula (18) (hereinafter called "nitrogen-containing compound ①"),

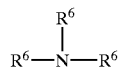

(18)

wherein $R^6$ individually represents a hydrogen atom, a substituted or unsubstituted alkyl group, substituted or unsubstituted aryl group, or substituted or unsubstituted aralkyl group, a compound having two nitrogen atoms in the molecule (hereinafter referred to as "nitrogen-containing compound ②"), a polymer having three or more nitrogen atoms in the molecule (hereinafter referred to as "nitrogen-containing compound ③"), an amide group-containing compound, urea compound, nitrogen-containing heterocyclic compound, and the like can be given.

The following compounds can be given as examples of the nitrogen-containing compound ①: linear, branched, or cyclic monoalkylamines such as n-hexylamine, n-heptylamine, n-octylamine, n-nonyamine, n-decylamine, and cyclohexylamine; linear, branched, or cyclic dialkylamines such as di-n-butylamine, di-n-pentylamine, di-n-hexylamine, di-n-heptylamine, di-n-octylamine, di-n-nonylamine, di-n-decylamine, cyclohexylmethylamine, and dicyclohexylamine; linear, branched, or cyclic trialkylamines such as triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, cyclohexyldimethylamine, dicyclohexylmethylamine, and tricyclohexylamine; aromatic amines such as aniline, N-methylaniline, N,N-dimethylaniline, 2-methylaniline, 3-methylaniline, 4-methylaniline, 4-nitroaniline, diphenylamine, triphenylamine, and naphthylamine; and the like.

Examples of the nitrogen-containing compound ② include ethylenediamine, N,N,N',N'-tetramethylethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, 2,2-bis(4'-aminophenyl)propane, 2-(3'-aminophenyl)-2-(4'-aminophenyl)propane, 2-(4'-aminophenyl)-2-(3'-hydroxyphenyl)propane, 2-(4'-aminophenyl)-2-(4'-hydroxyphenyl)propane, 1,4-bis[1'-(4"-aminophenyl)-1'-methylethyl]benzene, 1,3-bis[1'-(4"-aminophenyl)-1'-methylethyl]benzene, and the like.

Examples of the nitrogen-containing compounds ③ include polyethyleneimine, polyallylamine, a polymer of 2-dimethylaminoethylacrylamide, and the like.

Examples of compounds containing an amide group include formamide, N-methylformamide, N,N-dimethylformamide, acetamide, N-methylacetamide, N,N-dimethylacetamide, propionamide, benzamide, pyrrolidone, N-methylpyrrolidone, and the like.

Examples of the urea compounds include urea, methylurea, 1,1-dimethylurea, 1,3-dimethylurea, 1,1,3,3-tetramethylurea, 1,3-diphenylurea, tri-n-butylthiourea, and the like. Examples of the nitrogen-containing heterocyclic compounds include: imidazoles such as imidazole, benzimidazole, 4-methylimidazole, and 4-methyl-2-phenylimidazole; pyridines such as pyridine, 2-methylpyridine, 4-methylpyridine, 2-ethylpyridine, 4-ethylpyridine, 2-phenylpyridine, 4-phenylpyridine, 2-methyl-4-phenylpyridine, nicotine, nicotinic acid, nicotinamide, quinoline, 4-hydroxyquinoline, 8-oxyquinoline, and acridine; piperazines such as piperazine, 1-(2'-hydroxyethyl)piperazine; pyrazine, pyrazole, pyridazine, quinoxaline, purine, pyrrolidine, piperidine, morpholine, 4-methylmorpholine, 1,4-dimethylpiperazine, 1,4-diazabicyclo[2.2.2]octane; and the like.

Of these nitrogen-containing organic compounds, the nitrogen-containing organic compounds ① and the nitrogen-containing heterocyclic compounds are preferable. Among the nitrogen-containing organic compounds ①, tri(cyclo)alkylamines are particularly preferable. Among the nitrogen-containing heterocyclic compounds, pyridines and piperazines are particularly preferable.

The acid diffusion controller may be used either individually or in combination of two or more.

The amount of the acid diffusion controller to be added to the radiation-sensitive resin composition (1) or the radiation-sensitive resin composition (2) is usually 15 parts by weight or less, preferably 10 parts by weight or less, and still more preferably 5 parts by weight or less for 100 parts by weight of the resin. If the proportion of the acid diffusion controller exceeds 15 parts by weight, sensitivity as a resist and developability of the exposed area tend to decrease. If the amount is less than 0.001 part by weight, the pattern shape or dimensional accuracy as a resist may decrease depending on the processing conditions.

Surfactants which improve applicability, developability, or the like may be added to the radiation-sensitive resin composition (1) and the radiation-sensitive resin composition (2).

As examples of surfactants, nonionic surfactants such as polyoxyethylene lauryl ether, polyoxyethylene stearyl ether, polyoxyethylene oleyl ether, polyoxyethylene n-octyl phenyl ether, polyoxyethylene n-nonyl phenyl ether, polyethylene glycol dilaurate, polyethylene glycol distearate; commercially available products such as KP341 (manufactured by Shin-Etsu Chemical Co., Ltd.), Polyflow No. 75, No. 95 (manufactured by Kyoeisha Chemical Co., Ltd.), FTOP EF301, EF303, EF352 (manufactured by TOHKEM PRODUCTS CORPORATION), MEGAFAC F171, F173 (manufactured by Dainippon Ink and Chemicals, Inc.), Fluorard FC430, FC431 (manufactured by Sumitomo 3M Ltd.), Asahi Guard AG710, Surflon S-382, SC-101, SC-102, SC-103, SC-104, SC-105, SC-106 (manufactured by Asahi Glass Co., Ltd.); and the like can be given.

These surfactants may be used either individually or in combination of two or more.

The amount of the surfactant to be added to the radiation-sensitive resin composition (1) or the radiation-sensitive resin composition (2) is usually 2 parts by weight or less for 100 parts by weight of the total amount of resin and the acid generator (b).

As other additives, halation inhibitors, adhesion promoters, storage stabilizers, anti-foaming agents, and the like can be given.

The radiation-sensitive resin composition (1) and radiation-sensitive resin composition (2) excel in dry etching resistance and possess superior basic properties as a resist such as excellent transmittance, sensitivity, resolution, and developability.

Preparation of Composition Solution

The radiation-sensitive resin composition (1) and radiation-sensitive resin composition (2) can be prepared as a composition solution by dissolving the composition in a solvent so that the total solid content is 1–25 wt %, and preferably 2–15 wt %, and filtering the composition using a filter with a pore diameter of about 0.2 μm, for example.

Examples of solvents used for the preparation of the composition solution include: linear or branched ketones such as 2-butanone, 2-pentanone, 3-methyl-2-butanone, 2-hexanone, 4-methyl-2-pentanone, 3-methyl-2-pentanone, 3,3-dimethyl-2-butanone, 2-heptanone, and 2-octanone; cyclic ketones such as cyclopentanone, 3-methylcyclopentanone, cyclohexanone, 2-methylcyclohexanone, 2,6-dimethylcyclohexanone, and isophorone; propylene glycol monoalkyl ether acetates such as propylene glycol monomethyl ether acetate, propylene glycol monoethyl ether acetate, propylene glycol mono-n-propyl ether acetate, propylene glycol mono-i-propyl ether acetate, propylene glycol mono-n-butyl ether acetate, propylene glycol mono-i-butyl ether acetate, propylene glycol mono-sec-butyl ether acetate, and propylene glycol mono-t-butyl ether acetate; alkyl 2-hydroxypropionates such as methyl 2-hydroxypropionate, ethyl 2-hydroxypropionate, n-propyl 2-hydroxypropionate, i-propyl 2-hydroxypropionate, n-butyl 2-hydroxypropionate, i-butyl 2-hydroxypropionate, sec-butyl 2-hydroxypropionate, and t-butyl 2-hydroxypropionate; alkyl 3-alkoxypropionates such as methyl 3-methoxypropionate, ethyl 3-methoxypropionate, methyl 3-ethoxypropionate, and ethyl 3-ethoxypropionate; as well as other solvents such as n-propyl alcohol, i-propyl alcohol, n-butyl alcohol, t-butyl alcohol, cyclohexanol, ethylene glycol monomethyl ether, ethylene glycol monoethyl ether, ethylene glycol mono-n-propyl ether, ethylene glycol mono-n- butyl ether, diethylene glycol dimethyl ether, diethylene glycol diethyl ether, diethylene glycol di-n-propyl ether, diethylene glycol di-n-butyl ether, ethylene glycol monomethyl ether acetate, ethylene glycol monoethyl ether acetate, ethylene glycol mono-n-propyl ether acetate, propylene glycol monomethyl ether, propylene glycol monoethyl ether, propylene glycol mono-n-propyl ether, toluene, xylene, 2-hydroxy-2-methylethyl propionate, ethoxyethyl acetate, ethyl hydroxyacetate, methyl 2-hydroxy-3-methylbutyrate, 3-methoxybutylacetate, 3-methyl-3-methoxybutylacetate, 3-methyl-3-methoxybutylpropionate, 3-methyl-3-methoxybutylbutyrate, ethylacetate, n-propyl acetate, n-butylacetate, methyl acetoacetoate, ethyl acetoacetate, methyl pyruvate, ethyl pyruvate, N-methyl pyrrolidone, N,N-dimethylformamide, N,N-dimethylacetamide, benzyl ethyl ether, di-n-hexyl ether, diethylene glycol monomethyl ether, diethylene glycol monoethyl ether, caproic acid, caprylic acid, 1-octanol, 1-nonanol, benzyl alcohol, benzyl acetate, ethylbenzoate, diethyloxalate, diethylmaleate, γ-butyrolactone, ethylene carbonate, and propylene carbonate.

These solvents may be used either individually or in combination of two or more. Among these solvents, linear or branched ketones, cyclic ketones, propylene glycol monoalkyl ether acetates, alkyl 2-hydroxypropionates, and alkyl 3-alkoxypropionates are preferable.

Formation of Resist Patterns

A method of forming resist patterns using the radiation-sensitive resin composition (1) or the radiation-sensitive resin composition (2) will now be described.

In the radiation-sensitive resin composition (1) or radiation-sensitive resin composition (2), an acid is generated from the acid generator (b) upon exposure to radiation. The acid-dissociable group in the resin to dissociate by the action of the acid and generates a carboxyl group or hydroxyl group. As a result, solublity of the exposed part of the resist in an alkaline developer increases, whereby the exposed part is dissolved in an alkaline developer and removed to produce a positive-tone resist pattern.

A resist pattern is formed from the radiation-sensitive resin composition (1) or the radiation-sensitive resin composition (2) by applying the composition solution to, for example, substrates such as a silicon wafer or a wafer coated with aluminum using an appropriate application method such as rotational coating, cast coating, and roll coating to form a resist film. The resist film is then optionally pre-baked (hereinafter called "PB") and exposed to form a predetermined resist pattern. An F2 excimer laser (wavelength: 157 nm), ArF excimer laser (wavelength: 193 nm), and KrF excimer laser (wavelength: 248 nm) are preferable as radiation used for exposure.

In the present invention, it is preferable to perform post-exposure bake (hereinafter called "PEB") after exposure. The PEB ensures a smooth acid dissociation reaction from the resin (a). The heating temperature for PEB is usually 30–200° C., and preferably 50–170° C., although the heating conditions vary depending on the composition of the resist.

In order to fully bring out latent capability of the radiation-sensitive resin composition (1) and the radiation-sensitive resin composition (2), an organic or inorganic anti-reflection film may be formed on a substrate as disclosed in Japanese Patent Publication No. 12452/1994, for example. Moreover, a protection film may be formed on the resist film as disclosed in Japanese Patent Publication No. 188598/1993 or the like in order to prevent the effects of basic impurities or the like in an environmental atmosphere. These techniques may be employed in combination.

The exposed resist film is then developed to form a predetermined resist pattern.

As examples of a developer used for development, it is preferable to use an alkaline aqueous solution prepared by dissolving at least one of alkaline compounds such as sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethylammonium hydroxide, pyrrole, piperidine, choline, 1,8-diazabicyclo-[5.4.0]-7-undecene, and 1,5-diazabicyclo-[4.3.0]-5-nonene.

The concentration of the alkaline aqueous solution is usually 10 wt % or less. If the concentration of the alkaline aqueous solution exceeds 10 wt %, an unexposed area may be dissolved in the developer.

Organic solvents or the like may be added to the developer containing an alkaline aqueous solution.

As examples of organic solvents, ketones such as acetone, 2-butanone, 4-methyl-2-pentanone, cyclopentanone, cyclohexanone, 3-methylcyclopentanone, and 2,6-dimethylcyclohexanone; alcohols such as methylalcohol, ethylalcohol, n-propylalcohol, i-propylalcohbl, n-butylalcohol, t-butylalcohol, cyclopentanol, cyclohexanol, 1,4-hexanediol, and 1,4-hexanedimethylol; ethers such as tetrahydrofuran and dioxane; esters such as ethyl acetate, n-butyl acetate, and i-amyl acetate; aromatic hydrocarbons such as toluene and xylene; phenol, acetonylacetone, dimethylformamide; and the like can be given.

These organic solvents may be used either individually or in combination of two or more.

The amount of the organic solvents is preferably 100 vol % of the alkaline aqueous solution. If the amount of the organic solvents exceeds 100 vol %, an exposed area may remain undeveloped due to decreased developability.

In addition, surfactants or the like may be added to the developer containing the alkaline aqueous solution in an appropriate amount.

The resist film is generally washed with water after development using a developer containing an alkaline aqueous solution.

EXAMPLES

The present invention will be described in more detail by examples, which should not be construed as limiting the present invention.

In the examples, part(s) refers to part(s) by weight unless otherwise indicated. Measurement and evaluation were carried out as follows.
Mw:

Mw was measured by gel permeation chromatography (GPC) using GPC columns (manufactured by Tosoh Corp., G2000HXL×2, G3000HXL×1, G4000HXL×1) under the following conditions.
Flow rate: 1.0 ml/minute
Eluate: tetrahydrofuran
Column temperature: 40° C.
Standard reference material: monodispersed polystyrene
Radiation Transmittance:

A solution with a solid content of 5 wt %, prepared by dissolving a polysiloxane in 2-heptanibe, was applied onto a magnesium fluoride substrate by spin coating. The coated material was heated on a hot plate at 140° C. for 90 seconds to form a film with a thickness of 100 nm. The radiation transmittance of the film, calculated from absorbance of light with a wavelength of 157 nm and 193 nm, was used as a standard of transparency in the deep ultraviolet region.

Synthesis Example 1

Synthesis Silane Compound (6)

A three-necked flask equipped with a stirrer, a reflux condenser, and a thermometer was charged with 73.9 g of trimethoxysilane and 77.5 g of t-butyl acrylate. The mixture was stirred at room temperature and 0.1 ml of a 0.1 mol chloroplatinic acid ($H_2PtCl_6$) solution in isopropyl alcohol was added to initiate the reaction. After initiation of the reaction, the temperature increased as high as 60° C., then returned to room temperature. The mixture was stirred for three days at room temperature. After confirming that all raw materials substantially reacted, the reaction solution was filtered through celite by suction and the solvent was evaporated under vacuum to obtain an oily reaction product.

As shown by the following results of the measurement of NMR spectrum (chemical shift σ) and IR spectrum, the reaction product was identified to be 2-t-butoxycarbonylethyltrimethoxysilane.

σ: 3.6 ppm (methoxy group), 2.4–2.0 ppm (α-methylene group), 1.4 ppm (t-butyl group), 1.3–0.9 ppm (β-methylene group)
IR: 2847 $cm^{-1}$ (methoxy group), 1730 $cm^{-1}$ (ester group), 1153 $cm^{-1}$ (siloxane group), 1095 $cm^{-1}$ (siloxane group)

Comparative Example 1

Preparation of Comparative Polysiloxane

A three-necked flask equipped with a stirrer, a reflux condenser, and a thermometer was charged with 40 g of 2-t-butoxycarbonylethyltrimethoxysilane prepared in Synthesis Example 1, 120 g of 4-methyl-2-pentanone, 8.6 g of distilled water, and 4.0 g of triethylamine. The mixture was reacted for two hours at 62° C. while stirring. The flask was cooled with ice and a solution of 3.5 g of oxalic acid in 50 ml of ion-exchanged water was added, followed by continued stirring. The reaction mixture was poured into a separating funnel to remove the water layer. 100 ml of ion-exchanged water was additionally added to wash the organic layer. After removing the water layer, the solvent was evaporated under vacuum to obtain a comparative polysiloxane.

NMR spectrum (chemical shift σ), IR spectrum, and Mw of the comparative polysiloxane were measured. The results were as follows.

σ: 2.4–2.0 ppm (α-methylene group), 1.4 ppm (t-butyl group), 1.3–0.9 ppm (β-methylene group)
IR: 1730 $cm^{-1}$ (ester group), 1149 $cm^{-1}$ (siloxane group)
Mw: 19,500

Example 1

Preparation of Polysiloxane (1)

A three-necked flask equipped with a stirrer, a reflux condenser, and a thermometer was charged with 9.7 g of 2-t-butoxycarbonylethyltrimethoxysilane prepared in Synthesis Example 1, 5.3 g of methyltrimethoxysilane, 1.3 g of hexamethyldisiloxane, 75 g of 4-methyl-2-pentanone, 4.2 g of distilled water, and 4.2 g of triethylamine. The mixture was reacted for three hours at 62° C. while stirring. The flask was cooled with ice and a solution of 11.1 g of oxalic acid in 200 ml of ion-exchanged water was added, followed by continued stirring. The reaction mixture was poured into a separating funnel to remove the water layer. 100 ml of ion-exchanged water was additionally added to wash the organic layer. After removing the water layer, the solvent was evaporated under vacuum to obtain polysiloxane (1).

NMR spectrum (chemical shift σ), IR spectrum, and Mw of the polysiloxane (1) were measured to confirm the following results.

σ: 2.4–2.0 ppm (α-methylene group), 1.4 ppm (t-butyl group), 1.3–0.9 ppm (β-methylene group), 0.2 ppm ($SiCH_3$ group)
IR: 1730 $cm^{-1}$ (ester group), 1149 $cm^{-1}$ (siloxane group)
Mw: 44,700

Example 2

Preparation of Polysiloxane (1)

A three-necked flask equipped with a stirrer, a reflux condenser, and a thermometer was charged with 6.3 g of 2-t-butoxycarbonylethyltrimethoxysilane prepared in Synthesis Example 1, 13.7 g of methyltrimethoxysilane, 4.1 g of hexamethyldisiloxane, 100 g of 4-methyl-2-pentanone, 9.1 g of distilled water, and 12.7 g of triethylamine. The mixture was reacted for three hours at 62° C. while stirring. The flask was cooled with ice and a solution of 1.7 g of oxalic acid in 200 ml of ion-exchanged water was added, followed by continued stirring. The reaction mixture was poured into a separating funnel to remove the water layer. 100 ml of ion-exchanged water was additionally added to wash the organic layer. After removing the water layer, the solvent was evaporated under vacuum to obtain polysiloxane (1).

NMR spectrum (chemical shift σ), IR spectrum, and Mw of the polysiloxane (1) were measured to confirm the following results.

σ: 2.4–2.0 ppm (α-methylene group), 1.4 ppm (t-butyl group), 1.3–0.9 ppm (β-methylene group), 0.2 ppm ($SiCH_3$ group)

IR: 1730 $cm^{-1}$ (ester group), 1149 $cm^{-1}$ (siloxane group)

Mw: 22,400

Example 3

Synthesis of Silicon-Containing Alicyclic Compound (2)

A three-necked flask equipped with a stirrer, a reflux condenser, and a thermometer was charged with 48.5 g of trimethoxysilane and 77.1 g of 5-t-butoxycarbonylbicyclio[2.2.1]hept-2-ene. The mixture was stirred at room temperature and 1.0 ml of a 0.1 mol chior platinic acid solution in isopropyl alcohol was added to initiate the reaction. After heating at 140° C. for 48 hours while refluxing, the reaction mixture was allowed to cool to room temperature, diluted with n-hexane, and filtered through celite by suction. The solvent was evaporated by distillation under vacuum to obtain a crude product. The crude product was purified by vacuum distillation at 0.2 mmHg and a temperature of 105° C. to obtain 48 g of the reaction product.

This reaction product was identified to be the silicon containing alicyclic compound (2) shown by the formula (2-3) by the measurement of $^1$H-NMR spectrum (chemical shift σH), $^{13}$C-NMR spectrum (chemical shift σC), $^{29}$Si—NMR spectrum (chemical shift σSi), IR spectrum, and mass spectrum (FABMS), of which the results are shown below.

σH: 3.6 ppm (methoxy group), 1.4 ppm (t-butyl group)

σC: 175 ppm (carbonyl group), 80 ppm (t-butyl group)

σ: 51 ppm (methoxy group), 28 ppm (t-butyl group)

σSi: −45 ppm

IR: 2847 $cm^{-1}$ (methoxy group), 1730 $cm^{-1}$ (ester group), 1153 $cm^{-1}$ (siloxane group), 1095 $cm^{-1}$ (siloxane group)

FABMS: m/z=317 ($M^+$+1)

Example 4

Preparation of Polysiloxane (1)

A three-necked flask equipped with a stirrer, a reflux condenser, and a thermometer was charged with 7.35 g of the silicon containing alicyclic compound (2) prepared in Example 3, 12.65 g of trimethoxymethylsilane, 0.94 g of hexamethyldisiloxane, 100 g of 4-methyl-2-pentanone, 11.0 g of distilled water, and 14.8 g of triethylamine. The mixture was reacted for eight hours at 75° C. while stirring. The flask was cooled with ice and a solution of 12.9 g of oxalic acid in 250 ml of ion-exchanged water was added, followed by continued stirring. The reaction mixture was poured into a separating funnel to remove the water layer. 100 ml of ion-exchanged water was additionally added to wash the organic layer. After removing the water layer, the solvent was evaporated under vacuum to obtain polysiloxane (1).

NMR spectrum (chemical shift σ), IR spectrum, and Mw of the polysiloxane (1) were measured to confirm the following results.

σ: 1.4 ppm (t-butyl group), 0.2 ppm ($SiCH_3$ group)

IR: 1730 $cm^{-1}$ (ester group), 1149 $cm^{-1}$ (siloxane group)

Mw: 5,900

Evaluation Example 1

Evaluation of Radiation Transmittance

The radiation transmittance of the polysiloxanes obtained in Comparative Example 1, Example 2, and Example 4 at wavelengths of 157 nm and 193 nm was measured. In addition, the radiation transmittance at wavelengths of 157 nm and 193 nm was measured on a comparative polysiloxane consisting of 40 mol % of maleic anhydride, 40 mol % of 5-t-butoxycarbonylbicyclo[2.2.1]-hept-2-ene, and 20 mol % of 3-hydroxy-1-adamantylacrylate, as Comparative Example 2. The evaluation results are shown in Table 1.

TABLE 1

| Polysiloxane | Radiation transmittance (%) | |
|---|---|---|
| | 157 nm | 193 nm |
| Polysiloxane of Comparative Example 1 | 24 | 95 |
| Polysiloxane (1) of Example 2 | 32 | 99 |
| Polysiloxane (1) of Example 4 | 31 | 97 |
| Polysiloxane of Comparative Example 2 | 16 | 90 |

As a result, the polysiloxanes (1) of Examples 2 and 4 were confirmed to exhibit greater radiation transmittance than the comparative polysiloxane of Comparative Example 1 at both the wavelength 157 nm and wavelength 193 nm. These polysiloxanes (1) were also confirmed to exhibit remarkably high radiation transmittance at both the wavelength 157 nm and wavelength 193 nm as compared with the comparative polysiloxane of Comparative Example 2 which had been conventionally used as a chemically amplified resist.

Example 5

Radiation-Sensitive Resin Composition

A solution composition was prepared by homogeneously mixing 100 parts of the polysiloxane (1) obtained in Example 2, 1 part of triphenylsulfoniumtrifluoromethane sulfonate, 0.02 part of tri-n-octylamine, and 1,088 parts of 2-heptanone.

The solution composition was applied on to a silicon wafer substrate by spin coating and pre-baked for 90 seconds on a hot plate maintained at a temperature of 140° C. to form a resist film with a thickness of 200 nm.

The resist film was exposed to an F2 excimer laser (wavelength: 157 nm) while changing the irradiation dose, post-baked for 90 seconds on a hot plate at 120° C., and then developed in a 2.38% aqueous solution of tetramethylammonium hydroxide.

As a result, the area on the resist film exposed to radiation at a dose of 70 $J/m^2$ has completely been removed by development.

Comparative Example 3

Comparative Radiation-sensitive Resin Composition

A solution composition was prepared and a resist film was formed, exposed, and developed in the same manner as in Example 5, except for using the comparative polysiloxane of Comparative Example 2 instead of the polysiloxane (1) obtained in Example 2.

As a result, it was found that the area on the resist film exposed to radiation at a dose of 200 $J/m^2$ has not completely been removed by development.

Example 6

Synthesis of Silicon-Containing Alicyclic Compound (2)

A three-necked flask equipped with a stirrer, a reflux condenser, and a thermometer was charged with 46.5 g of triethoxysilane and 42 g of 5-t-butoxycarbonylbicyclo [2.2.1]hept-2-ene. The mixture was stirred at room temperature and 1.0 ml of a 0.2 mol chloroplatinic acid ($H_2PtCl_6$) solution in isopropyl alcohol was added to initiate the reaction. The reaction was continued for 24 hours at 140° C. while refluxing. The reaction mixture was allowed to cool to room temperature, diluted with n-hexane, and filtered through celite by suction The solvent was evaporated under vacuum to obtain a crude product. The crude product was purified by vacuum distillation at 0.4 mmHg and a temperature of 155° C. to obtain 54 g of the reaction product.

This reaction product was identified to be the silicon containing alicyclic compound (2) shown by the formula (2-6) by the measurement of $^1$H-NMR spectrum (chemical shift σH), $^{13}$C-NMR spectrum (chemical shift σC), $^{29}$Si—NMR spectrum (chemical shift σSi), IR spectrum, and mass spectrum (FABMS), of which the results are shown below.

σH: 3.8 ppm (ethoxy group), 1.4 ppm (t-butyl group)
σC: 175 ppm (carbonyl group), 80 ppm (t-butyl group), 59 ppm (ethoxy group), 28 ppm (t-butyl group), 19 ppm (methyl group).
σSi: −48 ppm
IR: 2879 cm$^{-1}$ (ethoxy group), 1726 cm$^{-1}$ (ester group), 1155 cm$^{-1}$ (siloxane group), 1080 cm$^{-1}$ (siloxane group)
FABMS: m/z=359 (M$^+$+1)

Example 7

Synthesis of Silicon-containing Alicyclic Compound (2)

A three-necked flask equipped with a stirrer, a reflux condenser, and a thermometer was charged with 49.0 g of trimethoxysilane and 73.0 g of 8-t-butoxycarbonyltetracyclo [4.4.0.1$^{2,5}$.1$^{7,10}$]-dodeca-3-ene. The mixture was stirred at room temperature and 5.0 ml of a 0.2 mol chloroplatinic acid ($H_2PtCl_6$) solution in isopropyl alcohol was added to initiate the reaction. The reaction was continued for 100 hours at 150° C. while refluxing. The reaction mixture was allowed to cool to room temperature, diluted with n-hexane, and filtered through celite by suction. The solvent was evaporated by distillation under vacuum to obtain a crude product. The residue was purified by silica gel column chromatography to obtain 30 g of the compound as a n-hexane fraction. This reaction product was identified to be the silicon containing alicyclic compound (2) shown by the formula (2-39) by the measurement of $^1$H-NMR spectrum (chemical shift σH), $^{13}$C-NMR spectrum (chemical shift σC), $^{29}$Si—NMR spectrum (chemical shift σSi), IR spectrum, and mass spectrum (FABMS), of which the results are shown below.

σH: 3.6 ppm (methoxy group), 1.4 ppm (t-butyl group)
σC: 175 ppm (carbonyl group), 80 ppm (t-butyl group), 51 ppm (ethoxy group), 28 ppm (t-butyl group)
σSi: −45 ppm
IR: 2847 cm$^{-1}$ (methoxy group), 1726 cm$^{-1}$ (ester group), 1153 cm$^{-1}$ (siloxane group), 1090 cm$^{-1}$ (siloxane group)
FABMS: m/z=383 (M$^+$+1)

Example 8

Synthesis of Silicon-Containing Alicyclic Compound (2)

A three-necked flask equipped with a stirrer, a reflux condenser, and a thermometer was charged with 76.0 g of triethoxysilane and 100 g of 8-t-butoxycarbonyl-tetracyclo [4.4.01$^{2,5}$,1$^{7,10}$]dodec-3-ene. The mixture was stirred at room temperature and 5.0 ml of a 0.2 mol chioroplatinic acid ($H_2PtCl_6$) solution in isopropyl alcohol was added to initiate the reaction. The reaction was continued for 75 hours at 150° C. while refluxing. The reaction mixture was allowed to cool to room temperature, diluted with n-hexane, and filtered through celite by suction. The solvent was evaporated by distillation under vacuum to obtain a crude product. The residue was purified by silica gel column chromatography to obtain 53 g of the compound as a n-hexane fraction.

This reaction product was identified to be the silicon containing alicyclic compound (2) shown by the formula (2-42) by the measurement of $^1$H-NMR spectrum (chemical shift σH), $^{13}$C-NMR spectrum (chemical shift σC), $^{29}$Si—NMR spectrum (chemical shift σSi), IR spectrum, and mass spectrum (FABMS), of which the results are shown below.

σH: 3.8 ppm (ethoxy group), 1.2 ppm (ethoxy group), 1.4 ppm (t-butyl group)
σC: 175 ppm (carbonyl group), 80 ppm (t-butyl group), 59 ppm (ethoxy group), 28 ppm (t-butyl group), 19 ppm (methyl group)
σSi: −48 ppm
IR: 2885 cm$^{-1}$ (ethoxy group), 1726 cm$^{-1}$ (ester group), 1153 cm$^{-1}$ (siloxane group), 1080 cm$^{-1}$ (siloxane group)
FABMS: m/z=425 (M$^+$+1)

Example 9

Synthesis of Silicon-containing Alicyclic Compound (2)

A three-necked flask equipped with a stirrer, a reflux condenser, and a ermometer was charged with 28.6 g of trimethylysilane and 50.0 g of 5-t-butoxycarbonyl-bicyclo [2.2.11]hept-2-ene. The mixture was stirred at room temperature and 1.0 ml of a 0.1 mol chloroplatinic acid ($H_2PtCl_6$) solution in isopropyl alcohol was added to initiate the reaction. The reaction was continued for 48 hours at 140° C. while refluxing. Reaction mixture was allowed to cool to room temperature, diluted with n-hexane, and filtered through celite by suction. The solvent was evaporated by distillation under vacuum to obtain a crude product. The crude product was purified by vacuum distillation at 0.2 mmHg and a temperature of 105° C. to obtain 42 g of the silicon containing alicyclic compound (2) having a methyl group for R', a hydrogen atom for R, m=3, and n=O in the formula (2-A).

Example 10

Synthesis of Silicon-containing Alicyclic Compound (2)

A three-necked flask equipped with a stirrer, a reflux condenser, and a thermometer was charged with 53.2 g of trichiorosilane and 50.0 g of 5-t-butoxycarbonylbicyclo [2.2.1]hept-2-ene. The mixture was stirred at room temperature and 1.0 ml of a 0.1 mol chloroplatinic acid ($H_2PtCl_6$) solution in isopropyl alcohol was added to initiate the reaction. The reaction was continued for 48 hours at 140° C. while refluxing. The reaction mixture was allowed to cool to room temperature, diluted with n-hexane, and filtered through celite by suction. The solvent was evaporated by distillation under vacuum to obtain a crude product. The crude product was purified by vacuum distillation at 0.2 mmHg and a temperature of 112° C. to obtain 60 g of the silicon containing alicyclic compound (2) of the formula (2-12).

Example 11

Synthesis of Silicon-Containing Alicyclic Compound (2)

A three-necked flask equipped with a stirrer, a reflux condenser, and a thermometer was charged with 51.8 g of methyldiethoxysilane and 50.0 g of 5-t-butoxycarbonylbcyclo[2.2.1]hept-2-ene. The mixture was stirred at room temperature and 1.0 ml of a 0.1 mol chloroplatinic acid ($H_2PtCl_6$) solution in isopropyl alcohol was added to initiate the reaction. The reaction was continued for 48 hours at 140° C. while refluxing. The reaction mixture was allowed to cool to room temperature, diluted with n-hexane, and filtered through celite by suction. The solvent was evaporated by distillation under vacuum to obtain a crude product. The crude product was purified by vacuum distillation at 0.2 mmHg and a temperature of 112° C. to ob am 60 g of the silicon containing alicyclic compound (2) of the formula (2-5).

Example 12

Synthesis of Silicon-containing Alicyclic Compound (2)

A three-necked flask equipped with a stirrer, a reflux condenser, and a tempermometer was charged with 17.1 g of trimethylsilane and 40 g of 8-t-butoxycarbonyltetracyclo[4.4.0.1$^{2,5}$,1$^{7,10}$]dodec-3-ene. The mixture was stirred at room temperature and 5.0 ml of a 0.2 mol chloroplatinic acid ($H_2PtCl_6$) solution in isopropyl alcohol was added to initiate the reaction. The reaction was continued for 100 hours at 50° C. while refluxing. The reaction mixture was allowed to cool to room temperature, diluted with n-hexane, and filtered through celite by suction. The solvent was evaporated by distillation under vacuum to obtain a crude product. The residue was purified by silica gel column chromatography to obtain 23 g of the silicon containing alicyclic compound (2) having a methl group for R' a hydrogen atom for R, m=3, and n=1 of the formula (2-A) as a n-hexane fraction.

Example 13

Synthesis of Silicon-containing Alicyclic Compound (2)

A three-necked flask equipped with a stirrer, a reflux condenser, and a thermometer was charged with 31.3 g of trichlorosilane and 40 g of 8-t-butoxycarbonyltetracyclo [4.4.1$^{2,5}$.1$^{17,10}$]-dodec-3-ene. The mixture was stirred at room temperature and 5.0 ml of a 0.2mol chloroplatinic acid ($H_2PtCl_6$) solution in isopropyl alcohol was added to initiate the reaction. The reaction was continued for 100 hours at 150° C. while refluxing. The reaction mixture was allowed to cool to room temperature, diluted with n-hexane, and filtered through celite by suction. The solvent was evaporated by distillation under vacuum to obtain a crude product. The residue was purified by silica gel column chromatography to obtain 37 g of the silicon containing alicyclic compound (2) of the formula (2-8) as an n-hexane fraction.

Example 14

Synthesis of Silicon-containing Alicyclic Compound (2)

A three-necked flask equipped with a stirrer, a reflux condenser, and a thermometer was charged with 30.9 g of methyldiethoxysilane and 40 g of 8-t-butoxycarbonyltetracyclo [4.4.0.1$^{2,5}$. 1$^{7,10}$]dodec-3-ene. The mixture was stirred at room temperature and 5.0 ml of a 0.2 mol chloroplatinic acid ($H_2PtCl_6$) solution in isopropyl alcohol was added to initiate the reaction. The reaction was continued for 100 hours at 150° C. while refluxing. The reaction mixture was allowed to cool to room temperature, diluted with n-hexane, and filtered through celite by suction. The solvent was evaporated by distillation under vacuum to obtain a crude product. The residue was purified by silica gel column chromatography to obtain 24 g of the silicon containing alicyclic compound (2) of the formula (2-41) as a n-hexane fraction.

Example 15

Synthesis of Silicon-containing Alicyclic Compound (2)

A three-necked flask equipped with a stirrer, a reflux condenser, and a thermometer was charged with 12.0 g of methyihydrocyclosiloxane (containing 3–5 Si atoms per molecule) and 52.0 g of 8-t-butoxycarbonylmethoxycarbonyltetracyclo[4.4.0. 1$^{2,5}$.1$^{7,10}$] dodec-3-ene. The mixture was stirred at room temperature and 5.0 ml of a 0.2 mol chloroplatini acid ($H_2PtCl_6$) solution in isopropyl alcohol was added to initiate the reaction. The reaction was continued for 100 hours at 150° C. while refluxing. The reaction mixture was allowed to cool to room temperature, diluted with n-hexane, and filtered through celite by suction. The solvent was evaporated by distillation under vacuum to obtain 59 g of the silicon containing alicyclic compound (2) of the above-mentioned formula (2-91).

$^1$H-NMR spectrum (chemical shift σH) and IR spectrum of the compound were measured. The results were as follows.

σH: 1.4 ppm (t-butyl group), 0.2 ppm ($SiCH_3$ group)
IR: 1730 cm$^{-1}$ (ester group), 1150 cm$^{-1}$ (siloxane group)

Example 16

Synthesis of Silicon-containing Alicyclic Compound (2)

A three-necked flask equipped with a stirrer, a reflux condenser, and a thermometer was charged with 3.0 g of the compound shown by the above formula (2-41) prepared in Synthesis Example 15, 9 g of 4-methyl-2-pentanone, and 0.56 g of 1.75 wt % oxalic acid aqueous solution. The mixture was reacted for two hours at 40° C. while stirring. The reaction was terminated by cooling the flask with ice. The reaction mixture was poured into a separating funnel to remove the water layer. The organic layer was washed with ion-exchanged water until the reaction solution becomes neutral. The solvent was removed from the organic layer by distillation under vacuum to obtain 1.90 g of the silicon containing alicyclic compound (2) of the formula (2-91).

$^1$H-NMR spectrum (chemical shift σH) and IR spectrum of the compound were measured and confirmed to be identical to those of the compound of Example 16.

Example 17

Preparation of Polysiloxane (3)

A three-necked flask equipped with a stirrer, a reflux condenser, and a thermometer was charged with 12.47 g of the silicon containing alicyclic compound (2) of the above formula (2-2), 12.53 g of methyltrimethoxysilane, 1.07 g of hexamethyldisiloxane (molecular weight adjusting agent), 75 g of 4-methyl-2-pentanone, 14.92 g of distilled water, and 20.93 g of triethylamine. The mixture was reacted for eight hours at 75° C. while stirring. The flask was cooled with ice and a solution of 18.2 g of oxalic acid in 500 ml of ion-exchanged water was added, followed by continued stirring. The reaction mixture was poured into a separating funnel to remove the water layer. 100 ml of ion-exchanged water was additionally added to wash the organic layer. The solvent was evaporated under vacuum to obtain polysiloxane (3).

$^1$H-NMR spectrum (chemical shift σH), IR spectrum, and Mw of the polysiloxane (3) were measured. The results were as follows.
σH: 1.4 ppm (t-butyl group), 0.2 ppm (SiCH$_3$ group)
IR: 1730 cm$^{-1}$ (ester group), 1149 cm$^{-1}$ (siloxane group)
Mw: 6,400

Comparative Example 4

Preparation of Comparative Polysiloxane

A three-necked flask equipped with a stirrer, a reflux condenser, and a thermometer was charged with 9.7 g of 2-t-butoxycarbonylethyltrimethoxysilane, 5.3 g of methyltrimethoxysilane, 1.3 g of hexamethyldisiloxane (molecular weight adjusting aagent), 75 g of 4-methyl-2-pentanone, 4.2 g of distilled water, and 4.2 g of triethylamine. The mixture was reacted for three hours at 62° C. while stirring. The flask was cooled with ice and a solution of 11.1 g of oxalic acid in 200 ml of ion-exchanged water was added, followed by continued stirring. The reaction mixture was poured into a separating funnel to remove the water layer. 100 ml of ion-exchanged water was additionally added to wash the organic layer. The solvent was evaporated under vacuum to obtain a comparative polysiloxane.

$^1$H-NMR spectrum (chemical shift σH), IR spectrum, and Mw of the comparative polysiloxane were measured. The results were as follows.
σH: 2.4–2.0 ppm (α-methylene group), 1.3–0.9 ppm (β-methylene group), 1.4 ppm (t-butyl group), 0.2 ppm (SiCH$_3$ group)
IR: 1730 cm$^{-1}$ (ester group), 1149 cm$^{-1}$ (siloxane group)
Mw: 44,700

Evaluation Example 2

Evaluation of Glass Transition Temperature

Glass transition temperature of the polysiloxane obtained in Example 17 and the polysiloxane obtained Comparative Example 4 was measured to confirm the glass transition temperature of the later polysiloxane was less than 25° C., whereas the former polysiloxane had a glass transition temperature of 97° C., which is sufficiently high as a resist component.

Evaluation Example 3

Evaluation of Radiation Transmittance

Radiation transmittance of coating films (thickness: 100 nm) formed from the polysiloxanes obtained in Example 17 and Comparative Example 4 was measured using radiation of a wavelength of 157 nm to confirm the radiation transmittance of the coating film prepared from the polysiloxane (3) of Example 17 was 31%, whereas that of the coating film prepared from the comparative polysiloxane of Comparative Example 4 was 32%.

Conventionally, the radiation transmittance at a wavelength of 157 nm has been thought to decrease as the proportion of hydrocarbon structures in a polysiloxane increases. The results of the measurement, however, indicated that notwithstanding a comparatively large proportion of hydrocarbon structures the polysiloxane (3) exhibited almost the same radiation transmittance at a wavelength of 157 nm as that of the comparative polysiloxane of Comparative Example 4, confirming that the hydrocarbon structures did not result in the decrease of transmittance.

Example 18

Radiation-sensitive Resin Composition

A solution composition was prepared by homogeneously mixing 100 parts of the polysiloxane (3) obtained in Example 18, 1 part of triphenylphosphonium trifluoromethane sulfonate, 0.02 part of tri-n-octylamine, and 900 parts of 2-heptanone.

The solution composition was applied onto a silicon wafer substrate by spin coating and pre-baked for 90 seconds at 140° C. to form a resist film with a thickness of 200 nm.

The resist film was exposed to an F2 excimer laser (wavelength: 157 nm) through a photo-mask, post-baked for 90 seconds on a hot plate at 120° C., and then developed in a 2.38 wt % aqueous solution of tetramethylammonium hydroxide.

As a result, a fine resist pattern confuguration with a line width of 0.5 μm was obtained.

Example 19

Preparation of Polysiloxane (1)

A three-necked flask equipped with a stirrer, a reflux condenser, and a thermometer was charged with 4.99 g of the silicon containing alicyclic compound (2) of the above formula (2-3), 5.01 g of trimethoxymethylsilane, 0.43 g of hexamethyldisiloxane, 30 g of 4-methyl-2-pentanone, and 2.91 g of a 2.37 wt % aqueous solution of oxalic acid. The mixture was reacted for four hours at 80° C. while stirring. The reaction was terminated by cooling the flask with ice. The reaction mixture was poured into a separating funnel to remove the water layer. The organic layer was washed with ion-exchanged water until the reaction solution becomes neutral. The solvent was removed from the organic layer to obtain the polysiloxane (1).

NMR spectrum (chemical shift σ), IR spectrum, and Mw of the polysiloxane (1) were measured to confirm the following results.
σ: 1.4 ppm (t-butyl group), 0.2 ppm (SiCH$_3$ group)
IR: 1730 cm$^{-1}$ (ester group), 1150 cm$^{-1}$ (siloxane group)
Mw: 1,700

No methoxy group peak originating from Si—OCH$_3$ which may present in the polymer was observed in the chemical shift σ.

Example 20

Preparation of Polysiloxane (1)

A three-necked flask equipped with a stirrer, a reflux condenser, and a thermometer was charged with 4.99 g of the silicon containing alicyclic compound (2) of the above formula (2-3), 5.01 g of trimethoxymethylsilane, 0.43 g of hexamethyldisiloxane, 30 g of 4-methyl-2-pentanone, and 2.91 g a 2.37 wt % aqueous solution of oxalic acid. The mixture was reacted for four hours at 80° C. while stirring. The reaction was terminated by cooling the flask with ice. The reaction mixture was poured into a separating funnel to remove the water layer. The organic layer was washed with ion-exchanged water until the reaction solution becomes neutral. The solvent was removed from the organic layer to obtain 6.7 g of a polymer having Mw of 1,700.

The polymer was dissolved in 30 g of 4-methyl-2-pentanone. After the addition of 5.7 g of distilled water and 8.0 g of triethylamine, the mixture was heated to 40° C. in a nitrogen stream. After two hours, the mixture was cooled with ice and stirred, then a solution of 3.5 g of oxalic acid in 150 g of distilled water was added, and stirring was continued. The reaction mixture was poured into a separating funnel to remove the water layer. The organic layer was washed with ion-exchanged water until the reaction solution becomes neutral. The solvent was removed from the organic layer to obtain the polysiloxane (1).

NMR spectrum (chemical shift σ), IR spectrum, and Mw of the polysiloxane (1) were measured to confirm the following results.

σ: 1.4 ppm (t-butyl group), 0.2 ppm ($SiCH_3$ group)
IR: 1730 $cm^{-1}$ (ester group), 1150 $cm^{-1}$ (siloxane group)
Mw: 2,700

No methoxy group peak originating from Si—$OCH_3$ which may present in the polymer was observed in the chemical shift σ.

Comparative Example 5

Preparation of Comparative Polysiloxane

A three-necked flask equipped with a stirrer, a reflux condenser, and a thermometer was charged with 4.99 g of the silicon containing alicyclic compound (2) of the above formula (2-3), 5.01 g of trimethoxymethylsilane, 0.43 g of hexamethyldisiloxane, 30 g of 4-methyl-2-pentanone, and 5.97 g of distilled water, and 8.37 g of triethylamine. The mixture was reacted for four hours at 80° C. while stirring. The flask was cooled with ice and a solution of 7.31 g of oxalic acid in 250 ml of ion-exchanged water was added, followed by continued stirring. The reaction mixture was poured into a separating funnel to remove the water layer. 100 ml of ion-exchanged water was further added to wash the organic layer, then the water layer was removed. The solvent was removed from the organic layer to obtain a polymer. NMR spectrum (chemical shift σ), IR spectrum, and Mw of the polymer were measured. The results were as follows.

σ: 3.6 ppm (methoxy group), 1.4 ppm (t-butyl group), 0.2 ppm ($SiCH_3$ group)
IR: 1730 $cm^{-1}$ (ester group), 1149 $cm^{-1}$ (siloxane group)
Mw: 4,900

The 3.6 ppm peak of a is due to the methoxy group originating from Si—$OCH_3$ remaining in the polymer.

Example 21

Radiation-sensitive Resin Composition

A solution composition was prepared by homogeneously mixing 100 parts of the polysiloxane obtained in Example 19, Example 20, or Comparative Example 5, 1 part of triphenylphosphonium nonafluoro-n-butenesulfonate, 0.02 part of tri-n-octylamine, and 900 parts of 2-heptanone.

The solution composition was applied onto a silicon wafer substrate by spin coating and pre-baked for 90 seconds at 130° C. to form a resist film with a thickness of 100 nm.

The resist film was exposed to a KrF excimer laser (wavelength: 248 nm) while changing the irradiation dose, post-baked for 90 seconds on a hot plate at 100° C., and then developed in a 2.38 wt % aqueous solution of tetramethylammonium hydroxide.

Observation of the exposed area on the substrate by a scanning-type electron microscope confirmed that the limit resolution was 0.30 nm when the comparative polysiloxane of Comparative Example 5 was used, whereas the limit resolution was respectively 0.24 nm and 0.22 nm when the polysiloxanes (1) obtained in Example 19 and Example 20 was used.

In addition, the pattern shape obtained by using the polysiloxane (1) obtained in Example 19 or Example 20 exhibited more excellent rectangular configuration than that obtained using the comparative polysiloxane of Comparative Example 5.

Evaluation Example 4

Evaluation of Radiation Transmittance

The radiation transmittance of coating films with a thickness of 100 nm prepared from the polysiloxane of Example 20 or Comparative Example 5 at wavelengths of 157 nm and 193 nm was measured. The results are shown in Table 2.

TABLE 2

| Polysiloxane | Radiation transmittance (%) | |
|---|---|---|
| | 157 nm | 193 nm |
| Polysiloxane (1) of Example 20 | 38 | 96 |
| Polysiloxane of Comparative Example 5 | 31 | 96 |

The results in the above table shows that the polysiloxane (1) polycondensed under acid conditions and the comparative polysiloxane polycondensed under basic conditions exhibited no substantial difference in the radiation transmittance at a wavelength of 193 nm, whereas the former polysiloxane exhibited higher radiation transmittance at a wavelength of 157 than the latter polysiloxane. This indicates that the polysiloxane (1) polycondensed under acid conditions will be a more desirable material for microfabrication using radiation with a short wavelength.

Example 22

Preparation of Polysiloxane (1)

A three-necked flask equipped with a stirrer, a reflux condenser, and a thermometer was charged with 3.84 g of the silicon containing alicyclic compound (2) of the above formula (2-42), 7.93 g of the silicon containing alicyclic compound (4) of the above formula (4-6) (wherein Rf is a trifluoromethyl group), 3.22 g of methylethoxysilane, 10.5 g of 4-methyl-2-pentanone, and 3.32 g of a 1.75 wt % aqueous solution of oxalic acid. The mixture was reacted for six hours at 80° C. while stirring. The reaction was terminated by cooling the flask with ice. The reaction mixture was poured into a separating funnel to remove the water layer. The organic layer was washed with ion-exchanged water until the reaction solution becomes neutral. The solvent was removed from the organic layer to obtain the polysiloxane (1).

NMR spectrum (chemical shift σ), IR spectrum, and Mw of the polysiloxane (1) were measured to confirm the following results.

σ: 2.3 ppm (—$CH_2C(CF_3)_2$ group), 1.4 ppm (t-butyl group), 0.2 ppm ($SiCH_3$ group)
IR: 1700 $cm^{-1}$ (ester group), 1213 $cm^{-1}$ (C—F bond), 1151 $cm^{-1}$ (siloxane group)
Mw: 2,100

Example 23

Preparation of Polysiloxane (1)

A three-necked flask equipped with a stirrer, a reflux condenser, and a thermometer was charged with 3.84 g of the silicon containing alicyclic compound (2) of the above formula (2-42), 7.93 g of the silicon containing alicyclic compound (4) of the above formula (4-6) (wherein Rf is a trifluoromethyl group), 3.22 g of methylethoxysilane, 15 g of 4-methyl-2-pentanone, and 3.32 g of a 1.75 wt % aqueous solution of oxalic acid. The mixture was reacted for two hours at 80° C. while stirring. The reaction was terminated by cooling the flask with ice. The reaction mixture was poured into a separating funnel to remove the water layer. The organic layer was washed with ion-exchanged water until the reaction solution becomes neutral. The solvent was removed from the organic layer to obtain 10 g of a polymer having Mw of 1,600.

The polymer was dissolved in 23 g of 4-methyl-2-pentanone. After the addition of 4.9 g of distilled water and 6.9 g of triethylamine, the mixture was heated to 40° C. in a nitrogen stream. After two hours, the mixture was cooled with ice and stirred, then a solution of 5.7 g of oxalic acid in 200 g of distilled water was added, and stirring was continued. The reaction mixture was poured into a separating funnel to remove the water layer. The organic layer was washed with ion-exchanged water until the reaction solution becomes neutral. The solvent was removed from the organic layer to obtain the polysiloxane (1).

NMR spectrum (chemical shift σ), IR spectrum, and Mw of the polysiloxane (1) were measured to confirm the following results.

σ: 2.3 ppm (—$CH_2C(CF_3)_2$ group), 1.4 ppm (t-butyl group), 0.2 ppm ($SiCH_3$ group)
IR: 1700 $cm^{-1}$ (ester group), 1213 $cm^{-1}$ (C—F bond), 1151 $cm^{-1}$ (siloxane group)
Mw: 2,600

Comparative Example 6

Preparation of Comparative Polysiloxane

A three-necked flask equipped with a stirrer, a reflux condenser, and a thermometer was charged with 3.84 g of the silicon containing alicyclic compound (2) of the above formula (2-42), 7.93 g of the silicon containing alicyclic compound (4) of the above formula (4-6) (wherein Rf is a trifluoromethyl group), 3.22 g of methylethoxysilane, 15 g of 4-methyl-2-pentanone, 4.9 g of distilled water, and 6.9 g of triethylamine. The mixture was reacted for ten hours at 80° C. while stirring. After cooling the mixture with ice, a solution of 5.7 g of oxalic acid in 200 g of distilled water was added, followed by continued stirring. The reaction mixture was poured into a separating funnel to remove the water layer. The organic layer was washed with ion-exchanged water until the reaction solution becomes neutral. The solvent was removed from the organic layer to obtain a comparative polymer.

NMR spectrum (chemical shift σ), IR spectrum, and Mw of the comparative polysiloxane were measured. The results were as follows.

σ: 3.6 ppm (methoxy group), 2.3 ppm (—$CH_2C(CF_3)_2$ group), 1.4 ppm (t-butyl group), 0.2 ppm ($SiCH_3$ group)
IR: 1700 $cm^{-1}$ (ester group), 1213 $cm^{-1}$ (C—F bond), 1151 $cm^{-1}$ (siloxane group)
Mw: 3,900

The 3.6 ppm peak of σ is due to the methoxy group originating from Si—$OCH_3$ remaining in the polymer.

Evaluation Example 5

Evaluation of Glass Transition Temperature

The glass transition temperature of the polysiloxanes obtained in Example 22, Example 23, and Comparative Example 6 was measured.

As a result, the comparative polysiloxane obtained in Comparative Example 6 was found to have a glass transition temperature of 92° C., whereas the polysiloxanes (1) obtained in Example 22 and Example 23 was found to have a glass transition temperature respectively of 111° C. or 122° C., confirming that the polysiloxanes (1) prepared by polycondensation under acidic conditions have a higher glass transition temperature than the comparative polysiloxane prepared by polycondensation under basic conditions.

As clear from the glass transition temperature of the polysiloxanes (1) obtained in Example 22 and Example 23, polysiloxanes synthesized by polycondensation under acidic conditions followed by basic conditions have been confirmed to have a glass transition temperature higher than polysiloxanes synthesized by polycondensation only under acidic conditions. This indicates that, the glass transition temperature of polysiloxane (1) can be increased by increasing the degrees of polymerization and crosslinking by polycondensation of a raw material compound under acidic conditions, followed by basic conditions. Thus, the glass transition temperature of polysiloxane (1) can be controlled by selection of polymerization conditions. Increasing the glass transition temperature of a resin component used in a radiation-sensitive resin composition is an important factor in forming fine resist patterns by a lithographic process. In this respect, the capability of controlling the glass transition temperature of the polysiloxane (1) is a feature supporting the usefulness of the present invention.

Example 24

Preparation of Polysiloxane (1)

A three-necked flask equipped with a stirrer, a reflux condenser, and a thermometer was charged with 3.83 g of the silicon containing alicyclic compound (4) of the above formula (4-6) (wherein Rf is a trifluoromethyl group), 1.17 g of the silicon containing alicyclic compound (4) of the above formula (4-6) (wherein Rf is a trifluoromethyl group) by replacing the hydrogen atom of the hydroxyl group by a t-butoxycarbonyl group, 2.5 g of 4-methyl-2-pentanone, and 0.80 g of a 1.75 wt % aqueous solution of oxalic acid. The mixture was reacted for ten hours at 40° C. while stirring. The reaction was terminated by cooling the flask with ice. The reaction mixture was poured into a separating funnel to remove the water layer. The organic layer was washed with ion-exchanged water until the reaction solution becomes neutral. The solvent was removed from the organic layer to obtain the polysiloxane (1).

NMR spectrum (chemical shift σ), IR spectrum, and Mw of the polysiloxane (1) were measured to confirm the following results.

σ: 2.3 ppm (—$CH_2C(CF_3)_2$ group), 1.5 ppm (t-butyl group)
IR: 1775 $cm^{-1}$ (ester group), 1219 $cm^{-1}$ (C—F bond), 1131 $cm^{-1}$ (siloxane group)
Mw: 1,700
Mw/Mn: 1.1

Example 25

Preparation of Polysiloxane (1)

The polymer obtained in Example 24 was dissolved in 10.8 g of 4-methyl-2-pentanone. After the addition of 1.18 g of distilled water and 1.65 g of triethylamine, the mixture was heated to 40° C. in a nitrogen stream. After five hours, the mixture was cooled with ice and stirred, then a solution of 1.38 g of oxalic acid in 50 g of distilled water was added, and stirring was continued. The reaction mixture was poured into a separating funnel to remove the water layer. The organic layer was washed with ion-exchanged water until the reaction solution becomes neutral. The solvent was removed from the organic layer to obtain the polysiloxane (1).

NMR spectrum (chemical shift σ), IR spectrum, and Mw of the polysiloxane (1) were measured to confirm the following results.

σ: 2.3 ppm (—$CH_2C(CF_3)_2$ group), 1.5 ppm (t-butyl group)
IR: 1775 $cm^{-1}$ (carbonic acid ester group), 1220 $cm^{-1}$ (C—F bond), 1133 $cm^{-1}$ (siloxane group)
Mw: 2,400
Mw/Mn: 1.1

Example 26

Preparation of Polysiloxane (1)

The polymer obtained in Example 24 was dissolved in 10.8 g of 4-methyl-2-pentanone. After the addition of 1.18 g of distilled water and 1.65 g of triethylamine, the mixture was heated to 60° C. in a nitrogen stream. After five hours, the mixture was cooled with ice and stirred, then a solution of 1.38 g of oxalic acid in 50 g of distilled water was added, and stirring was continued. The reaction mixture was poured into a separating funnel to remove the water layer. The organic layer was washed with ion-exchanged water until the reaction solution becomes neutral. The solvent was removed from the organic layer to obtain the polysiloxane (1).

NMR spectrum (chemical shift σ), IR spectrum, and Mw of the polysiloxane (1) were measured to confirm the following results.

σ: 2.3 ppm (—$CH_2C(CF_3)_2$ group), 1.5 ppm (t-butyl group)
IR: 1775 $cm^{-1}$ (carbonic acid ester group), 1221 $cm^{-1}$ (C—F bond), 1133 $cm^{-1}$ (siloxane group)
Mw: 2,700
Mw/Mn: 1.1

Example 27

Preparation of Polysiloxane (1)

The polymer obtained in Example 24 was dissolved in 10.8 g of 4-methyl-2-pentanone. After the addition of 1.18 g of distilled water and 1.65 g of triethylamine, the mixture was heated to 80° C. in a nitrogen stream. After five hours, the mixture was cooled with ice and stirred, then a solution of 1.38 g of oxalic acid in 50 g of distilled water was added, and stirring was continued. The reaction mixture was poured into a separating funnel to remove the water layer. The organic layer was washed with ion-exchanged water until the reaction solution becomes neutral. The solvent was removed from the organic layer to obtain the polysiloxane (1).

NMR spectrum (chemical shift σ), IR spectrum, and Mw of the polysiloxane (1) were measured to confirm the following results.

σ: 2.3 ppm (—$CH_2C(CF_3)_2$ group), 1.5 ppm (t-butyl group)
IR: 1775 $cm^{-1}$ (carbonic acid ester group), 1220 $cm^{-1}$ (C—F bond), 1129 $cm^{-1}$ (siloxane group)
Mw: 3,500
Mw/Mn: 1.2

Example 28

Preparation of Polysiloxane (1)

A three-necked flask equipped with a stirrer, a reflux condenser, and a thermometer was charged with 1.90 g of the silicon containing alicyclic compound (2) of the above formula (2-42), 6.89 g of the silicon containing alicyclic compound (4) of the above formula (4-6) (wherein Rf is a trifluoromethyl group), 1.21 g of the silicon containing alicyclic compound (4) of the above formula (4-6) (wherein Rf is a trifluoromethyl group) by replacing the hydrogen atom of the hydroxyl group by a t-butoxycarbonyl group, 10 g of 4-methyl-2-pentanone, and 1.65 g of a 1.75 wt % aqueous solution of oxalic acid. The mixture was reacted for ten hours at 40° C. while stirring. The reaction was terminated by cooling the flask with ice. The reaction mixture was poured into a separating funnel to remove the water layer. The organic layer was washed with ion-exchanged water until the reaction solution becomes neutral. The solvent was removed from the organic layer to obtain the polysiloxane (1)

NMR spectrum (chemical shift σ), IR spectrum, and Mw of the polysiloxane (1) were measured to confirm the following results.

σ: 2.3 ppm (—$CH_2C(CF_3)_2$ group), 1.4 ppm (t-butyl group), 1.5 ppm (t-butoxycarbonyl group)
IR: 1775 $cm^{-1}$ (carbonic acid ester group), 1726 $cm^{-1}$ (ester group), 1221 $cm^{-1}$ (C—F bond), 1131 $cm^{-1}$ (siloxane group)
Mw: 2,300
Mw/Mn: 1.1

Example 29

Preparation of Polysiloxane (1)

A three-necked flask equipped with a stirrer, a reflux condenser, and a thermometer was charged with 1.86 g of the silicon containing alicyclic compound (2) of the above formula (2-42), 5.77 g of the silicon containing alicyclic compound (4) of the above formula (4-6) (wherein Rf is a trifluoromethyl group), 2.36 g of the silicon containing alicyclic compound (4) of the above formula (4-6) (wherein Rf is a trifluoromethyl group) by replacing the hydrogen atom of the hydroxyl group by a t-butoxycarbonyl group, 10 g of 4-methyl-2-pentanone, and 1.61 g of a 1.75 wt % aqueous solution of oxalic acid. The mixture was reacted for ten hours at 40° C. while stirring. The reaction was terminated by cooling the flask with ice. The reaction mixture was poured into a separating funnel to remove the water layer. The organic layer was washed with ion-exchanged water until the reaction solution becomes neutral. The solvent was removed from the organic layer to obtain 7.5 g of a polymer having Mw of 1,500 and Mw/Mn of 1.1.

The polymer was dissolved in 22.7 g of 4-methyl-2-pentanone. After the addition of 2.37 g of distilled water and 3.33 g of triethylamine, the mixture was heated to 60° C. in a nitrogen stream. After five hours, the mixture was cooled with ice and stirred, then a solution of 2.77 g of oxalic acid in 70 g of distilled water was added, and stirring was continued. The reaction mixture was poured into a separating funnel to remove the water layer. The organic layer was washed with ion-exchanged water until the reaction solution becomes neutral. The solvent was removed from the organic layer to obtain the polysiloxane (1).

NMR spectrum (chemical shift σ), IR spectrum, and Mw of the polysiloxane (1) were measured to confirm the following results.

σ: 2.3 ppm (—$CH_2C(CF_3)_2$ group), 1.4 ppm (t-butyl group), 1.5 ppm (t-butoxycarbonyl group)
IR: 1775 $cm^{-1}$ (carbonic acid ester group), 1726 $cm^{-1}$ (ester group), 1220 $cm^{-1}$ (C—F bond), 1131 $cm^{-1}$ (siloxane group)
Mw: 2,300
Mw/Mn: 1.1

Example 30

Preparation of Polysiloxane (1)

A three-necked flask equipped with a stirrer, a reflux condenser, and a thermometer was charged with 1.28 g of the silicon containing alicyclic compound (2) of the above formula (2-42), 3.30 g of the silicon containing alicyclic compound (4) of the above formula (4-6) (wherein Rf is a trifluoromethyl group), 2.43 g of the silicon containing alicyclic compound (4) of the above formula (4-6) (wherein Rf is a trifluoromethyl group) by replacing the hydrogen atom of the hydroxyl group by a t-butoxycarbonyl group, 7 g of 4-methyl-2-pentanone, and 1.10 g of a 1.75 wt % aqueous solution of oxalic acid. The mixture was reacted for ten hours at 40° C. while stirring. The reaction was terminated by cooling the flask with ice. The reaction mixture was poured into a separating funnel to remove the water layer. The organic layer was washed with ion-exchanged water until the reaction solution becomes neutral. The solvent was removed from the organic layer to obtain 7.5 g of a polymer having Mw of 1,400 and Mw/Mn of 1.1.

The polymer was dissolved in 16.0 g of 4-methyl-2-pentanone. After the addition of 1.63 g of distilled water and 2.28 g of triethylamine, the mixture was heated to 60° C. in a nitrogen stream. After five hours, the mixture was cooled with ice and stirred, then a solution of 1.90 g of oxalic acid in 50 g of distilled water was added, and stirring was continued. The reaction mixture was poured into a separating funnel to remove the water layer. The organic layer was washed with ion-exchanged water until the reaction solution becomes neutral. The solvent was removed from the organic layer to obtain the polysiloxane (1).

NMR spectrum (chemical shift σ), IR spectrum, and Mw of the polysiloxane (1) were measured to confirm the following results.

σ: 2.3 ppm (—$CH_2C(CF_3)^2$ group), 1.4 ppm (t-butyl group), 1.5 ppm (t-butoxycarbonyl group)
IR: 1776 $cm^{-1}$ (carbonic acid ester group), 1726 $cm^{-1}$ (ester group), 1220 $cm^{-1}$ (C—F bond), 1132 $cm^{-1}$ (siloxane group)
Mw: 2,300
Mw/Mn: 1.1

Example 31

Preparation of Polysiloxane (1)

A three-necked flask equipped with a stirrer, a reflux condenser, and a thermometer was charged with 2.79 g of the silicon containing alicyclic compound (4) of the above formula (4-6) (wherein Rf is a trifluoromethyl group), 1.14 g of the silicon containing alicyclic compound (4) of the above formula (4-6) (wherein Rf is a trifluoromethyl group) by replacing the hydrogen atom of the hydroxyl group by a t-butoxycarbonyl group, 1.07 g of the silicon containing alicyclic compound (4) of the above formula (4-42), 5 g of 4-methyl-2-pentanone, and 0.78 g of a 1.75 wt % aqueous solution of oxalic acid. The mixture was reacted for ten hours at 40° C. while stirring. The reaction was terminated by cooling the flask with ice. The reaction mixture was poured into a separating funnel to remove the water layer. The organic layer was washed with ion-exchanged water until the reaction solution becomes neutral. The solvent was removed from the organic layer to obtain 3.6 g of a polymer having Mw of 1,600 and Mw/Mn of 1.1.

The polymer was dissolved in 11.4 g of 4-methyl-2-pentanone. After the addition of 1.15 g of distilled water and 1.61 g of triethylamine, the mixture was heated to 60° C. in a nitrogen stream. After five hours, the mixture was cooled with ice and stirred, then a solution of 1.34 g of oxalic acid in 50 g of distilled water was added, and stirring was continued. The reaction mixture was poured into a separating funnel to remove the water layer. The organic layer was washed with ion-exchanged water until the reaction solution becomes neutral. The solvent was removed from the organic layer to obtain the polysiloxane (1).

NMR spectrum (chemical shift σ), IR spectrum, and Mw of the polysiloxane (1) were measured to confirm the following results.

σ: 2.3 ppm (—$CH_2C(CF_3)_2$ group), 1.5 ppm (t-butoxycarbonyl group)
IR: 1775 $cm^{-1}$ (carbonic acid ester group), 1221 $cm^{-1}$ (C—F bond), 1130 $cm^{-1}$ (siloxane group)
Mw: 2,500
Mw/Mn: 1.1

Example 32

Preparation of Polysiloxane (1)

A three-necked flask equipped with a stirrer, a reflux condenser, and a thermometer was charged with 3.19 g of the silicon containing alicyclic compound (4) of the above formula (4-6) (wherein Rf is a trifluoromethyl group), 2.35 g of the silicon containing alicyclic compound (4) of the above formula (4-6) (wherein Rf is a trifluoromethyl group) by replacing the hydrogen atom of the hydroxyl group by a t-butoxycarbonyl group, 1.47 g of the silicon containing alicyclic compound (4) of the above formula (4-42), 7 g of 4-methyl-2-pentanone, and 1.07 g of a 1.75wt % aqueous solution of oxalic acid. The mixture was reacted for ten hours at 40° C. while stirring. The reaction was terminated by cooling the flask with ice. The reaction mixture was poured into a separating funnel to remove the water layer. The organic layer was washed with ion-exchanged water until the reaction solution becomes neutral. The solvent was removed from the organic layer to obtain 5.3 g of a polymer having Mw of 1,500 and Mw/Mn of 1.1.

The polymer was dissolved in 16.1 g of 4-methyl-2-pentanone. After the addition of 1.57 g of distilled water and 2.20 g of triethylamine, the mixture was heated to 60° C. in a nitrogen stream. After five hours, the mixture was cooled with ice and stirred, then a solution of 1.83 g of oxalic acid in 50 g of distilled water was added, and stirring was continued. The reaction mixture was poured into a separating funnel to remove the water layer. The organic layer was washed with ion-exchanged water until the reaction solution becomes neutral. The solvent was removed from the organic layer to obtain the polysiloxane (1).

NMR spectrum (chemical shift σ), IR spectrum, and Mw of the polysiloxane (1) were measured to confirm the following results.

σ: 2.3 ppm (—CH$_2$C(CF$_3$)$_2$ group), 1.5 ppm (t-butoxycarbonyl group)
IR: 1774 cm$^{-1}$ (carbonic acid ester group), 1220 cm$^{-1}$ (C—F bond), 1132 cm$^{-1}$ (siloxane group)
Mw: 2,500
Mw/Mn: 1.1

Example 33

Preparation of Polysiloxane (1)

A three-necked flask equipped with a stirrer, a reflux condenser, and a thermometer was charged with 0.45 g of the silicon containing alicyclic compound (2) of the above formula (2-42), 2.33 g of the silicon containing alicyclic compound (4) of the above formula (4-6) (wherein Rf is a trifluoromethyl group), 1.15 g of the silicon containing alicyclic compound (4) of the above formula (4-6) (wherein Rf is a trifluoromethyl group) by replacing the hydrogen atom of the hydroxyl group by a t-butoxycarbonyl group, 1.07 g of the silicon containing alicyclic compound (4) of the above formula (4-42), 5 g of 4-methyl-2-pentanone, and 0.78 g of a 1.75 wt % aqueous solution of oxalic acid. The mixture was reacted for ten hours at 40° C. while stirring. The reaction was terminated by cooling the flask with ice. The reaction mixture was poured into a separating funnel to remove the water layer. The organic layer was washed with ion-exchanged water until the reaction solution becomes neutral. The solvent was removed from the organic layer to obtain 3.7 g of a polymer having Mw of 1,600 and Mw/Mn of 1.1.

The polymer was dissolved in 11.5 g of 4-methyl-2-pentanone. After the addition of 1.15 g of distilled water and 1.61 g of triethylamine, the mixture was heated to 60° C. in a nitrogen stream. After five hours, the mixture was cooled with ice and stirred, then a solution of 1.34 g of oxalic acid in 50 g of distilled water was added, and stirring was continued. The reaction mixture was poured into a separating funnel to remove the water layer. The organic layer was washed with ion-exchanged water until the reaction solution becomes neutral. The solvent was removed from the organic layer to obtain the polysiloxane (1).

NMR spectrum (chemical shift σ), IR spectrum, and Mw of the polysiloxane (1) were measured to confirm the following results.

σ: 2.3 ppm (—CH$_2$C(CF$_3$)$_2$ group), 1.4 ppm (t-butyl group), 1.5 ppm (t-butoxycarbonyl group)
IR: 1776 cm$^{-1}$ (carbonic acid ester group), 1725 cm$^{-1}$ (ester group), 1220 cm$^{-1}$ (C—F bond), 1130 cm$^{-1}$ (siloxane group)
Mw: 2,500
Mw/Mn: 1.1

Example 34

Preparation of Polysiloxane (1)

A three-necked flask equipped with a stirrer, a reflux condenser, and a thermometer was charged with 0.92 g of the silicon containing alicyclic compound (2) of the above formula (2-42), 2.39 g of the silicon containing alicyclic compound (4) of the above formula (4-6) (wherein Rf is a trifluoromethyl group), 0.59 g of the silicon containing alicyclic compound (4) of the above formula (4-6) (wherein Rf is a trifluoromethyl group) by replacing the hydrogen atom of the hydroxyl group by a t-butoxycarbonyl group, 1.10 g of the silicon containing alicyclic compound (4) of the above formula (4-42), 5 g of 4-methyl-2-pentanone, and 0.80 g of a 1.75 wt % aqueous solution of oxalic acid. The mixture was reacted for ten hours at 40° C. while stirring. The reaction was terminated by cooling the flask with ice. The reaction mixture was poured into a separating funnel to remove the water layer. The organic layer was washed with ion-exchanged water until the reaction solution becomes neutral. The solvent was removed from the organic layer to obtain 3.7 g of a polymer having Mw of 1,500 and Mw/Mn of 1.1.

The polymer was dissolved in 11.4 g of 4-methyl-2-pentanone. After the addition of 1.18 g of distilled water and 1.65 g of triethylamine, the mixture was heated to 60° C. in a nitrogen stream. After five hours, the mixture was cooled with ice and stirred, then a solution of 1.37 g of oxalic acid in 50 g of distilled water was added, and stirring was continued. The reaction mixture was poured into a separating funnel to remove the water layer. The organic layer was washed with ion-exchanged water until the reaction solution becomes neutral. The solvent was removed from the organic layer to obtain the polysiloxane (1).

NMR spectrum (chemical shift σ), IR spectrum, and Mw of the polysiloxane (1) were measured to confirm the following results.

σ: 2.3 ppm (—CH$_2$C(CF$_3$)$_2$ group), 1.4 ppm (t-butyl group), 1.5 ppm (t-butoxycarbonyl group)
IR: 1775 cm$^{-1}$ (carbonic acid ester group), 1726 cm$^{-1}$ (ester group), 1221 cm$^{-1}$ (C—F bond), 1132 cm$^{-1}$ (siloxane group)
Mw: 2,400
Mw/Mn: 1.1

Example 35

Preparation of Polysiloxane (1)

A three-necked flask equipped with a stirrer, a reflux condenser, and a thermometer was charged with 0.91 g of the silicon containing alicyclic compound (2) of the above formula (2-42), 1.87 g of the silicon containing alicyclic compound (4) of the above formula (4-6) (wherein Rf is a trifluoromethyl group), 1.15 g of the silicon containing alicyclic compound (4) of the above formula (4-6) (wherein Rf is a trifluoromethyl group) by replacing the hydrogen atom of the hydroxyl group by a t-butoxycarbonyl group, 1.08 g of the silicon containing alicyclic compound (4) of the above formula (4-42), 5 g of 4-methyl-2-pentanone, and 0.78 g of a 1.75 wt % aqueous solution of oxalic acid. The mixture was reacted for ten hours at 40° C. while stirring. The reaction was terminated by cooling the flask with ice. The reaction mixture was poured into a separating funnel to remove the water layer. The organic layer was washed with ion-exchanged water until the reaction solution becomes neutral. The solvent was removed from the organic layer to obtain 3.6 g of a polymer having Mw of 1,500 and Mw/Mn of 1.1.

The polymer was dissolved in 11.4 g of 4-methyl-2-pentanone. After the addition of 1.15 g of distilled water and 1.62 g of triethylamine, the mixture was heated to 60° C. in a nitrogen stream. After five hours, the mixture was cooled with ice and stirred, then a solution of 1.35 g of oxalic acid in 50 g of distilled water was added, and stirring was continued. The reaction mixture was poured into a separating funnel to remove the water layer. The organic layer was washed with ion-exchanged water until the reaction solution becomes neutral. The solvent was removed from the organic layer to obtain the polysiloxane (1).

NMR spectrum (chemical shift σ), IR spectrum, and Mw of the polysiloxane (1) were measured to confirm the following results.

σ: 2.3 ppm (—$CH_2C(CF_3)_2$ group), 1.4 ppm (t-butyl group), 1.5 ppm (t-butoxycarbonyl group)
IR: 1774 $cm^{-1}$ (carbonic acid ester group), 1726 $cm^{-1}$ (ester group), 1226 $cm^{-1}$ (C—F bond), 1130 $cm^{-1}$ (siloxane group)
Mw: 2,400
Mw/Mn: 1.1

Evaluation Example 6

Evaluation of Radiation Transmittance

The radiation transmittance of coating films with a thickness of 100 nm prepared from the polysiloxane of Example 25–32 at wavelengths of 157 nm and 193 nm was measured. The results are shown in Table 3.

TABLE 3

| Polysiloxane | Radiation transmittance (%) | |
| --- | --- | --- |
|  | 157 nm | 193 nm |
| Polysiloxane (1) of Example 25 | 67 | 97 |
| Polysiloxane (1) of Example 25 | 67 | 97 |
| Polysiloxane (1) of Example 27 | 66 | 97 |
| Polysiloxane (1) of Example 28 | 56 | 95 |
| Polysiloxane (1) of Example 29 | 54 | 95 |
| Polysiloxane (1) of Example 30 | 52 | 94 |
| Polysiloxane (1) of Example 31 | 61 | 94 |
| Polysiloxane (1) of Example 32 | 60 | 94 |

Example 36

Radiation-sensitive Resin Composition

A solution composition was prepared by homogeneously mixing 100 parts of the polysiloxane obtained in Example 22, Example 23, Example 25–29, Example 31, Example 32 or Comparative Example 6, 1 part of triphenylphosphonium nonafluoro-n-butenesulfonate, 0.02 part of tri-n-octylamine, and 900 parts of 2-heptanone.

The solution composition was applied onto a silicon wafer substrate by spin coating and pre-baked for 90 seconds at 140° C. to form a resist film with a thickness of 100 nm.

The resist film was exposed to an ArF excimer laser (wavelength: 193 nm) or F2 excimer laser (wavelength: 157 nm) while changing the irradiation dose, post-baked for 90 seconds on a hot plate at 110° C., and then developed in a 2.38 wt % aqueous solution of tetramethylammonium hydroxide.

Observation of the exposed area on the substrate by a scanning-type electron microscope confirmed that the limit resolution are shown in Table 4.

TABLE 4

| Polysiloxane | limit resolution (μm) | |
| --- | --- | --- |
|  | ArF | F2 |
| Polysiloxane (1) of Example 22 | 0.15 | 0.07 |
| Polysiloxane (1) of Example 23 | 0.14 | 0.07 |

TABLE 4-continued

| Polysiloxane | limit resolution (μm) | |
| --- | --- | --- |
|  | ArF | F2 |
| Polysiloxane (1) of Example 25 | 0.16 | — |
| Polysiloxane (1) of Example 26 | 0.15 | 0.11 |
| Polysiloxane (1) of Example 27 | 0.15 | — |
| Polysiloxane (1) of Example 28 | 0.14 | — |
| Polysiloxane (1) of Example 29 | 0.13 | 0.08 |
| Polysiloxane (1) of Example 31 | 0.14 | — |
| Polysiloxane (1) of Example 32 | 0.13 | 0.08 |
| Polysiloxane of Comparative Example 6 | 0.30 | 0.30 |

Example 37

Preparation of Polysiloxane (3)

A three-necked flask equipped with a stirrer, a reflux condenser, and a thermometer was charged with 2.06 g of the silicon containing alicyclic compound (2) of the above formula (2-39), 2.94 g of methyltrimethoxysilane, 15 g of 4-methyl-2-pentanone, and 1.49 g of a 1.75 wt % aqueous solution of oxalic acid. The mixture was reacted for five hours at 80° C. while stirring, followed by cooling with ice to terminate the reaction. The reaction mixture was poured into a separating funnel to remove the water layer. The organic layer was washed with ion-exchanged water until the reaction solution becomes neutral. The solvent was removed from the organic layer to obtain the polysiloxane (3).

NMR spectrum (chemical shift σ), IR spectrum, and Mw of the polysiloxane (3) were measured to confirm the following results.

σ: 1.4 ppm (t-butyl group), 0.2 ppm ($SiCH_3$ group)
IR: 1705 $cm^{-1}$ (ester group), 1116 $cm^{-1}$ (siloxane group)
Mw: 2,600

Example 38

Preparation of Polysiloxane (3)

A three-necked flask equipped with a stirrer, a reflux condenser, and a thermometer was charged with 1.48 g of the silicon containing alicyclic compound (2) of the above formula (2-42), 1.52 g of the silicon containing alicyclic compound (4) of the above formula (4-6) (wherein Rf is a trifluoromethyl group), 9 g of 4-methyl-2-pentanone, and 0.51 g of a 1.75 wt % aqueous solution of oxalic acid. The mixture was reacted for six hours at 80° C. while stirring, followed by cooling to terminate the reaction. The reaction mixture was poured into a separating funnel to remove the water layer. The organic layer was washed with ion-exchanged water until the reaction solution becomes neutral. The solvent was removed from the organic layer to obtain the polysiloxane (3).

NMR spectrum (chemical shift σ), IR spectrum, and Mw of the polysiloxane (3) were measured to confirm the following results.

σ: 2.3 ppm (two $CF_3$ groups bonded to a $CH_2C$ group), 1.4 ppm (t-butyl group)
IR: 1703 $cm^{-1}$ (ester group), 1213 $cm^{-1}$ (C—F bond), 1151 $cm^{-1}$ (siloxane group)
Mw: 1,900

Example 39

Preparation of Polysiloxane (3)

A three-necked flask equipped with a stirrer, a reflux condenser, and a thermometer was charged with 0.58 g of the silicon containing alicyclic compound (2) of the above formula (2-42), 2.42 g of the silicon containing alicyclic compound (4) of the above formula (4-6) (wherein Rf is a trifluoromethyl group), 9 g of 4-methyl-2-pentanone, and 0.15 g of a 1.75 wt % aqueous solution of oxalic acid. The mixture was reacted for six hours at 80° C. while stirring, followed by cooling to terminate the reaction. The reaction mixture was poured into a separating funnel to remove the water layer. The organic layer was washed with ion-exchanged water until the reaction solution becomes neutral. The solvent was removed from the organic layer to obtain the polysiloxane (3).

NMR spectrum (chemical shift σ), IR spectrum, and Mw of the polysiloxane (3) were measured to confirm the following results.

σ: 2.3 ppm (two $CF_3$ groups bonded to a $CH_2C$ group), 1.4 ppm (t-butyl group)
IR: 1703 $cm^{-1}$ (ester group), 1213 $cm^{-1}$ (C—F bond), 1143 $cm^{-1}$ (siloxane group)
Mw: 2,400

Example 40

Preparation of Polysiloxane (3)

A three-necked flask equipped with a stirrer, a reflux condenser, and a thermometer was charged with 1.52 g of the silicon containing alicyclic compound (2) of the above formula (2-42), 1.57 g of the silicon containing alicyclic compound (4) of the above formula (4-6) (wherein Rf is a trifluoromethyl group), 1.91 g of methyltriethoxysilane, 15 g of 4-methyl-2-pentanone, and 1.31 g of a 1.75 wt % aqueous solution of oxalic acid. The mixture was reacted for six hours at 80° C. while stirring, followed by cooling to terminate the reaction. The reaction mixture was poured into a separating funnel to remove the water layer. The organic layer was washed with ion-exchanged water until the reaction solution becomes neutral. The solvent was removed from the organic layer to obtain the polysiloxane (3).

NMR spectrum (chemical shift σ), IR spectrum, and Mw of the polysiloxane (3) were measured to confirm the following results.

σ: 2.3 ppm (two $CF_3$ groups bonded to a $CH_2C$ group), 1.4 ppm (t-butyl group), 0.2 ppm ($SiCH_3$ group)
IR: 1699 $cm^{-1}$ (ester group), 1213 $cm^{-1}$ (C—F bond), 1124 $cm^{-1}$ (siloxane group)
Mw: 1,900

Example 41

Preparation of Polysiloxane (3)

A three-necked flask equipped with a stirrer, a reflux condenser, and a thermometer was charged with 1.28 g of the silicon containing alicyclic compound (2) of the above formula (2-42) 2.64 g of the silicon containing alicyclic compound (4) of the above formula (4-6) (wherein Rf is a trifluoromethyl group), 1.07 g of methyltriethoxysilane, 15 g of 4-methyl-2-pentanone, and 1.11 g of a 1.75 wt % aqueous solution of oxalic acid. The mixture was reacted for six hours at 80° C. while stirring, followed by cooling to terminate the reaction. The reaction mixture was poured into a separating funnel to remove the water layer. The organic layer was washed with ion-exchanged water until the reaction solution becomes neutral. The solvent was removed from the organic layer to obtain the polysiloxane (3).

NMR spectrum (chemical shift σ), IR spectrum, and Mw of the polysiloxane (3) were measured to confirm the following results.

σ: 2.3 ppm (two $CF_3$ groups bonded to a $CH_2C$ group), 1.4 ppm (t-butyl group), 0.2 ppm ($SiCH_3$ group)
IR: 1703 $cm^{-1}$ (ester group), 1213 $cm^{-1}$ (C—F bond), 1140 $cm^{-1}$ (siloxane group)
Mw: 2,900

Example 42

Preparation of Polysiloxane (3)

A three-necked flask equipped with a stirrer, a reflux condenser, and a thermometer was charged with 1.44 g of the silicon containing alicyclic compound (2) of the above formula (2-42), 1.60 g of the silicon containing alicyclic compound (4) of the above formula (4-6) (wherein Rf is a trifluoromethyl group), 1.95 g of methyltriethoxysilane, 15 g of 4-methyl-2-pentanone, and 1.34 g of a 1.75 wt % aqueous solution of oxalic acid. The mixture was reacted for six hours at 80° C. while stirring, followed by cooling to terminate the reaction. The reaction mixture was poured into a separating funnel to remove the water layer. The organic layer was washed with ion-exchanged water until the reaction solution becomes neutral. The solvent was removed from the organic layer to obtain the polysiloxane (3).

NMR spectrum (chemical shift σ), IR spectrum, and Mw of the polysiloxane (3) were measured to confirm the following results.

σ: 2.3 ppm (two $CF_3$ groups bonded to a $CH_2C$ group), 1.4 ppm (t-butyl group), 0.2 ppm ($SiCH_3$ group)
IR: 1699 $cm^{-1}$ (ester group), 1213 $cm^{-1}$ (C—F bond), 1124 $cm^{-1}$ (siloxane group)
Mw: 1,300

Evaluation Example 7

Evaluation of Radiation Transmittance

The radiation transmittance of coating films with a thickness of 100 nm prepared from the polysiloxanes (3) of Examples 39–42 at wavelengths of 157 nm and 193 nm was measured.

The results are shown in Table 5.

TABLE 5

| Polysiloxane | Radiation transmittance (%) | |
| --- | --- | --- |
| | 157 nm | 193 nm |
| Polysiloxane (3) of Example 39 | 52 | 98 |
| Polysiloxane (3) of Example 40 | 42 | 96 |
| Polysiloxane (3) of Example 41 | 48 | 97 |
| Polysiloxane (3) of Example 42 | 42 | 96 |

The results show that the polysiloxanes (3) exhibit superior transmittance at a wavelength less than 193 nm, particularly at 157 nm. This indicates that the polysiloxane (3) is a very useful resin in a lithography process using a short wavelength radiation such as an ArF excimer laser (wavelength: 193 nm) or F2 excimer laser (wavelength: 157 nm).

Comparative Example 7

Preparation of Comparative Polysiloxane

A three-necked flask equipped with a stirrer, a reflux condenser, and a thermometer was charged with 1.62 g of the silane compound (iii) of the formula (3), wherein R is a hydrogen atom, R' is an ethyl group, and n is 0, 1.98 g of the silicon containing alicyclic compound (4) shown by the formula (4-6), 2.41 g of methyltriethoxysilane, 6.0 g of 4-methyl-2-pentanone, and 1.65 g of a 1.75 wt % aqueous solution of oxalic acid. The mixture was reacted for six hours at 80° C. while stirring, followed by cooling with ice to terminate the reaction. The reaction mixture was poured into a separating funnel to remove the water layer. The organic layer was washed with ion-exchanged water until the reaction solution becomes neutral. The solvent was removed from the organic layer to obtain a comparative polymer.

NMR spectrum (chemical shift σ) and IR spectrum of the comparative polysiloxane were measured. The results were as follows.

σ: 2.3 ppm (two $CF_3$ groups bonded to a $CH_2C$ group), 1.5 ppm (t-butoxy group), 0.2 ppm ($SiCH_3$ group)
IR: 3400 $cm^{-1}$ (hydroxyl group), 1703 $cm^{-1}$ (carbonyl group), 1213 $cm^{-1}$ (C—F bond), 1130 $cm^{-1}$ (siloxane group), 1080 $cm^{-1}$ (siloxane group)

Evaluation Example 8

Evaluation of Glass Transition Temperature

Glass transition temperature of the polysiloxanes obtained in Example 40, Example 41, and Comparative Example 7 was measured to confirm that the glass transition temperature of these polysiloxanes was respectively 118° C., 116° C., and 94° C. These results show that the polysiloxane (3) of the formula (3) in which n'=1 has a higher glass transition temperature than the polysiloxane of the formula (3) in which n'=0, and is more useful as a material for forming fine rectangular resist patterns by a conventional lithography process.

Example 43

Radiation-sensitive Resin Composition

A solution composition was prepared by homogeneously mixing 100 parts of the polysiloxane (3) obtained in Example 40, 1 part of triphenylsulfonium trifluoromethane sulfonate, 0.02 part of tri-n-octylamine, 900 parts of 2-heptanone.

The solution composition was applied onto a silicon wafer substrate by spin coating and pre-baked for 90 seconds at 130° C. to form a resist film with a thickness of 100 nm.

The resist film was exposed to a KrF excimer laser through a photo mask while changing the irradiation dose, post-baked for 90 seconds on a hot plate at 110° C., and then developed in a 2.38 wt % aqueous solution of tetramethylammonium hydroxide to form a resist pattern.

The exposed area on the substrate was observed by an electronic microscope to confirm that the patterns were resolved to a line size as fine as 0.24 µm and maintained a rectangular configuration.

Resist patterns were prepared and evaluated in the same manner as above except for using the polysiloxane (3) obtained in Example 41 instead of the polysiloxane (3) obtained in Example 40, to confirm that the patterns were resolved to a line size as fine as 0.24 µm, with the pattern configuration maintaining a rectangle.

Comparative Example 8

Comparative Radiation-sensitive Resin Composition

Resist patterns were formed and evaluated in the same manner as above except for using the polysiloxane of Comparative Example 7 in place of the polysiloxane (3) of Example 40, to confirm that the patterns were resolved to a line width as fine as 0.3 µm, but did not maintain a rectangular configuration.

Example 44

Radiation-sensitive Resin Composition

A solution composition was prepared by homogeneously mixing 100 parts of the polysiloxane (3) obtained in Example 40, 1 part of triphenylsulfonium trifluoromethane sulfonate, 0.02 part of tri-n-octylamine, 900 parts of 2-heptanone.

The solution composition was applied onto a silicon wafer substrate by spin coating and pre-baked for 90 seconds at 130° C. to form a resist film with a thickness of 100 nm.

The resist film was exposed to an F2 excimer laser through a photo mask while changing the irradiation dose, post-baked for 90 seconds on a hot plate at 110° C., and then developed in a 2.38 wt % aqueous solution of tetramethylammonium hydroxide to form a resist pattern.

The exposed area on the substrate was observed by an electronic microscope to confirm that the patterns were resolved to a line size as fine as 0.10 µm and maintained a rectangular configuration.

Resist patterns were formed and evaluated in the same manner as above except for using the polysiloxane (3) obtained in of Comparative Example 7 in place of the polysiloxane (3) of Example 40, to confirm that the patterns were resolved to a line width as fine as 0.10 µm and maintained a rectangular configuration.

Example 45

Synthesis of Silicon-containing Alicyclic Compound (4)

A three-necked flask equipped with a stirrer, a reflux condenser, and a thermometer was charged with 13.4 g of trimethoxysilane and 20.0 g of 5-[2-hydroxy-2,2-di(trifluoromethyl)ethyl]-bicyclo[2.2.1]hept-2-ene. The mixture was stirred at room temperature and 0.2 ml of a 0.2 mol chloroplatinic acid ($H_2PtCl_6$) solution in isopropyl alcohol was added to initiate the reaction. The reaction was continued for 48 hours at 100° C. while refluxing. The reaction mixture was allowed to cool to room temperature, diluted with n-hexane, and filtered through celite by suction. The solvent was evaporated by distillation under vacuum to obtain a crude product. The crude product was purified by vacuum distillation at 2 mmHg and a temperature of 110° C. to obta 12.2 g of the reaction product.

This reaction product was identified to be the silicon containing alicyclic compound (4) of the formula (4-3) (in which Rf is a trifluoromethyl group) by the measurement of $^1$H-NMR spectrum (chemical shift σH), $^{13}$C-NMR spectrum (chemical shift σC), $^{29}$Si—NMR spectrum (chemical shift σSi), $^{19}$F-NMR spectrum (chemical shift σF), IR spectrum, and mass spectrum (FABMS)

σH: 3.6 ppm (methoxy group)
σC: 123 ppm (trifluoromethyl group), 51 ppm (methoxy group)
σSi: −45 ppm
σF: −76 to −79 ppm
IR: 3400 cm$^{-1}$ (hydroxyl group), 2847 cm$^{-1}$ (methoxy group), 1217 cm$^{-1}$ (C—F bond), 1097 cm$^{-1}$ (siloxane group)
FABMS: m/z=397 (M$^+$+1)

Example 46

Synthesis of Silicon-containing Alicyclic Compound (4)

A three-necked flask equipped with a stirrer, a reflux condenser, and a thermometer was charged with 38.8 g of triethoxysilane and 43.2 g of 5-[2-hydroxy-2,2-di(trifluoromethyflethyl]-bicyclo[2.2.1]hept-2-ene. The mixture was stirred at room temperature and 0.1 ml of a 0.2 mol chloroplatinic acid (H$_2$PtCl$_6$) solution in isopropyl alcohol was added to initiate the reaction. The reaction was continued for 30 hours at 100° C. while refluxing. The reaction mixture was allowed to cool to room temperature, diluted with n-hexane, and filtered through celite by suction. The solvent was evaporated by distillation under vacuum to obtain a crude product. The crude product was purified by vacuum distillation at 3 mmHg and a temperature of 105° C. to obtain 59.8 g of the reaction product.

As the result shown below, this reaction product was identified to be the silicon containing alicyclic compound (4) of the formula (4-6) (in which Rf is a trifluoromethyl group) by the measurement of $^1$H-NMR spectrum (chemical shift σH), $^{13}$C-NMR spectrum (chemical shift σC), $^{29}$Si—NMR spectrum (chemical shift σSi), $^{19}$F-NMR spectrum (chemical shift σF), IR spectrum, and mass spectrum (FABMS).
σH: 3.8 ppm (ethoxy group), 1.2 ppm (ethoxy group)
σC: 123 ppm (trifluoromethyl group), 59 ppm (ethoxy group), 18 ppm (methyl group)
σSi: −48 ppm
σF: −76 to −79 ppm
IR: 3400 cm$^{-1}$ (hydroxyl group), 2878 cm$^{-1}$ (methoxy group), 1215 cm$^{-1}$ (C—F bond), 1082 cm$^{-1}$ (siloxane group)
FABMS: m/z=439 (M$^+$+1)

Example 47

Synthesis of Silicon-containing Alicyclic Compound (4)

A three-necked flask equipped with a stirrer, a reflux condenser, and a thermometer was charged with 3.0 g of the silicon containing alicyclic compound (4) obtained in Example 46, and 10 ml of tetrahydrofuran. The mixture was stirred in a nitrogen stream while cooling with ice. When the mixture was cooled to 5° C., 16.7 mg of 4-dimethylaminopyridine was added and a solution of 1.64 g of di-t-butyldicarbonate in 5 ml of tetrahydrofuran was added dropwise over 15 minutes. After the addition, the mixture was stirred for one hour, allowed to cool to room temperature, and stirred for a further five hours. After the addition of 50 ml of n-hexane, the reaction mixture was poured into a separating funnel. The organic layer was washed three times with ice-cooled water. The reaction mixture was charged into a beaker and dried over anhydrous magnesium sulfate, then the solvent was evaporated under vacuum to obtain a crude product. The crude product was purified by silica gel column chromatography to obtain 3.5 g of the compound from the n-hexane fraction.

As shown by the following results of measurement of $^1$H-NMR spectrum (chemical shift σH), $^{13}$C-NMR spectrum (chemical shift σC), $^{29}$Si—NMR spectrum (chemical shift σSi), $^{19}$F-NMR spectrum (chemical shift σF), IR spectrum, and mass spectrum (FABMS), this reaction product was identified to be the silicon containing alicyclic compound (4) derived from the compound of the formula (4-6) (in which Rf is a trifluoromethyl group) by replacing the hydrogen atom of the hydroxyl group with a t-butoxycarbonyl group.
σH: 3.8 ppm (ethoxy group), 1.2 ppm (ethoxy group), 1.5 ppm (t-butyl group)
σC: 149 ppm (carbonate group), 122 ppm (trifluoromethyl group), 85 ppm (t-butoxy group), 59 ppm (ethoxy group), 28 ppm (t-butyl group), 18 ppm (methyl group)
σSi: −48 ppm
σF: −72.7 to −73.3 ppm
IR: 3400 cm$^{-1}$ (hydroxyl group), 2879 cm$^{-1}$ (methoxy group), 1774 cm$^{-1}$ (carbonate group), 1221 cm$^{-1}$ (C—F bond), 1082 cm$^{-1}$ (siloxane group)
FABMS: m/z=539 (M$^+$+1)

Example 48

Synthesis of Silicon-containing Alicyclic Compound (4)

A three-necked flask equipped with a stirrer, a dropping funnel, and a thermometer was charged with 10 g of the silicon containing alicyclic compound (4) obtained in Example 45 and 50 ml of tetrahydrofuran. The mixture was stirred in a nitrogen stream while cooling with ice. When the mixture was cooled to 5° C., 48.4 mg of 4-dimethylaminopyridine was added and a solution of 4.75 g of di-t-butyldicarbonate in 10 ml of tetrahydrofuran was added dropwise over 20 minutes. After the addition, the mixture was stirred for one hour, allowed to cool to room temperature, and stirred for a further five hours. After the addition of 100 ml of n-hexane, the reaction mixture was poured into a separating funnel. The organic layer was washed three times with ice-cooled water. The reaction mixture was charged into a beaker and dried over anhydrous magnesium sulfate, then the solvent was evaporated under vacuum to obtain 10.3 g of the product.

As shown by the following results of $^1$H-NMR spectrum (chemical shift σH) and IR spectrum measurement, this reaction product was identified to be the silicon containing alicyclic compound (4) derived from the compound of the formula (4-3) (in which Rf is a trifluoromethyl group) by replacing the hydrogen atom of the hydroxyl group with a t-butoxycarbonyl group.
σH: 3.6 ppm (methoxy group), 1.5 ppm (t-butoxycarbonyl group)
IR: 1770 cm$^{-1}$ (carbonate group), 1220 cm$^{-1}$ (C—F bond), 1098 cm$^{-1}$ (siloxane group)

Example 49

Synthesis of Silicon-containing Alicyclic Compound (4)

A three-necked flask equipped with a stirrer, a retlux condenser, and a thermometer was charged with 18.1 g of triethoxysilane and 25.0 g of [-2-hydroxy-2,2-di(trifluoromethyl)]-tetracyclo[4.4.0.1$^{2,5}$.1$^{7,10}$]dodec-3-ene.

The mixture was stirred at room temperature and 0.2 ml of a 0.2 mol chloroplatin "Lc acid ($H_2PtCl_6$) solution in isopropyl alcohol was added to initiate the reaction. The reaction was continued for 70 hours at 15° C. while refluxing. The reaction mixture was allowed to cool to room temperature, diluted with n-hexane, and filtered through celite by suction. The solvent was removed from the filtrate by evaportion under vacuum to obtain a crude product. The crude product was purified by silica gel column chromatography to obtain 19.4 g of the compound from the n-hexane fraction.

As shown by the following results of $^1$H-NMR spectrum (chemical shift σH) and IR spectrum measurement, this reaction product was identified to be the silicon containing alicyclic compound (4) of the formula (4-42) (in which Rf is a trifluoromethyl group).

σH: 3.8 ppm (ethoxy group), 1.2 ppm (ethoxy group)
IR: 3400 cm$^{-1}$ (hydroxyl group), 1220 cm$^{-1}$ (C—F bond), 1098 cm$^{-1}$ (siloxane group)

Example 50

Synthesis of Silicon-containing Alicyclic Compound (4)

A three-necked flask equipped with a stirrer, a dropping funnel, and a thermometer was charged with 3 g of the silicon containing alicyclic compound (4) obtained in Example 49 and 10 ml of tetrahydrofuran. The mixture was stirred in a nitrogen stream while cooling with ice. When the mixture was cooled to 5° C., 4.5 mg of 4-dimethylaminopyridine was added and solution of 1.43 g of di-t-butyldicarbonate in 5 ml of tetrahydrofuran was added dropwise over 15 minutes. After the addition, the mixture was stirred for one hour, allowed to cool to room temperature, and stirred for a further five hours. After the addition of 50 ml of n-hexane, the reaction mixture was poured into a separating funnel. The organic layer was washed three times with ice-cooled water. The reaction mixture was charged into a beaker and dried over anhydrous magnesium sulfate, then the solvent was evaporated under vacuum to obtain a crude product. The crude product was purified by silica gel column chromatography to obtain 3.2 g of the compound from the n-hexane fraction.

As shown by the following results of $^1$H-NMR spectrum (chemical shift σH) and IR spectrum measurement, this reaction product was identified to be the silicon containing alicyclic compound (4) derived from the compound of the formula (4-42) (in which Rf is a trifluoromethyl group) by replacing the hydrogen atom of the hydroxyl group with a t-butoxycarbonyl group.

σH: 3.8 ppm (ethoxy group), 1.5 ppm (t-butoxycarbonyl group), 1.2 ppm (ethoxy group)
IR: 1771 cm$^{-1}$ (carbonate group), 1218 cm$^{-1}$ (C—F bond), 1098 cm$^{-1}$ (siloxane group)

Example 51

Synthesis of Silicon-containing Alicyclic Compound (4)

A three-necked flask equipped with a stirrer, a reflux condenser, and a thermometer was charged with 13.8 g of diethoxymethylsilane and 40.0 g of 5-(2,2,-trifluoro-1-ethyl-1-hydroxethyl)-bicyclo[2.2.1]hept-2-ene. The mixture was stirred at room temperature and 0.2 ml of a 0.2 mol chioro-platinic acid ($H_2PtCl_6$) solution in isopropyl alcohol was added to initiate the reaction. After heating at 100° C. for 48 hours while refluxing, the reaction mixture was allowed to cool to room temperature, diluted with n-hexane, and filtered through celite by suction. The solvent was removed from the filtrate by evaporation under vacuum to obtain crude product. The crude product was purified by vacuum distillation at 3 mmHg and a temperature of 98° C. to obtain 41 g of the reaction product.

As shown by the following results of $^1$H-NMR spectrum (chemical shift σH) and IR spectrum measurement, this reaction product was identified to be the silicon containing alicyclic compound (4) of the formula (4-5) (in which Rf is a trifluoromethyl group).

σH: 3.8 ppm (ethoxy group), 1.2 ppm (ethoxy group), 0.2 ppm ($SiCH_3$ group)
IR: 3400 cm$^{-1}$ (hydroxyl group), 1218 cm$^{-1}$ (C—F bond), 1098 cm$^{-1}$ (siloxane group)

Example 52

Synthesis of Silicon-containing Alicyclic Compound (4)

A three-necked flask equipped with a stirrer, a reflux condenser, and a thermometer was charged with 12.0 g of methyihydrocyclosiloxane and 54.8 g of 5.-[2-hydroxy-2,2-di(trifluoromethyl)]bicyclo[2.2.1]hept-2-ene. The mixture was stirred at room temperature and 5.0 ml of a 0.2 mol chioroplatinic acid ($H_2PtCl_6$) solution in isopropyl alcohol was added to initiate the reaction. The reaction was continued for 100 hours at 150° C. while refluxing. The reaction mixture was allowed to cool to room temperature, diluted with n-hexane, and filtered through celite by suction. The solvent was removed from the filtrate by evaporation under vacuum to obtain 66.0 g of the product.

As shown by the following results of $^1$H-NMR spectrum (chemical shift σH) and IR spectrum measurement, this reaction product was identified to be the silicon containing alicyclic compound (4) of the formula (4-91) (in which the unit number of —Si($CH_3$)O— is 4).

σH: 0.2 ppm ($SiCH_3$ group)
IR: 3400 cm$^{-1}$ (hydroxyl group), 2847 cm$^{-1}$ (methoxy group), 1218 cm$^{-1}$ (C—F bond), 1098 cm$^{-1}$ (siloxane group)

Example 53

Synthesis of Silicon-containing Alicyclic Compound (4)

A three-necked flask equipped with a stirrer, a dropping funnel, and a thermometer was charged with 5 g of the compound obtained in Example 52 and 15 ml of tetrahydrofuran. The mixture was stirred in a nitrogen stream while cooling with ice. When the mixture was cooled to 5° C., 36.6 mg of 4-dimethylaminopyridine was added and a solution of 3.6 g of di-t-butyldicarbonate in 5 ml of tetrahydrofuran was added dropwise over 15 minutes. After the addition, the mixture was stirred for one hour, allowed to cool to room temperature, and stirred for a further five hours. After the addition of 70 ml of n-hexane, the reaction mixture was poured into a separating funnel. The organic layer was washed three times with ice-cooled water. The reaction mixture was charged into a beaker and dried over anhydrous magnesium sulfate, then the solvent was removed by distillation under vacuum to obtain 5.5 g of a product.

As shown by the following results of $^1$H-NMR spectrum (chemical shift σH) measurement, this reaction product was identified to be the silicon containing alicyclic compound (4)

derived from the compound of the formula (4-91) (in which the unit number of —Si(CH$_3$)O— is 4) by replacing the hydrogen atom of the hydroxyl group in the compound with a t-butoxycarbonyl group.

σ: 1.5 ppm (t-butoxycarbonyl group), 0.2 ppm (SiCH$_3$ group)

Example 54

A three-necked flask equipped with a stirrer, a reflux condenser, and a thermometer was charged with 10 g of methylhydrocyclosiloxane and 56.7 g of 8-[2-hydroxy-2,2-di(trifluoromethyl)]tetracyclo-[4.4.0.1$^{2,5}$.1$^{7,10}$]dodec-3-ene. The mixture was stirred at room temperature and 5.0 ml of a 0.2 mol chloroplatinic acid (H$_2$PtCl$_6$) solution in isopropyl alcohol was added to initiate the reaction. The reaction was continued for 100 hours a 150° C. while refluxing. The reaction mixture was allowed to cool to room temperature, diluted with n-hexane, and filtered through celite by suction. The solvent was removed from the filtrate by evaporation under vacuum to obtain 65.4 g of the product.

As shown by the following results of $^1$H-NMR spectrum (chemical shift σH) and IR spectrum measurement, this reaction product was identified to be the silicon containing alicyclic compound (4) of the formula (4-97) (in which the unit number of —Si(CH$_3$)O— is 4).

σH: 0.2 ppm (SiCH$_3$ group)
IR: 3400 cm$^{-1}$ (hydroxyl group), 2849 cm$^{-1}$ (methoxy group), 1220 cm$^{-1}$ (C—F bond), 1100 cm$^{-1}$ (siloxane group)

Example 55

Synthesis of Silicon-containing Alicyclic Compound (4)

A three-necked flask equipped with a stirrer, a dropping funnel, and a thermometer was charged with 5.0 g of the silicon containing alicyclic compound (4) obtained in Example 54 and 15 ml of tetrahydrofuran. The mixture was stirred in a nitrogen stream while cooling with ice. When the mixture was cooled to 5° C., 30.5 mg of 4-dimethylaminopyridine was added and a solution of 3.0 g of di-t-butyldicarbonate in 5 ml of tetrahydrofuran was added dropwise over 15 minutes. After the addition, the mixture was stirred for one hour, allowed to cool to room temperature, and stirred for a further five hours. After the addition of 70 ml of n-hexane, the reaction mixture was poured into a separating funnel. The organic layer was washed three times with ice-cooled water. The reaction mixture was charged into a beaker and dried over anhydrous magnesium sulfate, then the solvent was removed by distillation under vacuum to obtain 5.3 g of a product.

As shown by the following results of $^1$H-NMR spectrum (chemical shift σH) measurement, this reaction product was identified to be the silicon containing alicyclic compound (4) derived from the compound of the formula (4-97) (in which the unit number of —Si(CH$_3$)O— is 4) by replacing the hydrogen atom of the hydroxyl group in the compound with a t-butoxycarbonyl group.

σ: 1.5 ppm (t-butoxycarbonyl group), 0.2 ppm (SiCH$_3$ group)

Example 56

Preparation of Polysiloxane (5)

A three-necked flask equipped with a stirrer, a reflux condenser, and a thermometer was charged with 2.5 g of the silicon containing alicyclic compound (4) shown by the above formula (4-6) (wherein Rf is a trifluoromethyl group), 2.5 g of 4-methyl-2-pentanone, and 0.42 g of 1.75 wt % oxalic acid aqueous solution. The mixture was reacted for six hours at 80° C. while stirring. The reaction was terminated by cooling the flask with ice. The reaction mixture was poured into a separating funnel to remove the water layer. The organic layer was washed with water until the reaction solution becomes neutral and the solvent was removed by distillation under vacuum to obtain polysiloxane (5).

$^1$H-NMR spectrum (chemical shift σH), IR spectrum, and Mw of the polysiloxane (5) were measured. The results were as follows.

σH: 2.3 ppm (CH$_2$C(CF$_3$)$_2$ group)
IR: 3400 cm$^{-1}$ (hydroxyl group), 1221 cm$^{-1}$ (C—F bond), 1130 cm$^{-1}$ (siloxane group), 1080 cm$^{-1}$ (siloxane group)
Mw: 3,300

Example 57

Preparation of Polysiloxane (5)

A three-necked flask equipped with a stirrer, a reflux condenser, and a thermometer was charged with 1.5 g of the silicon containing alicyclic compound (4) derived from the compound of the above formula (4-6) (wherein Rf is a trifluoromethyl group) by replacing the hydrogen atom of the hydroxyl group by a t-butoxycarbonyl group, 1.5 g of 4-methyl-2-pentanone, and 0.20 g of 1.75 wt % oxalic acid aqueous solution. The mixture was reacted for five hours at 80° C. while stirring. The reaction was terminated by cooling the flask with ice. The reaction mixture was poured into a separating funnel to remove the water layer. The organic layer was washed with water until the reaction solution becomes neutral and the solvent was removed by distillation under vacuum to obtain polysiloxane (5).

$^1$H-NMR spectrum (chemical shift σH), IR spectrum, and Mw of the polysiloxane (5) were measured. The results were as follows.

σ: 2.3 ppm (CH$_2$C(CF$_3$)$_2$ group), 1.5 ppm (t-butoxycarbonyl group)
IR: 1774 cm$^{-1}$ (carbonate group), 1217 cm$^{-1}$ (C—F bond), 1132 cm$^{-1}$ (siloxane group), 1082 cm$^{-1}$ (siloxane group)
Mw: 7,500

Example 58

Preparation of Polysiloxane (5)

A three-necked flask equipped with a stirrer, a reflux condenser, and a thermometer was charged with 1.98 g of the silicon containing alicyclic compound (4) shown by the above formula (4-6) (wherein Rf is a trifluoromethyl group), 1.62 g of 2-t-butoxycarbonylethyltriethoxysilane, 2.41 g of methyltriethoxysilane, 6.0 g of 4-methyl-2-pentanone, and 1.65 g of 1.75 wt % oxalic acid aqueous solution. The mixture was reacted for six hours at 80° C. while stirring. The reaction was terminated by cooling the flask with ice. The reaction mixture was poured into a separating funnel to remove the water layer. The organic layer was washed with water until the reaction solution becomes neutral and the solvent was removed by distillation under vacuum to obtain polysiloxane (5).

¹H-NMR spectrum (chemical shift σH), IR spectrum, and Mw of the polysiloxane (5) were measured. The results were as follows.

σ: 2.3 ppm (CH$_2$C(CF$_3$)$_2$ group), 1.5 ppm (t-butoxy group), 0.2 ppm (SiCH$_3$ group)

IR: 3400 cm$^{-1}$ (hydroxyl group), 1703 cm$^{-1}$ (carbonyl group), 1213 cm$^{-1}$ (C—F bond), 1130 cm$^{-1}$ (siloxane group), 1080 cm$^{-1}$ (siloxane group)

Mw: 2,500

Example 59

Preparation of Polysiloxane (5)

A three-necked flask equipped with a stirrer, a reflux condenser, and a thermometer was charged with 4.0 g of the silicon containing alicyclic compound (4) shown by the above formula (4-42) (wherein Rf is a trifluoromethyl group), 4.0 g of 4-methyl-2-pentanone, and 0.58 g of 1.75 wt % oxalic acid aqueous solution. The mixture was reacted for six hours at 80° C. while stirring. The reaction was terminated by cooling the flask with ice. The reaction mixture was poured into a separating funnel to remove the water layer. The organic layer was washed with water until the reaction solution becomes neutral and the solvent was removed by distillation under vacuum to obtain polysiloxane (5).

¹H-NMR spectrum (chemical shift σH), IR spectrum, and Mw of the polysiloxane (5) were measured. The results were as follows.

σH: 2.3 ppm (CH$_2$C(CF$_3$)$_2$ group)

IR: 3400 cm$^{-1}$ (hydroxyl group), 1220 cm$^{-1}$ (C—F bond), 1130 cm$^{-1}$ (siloxane group), 1080 cm$^{-1}$ (siloxane group)

Mw: 2,200

Example 60

Preparation of Polysiloxane (5)

A three-necked flask equipped with a stirrer, a reflux condenser, and a thermometer was charged with 5.0 g of the silicon containing alicyclic compound (4) derived from the compound of the above formula (4-42) (wherein Rf is a trifluoromethyl group) by replacing the hydrogen atom of the hydroxyl group by a t-butoxycarbonyl group, 5.0 g of 4-methyl-2-pentanone, and 0.61 g of 1.75 wt % oxalic acid aqueous solution. The mixture was reacted for six hours at 80° C. while stirring. The reaction was terminated by cooling the flask with ice. The reaction mixture was poured into a separating funnel to remove the water layer. The organic layer was washed with water until the reaction solution becomes neutral and the solvent was removed by distillation under vacuum to obtain polysiloxane (5).

¹H-NMR spectrum (chemical shift σH), IR spectrum, and Mw of the polysiloxane (5) were measured. The results were as follows.

σ: 2.3 ppm (CH$_2$C(CF$_3$)$_2$ group), 1.5 ppm (t-butoxycarbonyl group)

IR: 1775 cm$^{-1}$ (carbonate group), 1220 cm$^{-1}$ (C—F bond), 1130 cm$^{-1}$ (siloxane group), 1130 cm$^{-1}$ (siloxane group)

Mw: 2,400

Example 61

Preparation of Polysiloxane (5)

A three-necked flask equipped with a stirrer, a reflux condenser, and a thermometer was charged with 4.0 g of the silicon containing alicyclic compound (4) shown by the above formula (4-5) (wherein Rf is a trifluoromethyl group), 15.0 g of 4-methyl-2-pentanone, and 0.72 g of 1.75 wt % oxalic acid aqueous solution. The mixture was reacted for six hours at 80° C. while stirring. The reaction was terminated by cooling the flask with ice. The reaction mixture was poured into a separating funnel to remove the water layer. The organic layer was washed with water until the reaction solution becomes neutral and the solvent was removed by distillation under vacuum to obtain polysiloxane (5).

¹H-NMR spectrum (chemical shift σH), IR spectrum, and Mw of the polysiloxane (5) were measured. The results were as follows.

σH: 2.3 ppm (CH$_2$C(CF$_3$)$_2$ group), 0.2 ppm (SiCH$_3$ group)

IR: 3400 cm$^{-1}$ (hydroxyl group), 1220 cm$^{-1}$ (C—F bond), 1130 cm$^{-1}$ (siloxane group), 1080 cm$^{-1}$ (siloxane group)

Mw: 2,200

Example 62

Preparation of Polysiloxane (5)

A three-necked flask equipped with a stirrer, a reflux condenser, and a thermometer was charged with 2.22 g of the silicon containing alicyclic compound shown by the above formula (4-91) (in which the unit number of —Si(CH$_3$)O— is 4), 2.78 g of methyltriethoxysilane, 5.0 g of 4-methyl-2-pentanone, and 1.41 g of 1.75 wt % oxalic acid aqueous solution. The mixture was reacted for six hours at 80° C. while stirring. The reaction was terminated by cooling the flask with ice. The reaction mixture was poured into a separating funnel to remove the water layer. The organic layer was washed with water until the reaction solution becomes neutral and the solvent was removed by distillation under vacuum to obtain polysiloxane (5).

¹H-NMR spectrum (chemical shift σH), IR spectrum, and Mw of the polysiloxane (5) were measured. The results were as follows.

σH: 2.3 ppm (CH$_2$C(CF$_3$)$_2$ group), 0.2 ppm (SiCH$_3$ group)

IR: 3400 cm$^{-1}$ (hydroxyl group), 1221 cm$^{-1}$ (C—F bond), 1131 cm$^{-1}$ (siloxane group), 1078 cm$^{-1}$ (siloxane group)

Mw: 3,300

Example 63

Preparation of Polysiloxane (5)

A three-necked flask equipped with a stirrer, a reflux condenser, and a thermometer was charged with 2.48 g of the compound derived from the compound shown by the above formula (4-91) (in which the unit number of —Si(CH$_3$)O— is 4) by replacing the hydrogen atom of the hydroxyl group by a t-butoxycarbonyl group, 2.52 g of methyltriethoxysilane, 5.0 g of 4-methyl-2-pentanone, and 1.28 g of 1.75 wt % oxalic acid aqueous solution. The mixture was reacted for six hours at 80° C. while stirring. The reaction was terminated by cooling the flask with ice. The reaction mixture was poured into a separating funnel to remove the water layer. The organic layer was washed with water until the reaction solution becomes neutral and the solvent was removed by distillation under vacuum to obtain a resin.

¹H-NMR spectrum (chemical shift σH), IR spectrum, and Mw of the resin were measured. The results were as follows.

σ: 2.3 ppm (CH$_2$C(CF$_3$)$_2$ group), 1.5 ppm (t-butoxy group), 0.2 ppm (SiCH$_3$ group)

IR: 1775 cm$^{-1}$ (carbonate group), 1221 cm$^{-1}$ (C—F bond), 1131 cm$^{-1}$ (siloxane group), 1078 cm$^{-1}$ (siloxane group)

Mw: 3,500

Comparative Example 9

Preparation of Comparative Polysiloxane

A three-necked flask equipped with a stirrer, a reflux condenser, and a thermometer was charged with 20 g of 2-t-butoxycarbonylethyltriethoxysilane, 60 g of 4-methyl-2-pentanone, and 4.09 g of 1.75 wt % oxalic acid aqueous solution. The mixture was reacted for six hours at 80° C. while stirring. The reaction was terminated by cooling the flask with ice. The reaction mixture was poured into a separating funnel to remove the water layer. The organic layer was washed with water until the reaction solution becomes neutral and the solvent was removed by distillation under vacuum to obtain a comparative polysiloxane.

$^1$H-NMR spectrum (chemical shift σH), IR spectrum, and Mw of the comparative polysiloxane were measured. The results were as follows.

σ: 1.5 ppm (t-butoxycarbonyl group)
IR: 3400 cm$^{-1}$ (hydroxyl group), 1703 cm$^{-1}$ (carbonyl bond), 1130 cm$^{-1}$ (siloxane group), 1080 cm$^{-1}$ (siloxane group)
Mw: 2,700

Evaluation Example 9

Evaluation of Radiation Transmittance

The radiation transmittance of coating films with a thickness of 100 nm prepared from the polysiloxanes (5) of Examples 56–59, Example 61, and Comparative Example 9 at wavelengths of 157 nm and 193 nm was measured. The results are shown in Table 6.

TABLE 6

| Polysiloxane | Radiation transmittance (%) | |
| --- | --- | --- |
| | 157 nm | 193 nm |
| Polysiloxane (5) of Example 56 | 69 | 98 |
| Polysiloxane (5) of Example 57 | 61 | 96 |
| Polysiloxane (5) of Example 58 | 46 | 97 |
| Polysiloxane (5) of Example 59 | 66 | 97 |
| Polysiloxane (5) of Example 61 | 67 | 97 |
| Polysiloxane of Comparative Example 9 | 30 | 95 |

The results in the above table shows that the polysiloxanes (5) having a polysiloxane structure for the basic skeleton exhibited radiation transmittance at a wavelength of 193 nm equivalent to or higher than the comparative polysiloxane obtained in Comparative Example 9.

With regard to radiation transmittance at a wavelength of 157 nm, the comparative polysiloxane obtained in Comparative Example 9 exhibited 30% radiation transmittance, whereas the polysiloxanes (5) obtained in Examples 56–59, and Example 61 was found to exhibit radiation transmittance higher than that of the comparative polysiloxane obtained in Comparative Example 9. Conventionally, the radiation transmittance at a wavelength of 157 nm has been thought to decrease as the proportion of hydrocarbon structures in a polysiloxane increases. The results of the measurement, however, indicated that notwithstanding a comparatively large proportion of hydrocarbon structures and varied partial structures in the polymer the polysiloxane (5) exhibited high radiation transmittance at a wavelength of 157 nm.

Evaluation Examples 10

Evaluation of Alkali Solubility

A solution of each polysiloxane (5) obtained in Example 56, Example 59, or Example 61 in 2-heptanone was applied onto a silicon wafer substrate by spin coating and treated with heat on a hot plate maintained at a temperature of 130° C. for 90 seconds to form a coating film with a thickness of 100 nm.

Each film was soaked in ion-exchanged water for 60 seconds to confirm that there was almost no change in the film thickness. On the other hand, a test of soaking the films in a 2.38 wt % tetramethylammonium hydroxide aqueous solution for 60 seconds revealed that the coating films were dissolved in the solution and completely removed from the substrate.

As a result, the polysiloxane (5) was confirmed to exhibit no solubility or low solubility in ion-exchanged water, but exhibit high solubility in a common alkaline developer, demonstrating its sufficient usefulness as a resin component in chemically amplified resists.

Example 64

Radiation-sensitive Resin Composition

A solution composition was prepared by homogeneously mixing 100 parts of the polysiloxane (5) obtained in Example 57 or Example 58, 1 part of triphenylsulfonium trifluoromethanesulfonate, 0.02 part of tri-n-octylamine, and 900 parts of 2-heptanone.

The solution composition was applied onto a silicon wafer substrate by spin coating and treated with heat on a hot plate maintained at a temperature of 130° C. for 90 seconds a resist film with a thickness of 100 nm.

The resist film was exposed to an ARF excimer laser (wavelength: 193 nm) while changing the irradiation dose, heat-treated for 90 seconds on a hot plate maintained at a temperature of 110° C., and then developed in a 2.38 wt % aqueous solution of tetramethylammonium hydroxide, thereby forming resist patterns.

As a result observation of the resist patterns using a scanning electron microscope, polysiloxane (5) obtained in. Example 57 exhibited resolution to a degree of a line width of as small as 0.30 μm, and the polysiloxane (5) obtained in Example 58 as small as 0.15 μm.

Synthetic Example 2

Synthesis of Silicon-containing Alicyclic Compound

A three-necked flask equipped with a stirrer, a reflux condenser, and a thermometer was charged with 365 g of triethoxysilane and 200 g of bicyclo[2.2.1]hept-2-ene. the mixture was stirred at room temperature and 4.0 ml of a 0.2 mol chioroplatinic acid (H$_2$PtCl$_6$) solution in sopropyl alcohol was added to initiate the reaction. The reaction was continue for 90 hours at 160° C. while refluxing. The reaction mixture was allowed to cool to room temperature, diluted with n-hexane, and filtered through celite by suction. The solvent was evaporated by distillation under vacuum to obtain a crude product. The crude product was purified by vacuum distillation at 3.0 mmHg and a temperature of 82° C. to obtain 252 g of the silicon containing alicyclic compound of the formula (12-1).

(12-1)

Synthetic Example 3

Synthesis of Silicon-containing Alicyclic Compound)

A three-necked flask equipped with a stirrer, a reflux condenser and a thermometer was charged with 118 g of triethoxysilane and 100 g of tetracyclo[$4.4.0.1^{2,5}.1^{7,10}$] dodec-3-ene. The mixture was stirred at room temperature and 4.0 ml of a 0.2 mol chioroplatinic acid ($H_2PtCl_6$) solution in isopropyl alcohol was added to initiate the reaction. The reaction was continued for 90 hours at 160° C. while refluxing. The reaction mixture was allowed to cool to room temperature, diluted with n-hexane, and filtered through celite by suction. The solvent was evaporated by distillation under vacuum to obtain a crude product. The crude product was purified by vacuum distillation at 1.5 mmHg and a temperature of 133° C. to obtain 68 g of the silicon containing alicyclic compound of the formula (12-2).

Example 65

Preparation of Polysiloxane (1)

A three-necked flask equipped with a stirrer, a reflux condenser, and a thermometer was charged with 7.00 g of the silicon containing alicyclic compound (2) of the above formula (2-42), 14.47 g of the silicon containing alicyclic compound (4) of the above formula (4-6), (wherein Rf is a trifluoromethyl group), 8.52 g of the silicon containing alicyclic compound of the above formula (12–1), 30 g of 4-methyl-2-pentanone, and 6.05 g of a 1.75 wt % aqueous solution of oxalic acid. The mixture was reacted for six hours at 80° C. while stirring. The reaction was terminated by cooling the flask with ice. The reaction mixture was poured into a separating funnel to remove the water layer. The organic layer was washed with ion-exchanged water until the reaction solution becomes neutral. The solvent was removed from the organic layer to obtain the polysiloxane (1).

NMR spectrum (chemical shift σ) and Mw of the polysiloxane (1) were measured to confirm the following results.
σ: 2.3 ppm (—$CH_2C(CF_3)_2$ group), 1.4 ppm (t-butyl group)
Mw: 1,400

Example 66

Preparation of Polysiloxane (1)

A three-necked flask equipped with a stirrer, a reflux condenser, and a thermometer was charged with 1.28 g of the silicon containing alicyclic compound (2) of the above formula (2-42), 2.20 g of the silicon containing alicyclic compound (4) of the above formula (4-6), (wherein Rf is a trifluoromethyl group), 0.52 g of the silicon containing alicyclic compound of the above formula (12–1), 4.0 g of 4-methyl-2-pentanone, and 0.74 g of a 1.75 wt % aqueous solution of oxalic acid. The mixture was reacted for six hours at 80° C. while stirring. The reaction was terminated by cooling the flask with ice. The reaction mixture was poured into a separating funnel to remove the water layer. The organic layer was washed with ion-exchanged water until the reaction solution becomes neutral. The solvent was removed from the organic layer to obtain the polysiloxane (1).

NMR spectrum (chemical shift σ) and Mw of the polysiloxane (1) were measured to confirm the following results.
σ: 2.3 ppm (—$CH_2C(CF_3)_2$ group), 1.4 ppm (t-butyl group)
Mw: 1,400

Example 67

Preparation of Polysiloxane (1)

A three-necked flask equipped with a stirrer, a reflux condenser, and a thermometer was charged with 3.34 g of the silicon containing alicyclic compound (2) of the above formula (2-42), 8.62 g of the silicon containing alicyclic compound (4) of the above formula (4-6), (wherein Rf is a trifluoromethyl group), 3.05 g of the silicon containing alicyclic compound of the above formula (12–1), 15 g of 4-methyl-2-pentanone, and 2.88 g of a 1.75 wt % aqueous solution of oxalic acid. The mixture was reacted for six hours at 80° C. while stirring. The reaction was terminated by cooling the flask with ice. The reaction mixture was poured into a separating funnel to remove the water layer. The organic layer was washed with ion-exchanged water until the reaction solution becomes neutral. The solvent was removed from the organic layer to obtain the polysiloxane (1).

NMR spectrum (chemical shift σ) and Mw of the polysiloxane (1) were measured to confirm the following results.
σ: 2.3 ppm (—$CH_2C(CF_3)_2$ group), 1.4 ppm (t-butyl group)
Mw: 1,200

Example 68

Preparation of Polysiloxane (1)

A three-necked flask equipped with a stirrer, a reflux condenser, and a thermometer was charged with 0.85 g of the silicon containing alicyclic compound (2) of the above formula (2-42), 2.63 g of the silicon containing alicyclic compound (4) of the above formula (4-6), (wherein Rf is a trifluoromethyl group), 0.52 g of the silicon containing alicyclic compound of the above formula (12-1), 4.0 g of 4-methyl-2-pentanone, and 0.73 g of a 1.75 wt % aqueous solution of oxalic acid. The mixture was reacted for six hours at 80° C. while stirring. The reaction was terminated by cooling the flask with ice. The reaction mixture was poured into a separating funnel to remove the water layer. The organic layer was washed with ion-exchanged water until the reaction solution becomes neutral. The solvent was removed from the organic layer to obtain the polysiloxane (1).

NMR spectrum (chemical shift σ) and Mw of the polysiloxane (1) were measured to confirm the following results.
σ: 2.3 ppm (—$CH_2C(CF_3)_2$ group), 1.4 ppm (t-butyl group)
Mw: 1,500

Example 69

Preparation of Polysiloxane (1)

A three-necked flask equipped with a stirrer, a reflux condenser, and a thermometer was charged with 0.85 g of the silicon containing alicyclic compound (2) of the above formula (2-42), 2.18 g of the silicon containing alicyclic compound (4) of the above formula (4-6), (wherein Rf is a trifluoromethyl group), 0.97 g of the silicon containing alicyclic compound of the above formula (12-2), 4.0 g of 4-methyl-2-pentanone, and 0.73 g of a 1.75 wt % aqueous solution of oxalic acid. The mixture was reacted for six hours at 80° C. while stirring. The reaction was terminated by cooling the flask with ice. The reaction mixture was poured into a separating funnel to remove the water layer. The organic layer was washed with ion-exchanged water until the reaction solution becomes neutral. The solvent was removed from the organic layer to obtain the polysiloxane (1).

NMR spectrum (chemical shift σ) and Mw of the polysiloxane (1) were measured to confirm the following results.

σ: 2.3 ppm (—CH$_2$C(CF$_3$)$_2$ group), 1.4 ppm (t-butyl group)
Mw: 1,300

Example 70

Preparation of Polysiloxane (1)

A three-necked flask equipped with a stirrer, a reflux condenser, and a thermometer was charged with 0.82 g of the silicon containing alicyclic compound (2) of the above formula (2-42), 2.55 g of the silicon containing alicyclic compound (4) of the above formula (4-6), (wherein Rf is a trifluoromethyl group), 0.63 g of the silicon containing alicyclic compound of the above formula (12-2), 4.0 g of 4-methyl-2-pentanone, and 0.71 g of a 1.75 wt % aqueous solution of oxalic acid. The mixture was reacted for six hours at 80° C. while stirring. The reaction was terminated by cooling the flask with ice. The reaction mixture was poured into a separating funnel to remove the water layer. The organic layer was washed with ion-exchanged water until the reaction solution becomes neutral. The solvent was removed from the organic layer to obtain the polysiloxane (1).

NMR spectrum (chemical shift σ) and Mw of the polysiloxane (1) were measured to confirm the following results.

σ: 2.3 ppm (—CH$_2$C(CF$_3$)$_2$ group), 1.4 ppm (t-butyl group)
Mw: 1,500

Example 71

Preparation of Polysiloxane (1)

A three-necked flask equipped with a stirrer, a reflux condenser, and a thermometer was charged with 0.86 g of the silicon containing alicyclic compound (2) of the above formula (2-6), 1.58 g of the silicon containing alicyclic compound (4) of the above formula (4-6), (wherein Rf is a trifluoromethyl group), 1.55 g of the silicon containing alicyclic compound of the above formula (12-1), 4.0 g of 4-methyl-2-pentanone, and 0.88 g of a 1.75 wt % aqueous solution of oxalic acid. The mixture was reacted for six hours at 80° C. while stirring. The reaction was terminated by cooling the flask with ice. The reaction mixture was poured into a separating funnel to remove the water layer. The organic layer was washed with ion-exchanged water until the reaction solution becomes neutral. The solvent was removed from the organic layer to obtain the polysiloxane (1).

NMR spectrum (chemical shift σ) and Mw of the polysiloxane (1) were measured to confirm the following results.

σ: 2.3 ppm (—CH$_2$C(CF$_3$)$_2$ group), 1.4 ppm (t-butyl group)
Mw: 1,000

Evaluation Example 11

Evaluation of Radiation Transmittance)

The radiation transmittance of coating films with a thickness of 100 nm prepared from the polysiloxanes (1) of Examples 65–71 at wavelengths of 157 nm and 193 nm was measured. The results are shown in Table 7.

TABLE 7

| Polysiloxane | Radiation transmittance (%) | |
|---|---|---|
| | 157 nm | 193 nm |
| Polysiloxane (1) of Example 65 | 47 | 93 |
| Polysiloxane (1) of Example 66 | 45 | 94 |
| Polysiloxane (1) of Example 67 | 48 | 95 |
| Polysiloxane (1) of Example 68 | 49 | 93 |
| Polysiloxane (1) of Example 69 | 44 | 96 |
| Polysiloxane (1) of Example 70 | 46 | 94 |
| Polysiloxane (1) of Example 71 | 43 | 97 |
| Polysiloxane of Comparative Example 9 | 30 | 95 |

The results in the above table shows that the polysiloxanes (1) having a polysiloxane structure for the basic skeleton exhibited radiation transmittance at a wavelength of 193 nm equivalent to or higher than the comparative polysiloxane obtained in Comparative Example 8.

With regard to radiation transmittance at a wavelength of 157 nm, the comparative polysiloxane obtained in Comparative Example 9 exhibited 30% radiation transmittance, whereas the polysiloxanes (1) obtained in Examples 65–71 was found to exhibit radiation transmittance higher than that of the comparative polysiloxane obtained in Comparative Example 9. Conventionally, the radiation transmittance at a wavelength of 157 nm has been thought to decrease as the proportion of hydrocarbon structures in a polysiloxane increases. The results of the measurement, however, indicated that notwithstanding a comparatively large proportion of hydrocarbon structures and varied partial structures in the polymer the polysiloxane (1) exhibited high radiation transmittance at a wavelength of 157 nm.

Evaluation Examples 12

Evaluation of the Dry Etching Resistance

A solution composition was prepared by homogeneously mixing 100 parts of the polysiloxane (1) obtained in Example 65 or polystyrene (Mw=16,000), 1 part of triphenylsulfonium nonafluoro-n-butanesulfonate, 0.04 part of tri-n-octylamine, and 900 parts of 2-heptanone.

The solution composition was applied onto a silicon wafer substrate by spin coating and treated with heat on a hot plate maintained at a temperature of 140° C. for 90 seconds a resist film with a thickness of 100 nm.

The resist films obtained were subjected to the etching test using the etching gases shown in Table 8. The results are shown in Table 8.

TABLE 8

| | Etching rate (nm/min) Resin | | |
|---|---|---|---|
| Etching gas | A Polystyrene | B Polysiloxane (1) | B/A B/A |
| CF3/CF4/N2/C4F6/Ar | 161 | 178 | 1.1 |
| CF4 | 194 | 222 | 1.1 |
| CHF3/CF4/Ar | 118 | 138 | 1.2 |
| C4FG/O2/Ar | 19 | 22 | 1.2 |

The results of Table 8 show that the radiation-sensitive resin composition of the present invention exhibit high dry etching resistance almost equivalent to polystyrene under all etching conditions employed in the evaluation test.

Example 72

Radiation-sensitive Resin Composition

A solution composition was prepared by homogeneously mixing 100 parts of the polysiloxane (1) obtained in Example 65–70, 1 part of triphenylsulfonium nonafluoro-n-butanesulfonate, 0.04 part of tri-n-octylamine, and 900 parts of 2-heptanone.

The solution composition was applied onto a silicon wafer substrate by spin coating and treated with heat on a hot plate maintained at a temperature of 130° C. for 90 seconds a resist film with a thickness of 100 nm.

The resist film was exposed to an ArF excimer laser (wavelength: 193 nm) or F2 excimer laser (wavelength: 157 nm) while changing the irradiation dose, heat-treated for 90 seconds on a hot plate maintained at a temperature of 100° C., and then developed in a 2.38 wt % aqueous solution of tetramethylammonium hydroxide, thereby forming resist patterns.

Observation of the exposed area on the substrate by a scannning-type electron microscope confirmed that the limit resolution shown in Table 9.

TABLE 9

| Polysiloxane | limit resolution ($\mu$m) | |
|---|---|---|
| | ArE | F2 |
| Polysiloxane (1) of Example 65 | 0.14 | 0.10 |
| Polysiloxane (1) of Example 66 | 0.15 | — |
| Polysiloxane (1) of Example 67 | 0.15 | 0.10 |
| Polysiloxane (1) of Example 68 | 0.16 | — |
| Polysiloxane (1) of Example 69 | 0.18 | — |
| Polysiloxane (1) of Example 70 | 0.18 | — |

The polysiloxane (1), polysiloxane (3), and polysiloxane (5) of the present invention exhibit high transparency to radiation of a wavelength of 193 nm or less, particularly to radiation of a wavelength of 157 nm, and exhibits superior dry etching resistance, resolution properties, and developability. Therefore, the radiation-sensitive resin composition containing these polysiloxanes exhibit a high sensitivity to short wavelength radiation and can form fine resist patterns at high precision. The resin composition can be extremely useful for fabricating semiconductor devices, which will become more and more minute in the future. The polysiloxane (1), polysiloxane (3), and polysiloxane (5) are also useful as a material for fabricating formed articles and films, and as laminating materials, components for coating compositions, and the like.

The silicon-containing alicyclic compound (2) and silicon-containing alicyclic compound (4) are useful as raw materials not only for producing the polysiloxane (3) and polysiloxane (5), respectively, but also as raw materials for producing common polysiloxane resins and other silicon-containing alicyclic compounds having similar norbornane-type cyclic structure.

Furthermore, the methods of preparation of the polysiloxane (1), polysiloxane (3), and polysiloxane (5) of the present invention ensure a rapid and homogeneous condensation reaction accompanying hydrolysis, effectively reducing the amount of hydrolysable groups in the raw material left unreacted in the resulting polymer, thereby minimizing absorption of radiation by the hydrolysable groups. Because of this, the resulting polysiloxanes exhibit high radiation tansmittance at a wavelength of 193 nm and less, particularly at 157 nm, exhibit high sensitivity, and have a narrow molecular weight distribution. The radiation-sensitive resin composition prepared from such a polysiloxane is less susceptible to a negative-tone reaction when exposed to radiation with a short wavelength, producing resist patterns exhibiting improved adhesion to substrates and excellent developability. Thus, resist patterns with a fine line width and excellent configuration can be obtained using such a resin composition, particularly when exposed to radiation with a wavelength of 193 nm or less. The polycondensation of a raw material compound under acidic conditions, followed by basic conditions, produces a polysiloxane with increased degrees of polymerization and crosslinking. As a result, the polysiloxane with a high glass transition temperature can be obtained. Fine resist patterns can be formed with extreme advantage using such a polysiloxane.

Obviously, numerous modifications and variations of the present invention are possible in light of the above teachings. It is therefore to be understood that, within the scope of the appended claims, the invention may be practiced otherwise than as specifically described herein.

What is claimed is:

1. A silicon-containing alicyclic compound represented by the following formula (2-A) or (2-B):

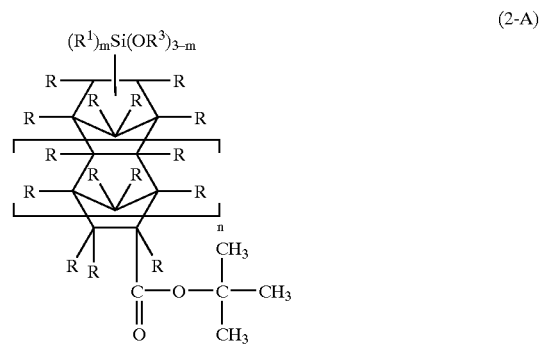

(2-A)

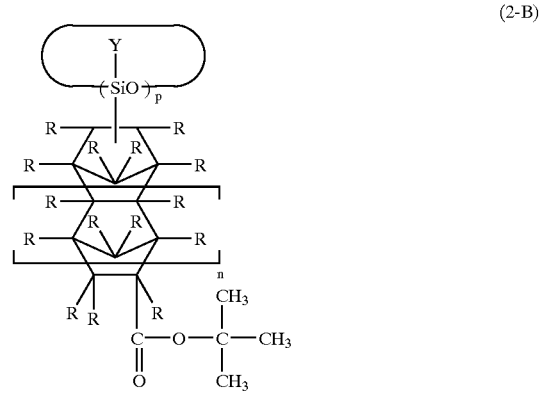

(2-B)

wherein R individually represents a hydrogen atom or a methyl group; $R^1$ individually represents a hydrogen atom, a monovalent hydrocarbon group having 1–20 carbon atoms, a monovalent halogenated hydrocarbon group having 1–20 carbon atoms, a halogen atom, or a primary, secondary, or tertiary amino group; m is an integer of 0–3; n is an integer of 0–3; $R^3$ individually represents a monovalent hydrocarbon group having 1–20 carbon atoms, a monovalent halogenated hydrocarbon group having 1–20 carbon atoms, or the group of the following formula (i):

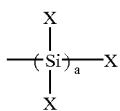

wherein X individually represents a hydrogen atom, a monovalent hydrocarbon group having 1–20 carbon atoms, a monovalent halogenated hydrocarbon group having 1–20 carbon atoms, or a linear, branched, or cyclic alkoxyl group having 1–20 carbon atoms, and a indicates an integer of 1–10, or, when m is 0 or 1, two $R^3$ may form a ring together with two oxygen atoms and the silicon atom; Y individually represents a hydrogen atom, a monovalent hydrocarbon group having 1–20 carbon atoms, a monovalent halogenatod hydrocarbon group having 1–20 carbon atoms, halogen atom, a primary, secondary, or tertiary amino group, or a group $=OR^3$ (wherein $R^3$ is the same as defined above); and p is an integer of 3–10; the silicon atom binding with the 2 or 3 position of the uppermout bicyclo[2.2.1]heptane ring.

2. The compound according to claim 1, wherein n in the formula (2-A) or (2-B) is 0 or 1.

3. A silicon-containing alicyclic compound represented by the following formula (2-A):

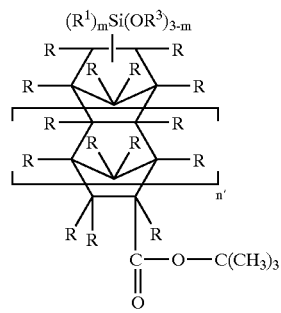

wherein R individually represents a hydrogen atom or a methyl group; $R^1$ individually represents a hydrogen atom, a monovalent hydrocarbon group having 1–20 carbon atoms, a monovalent halogenated hydrocarbon group having 1–20 carbon atoms, a halogen atom, or primary, secondary, or tertiary amino group; m is an integer of 0–3; n is an integer of 0–3; and $R^3$ individually represents a monovalent hydrocarbon group having 1–20 carbon atoms, a monovalent halogenated hydrocarbon group having 1–20 carbon atoms, or the group of the following formula (i):

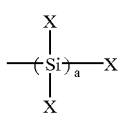

wherein X individually represents a hydrogen atom, a monovalent hydrocarbon group having 1–20 carbon atoms, a monovalent halogenared hydrocarbon group having 1–20 carbon atoms, or a linear, branched, or cyclic alkoxyl group having 1–20 carbon atoms, and a indicates an integer of 1–10, or, when m is 0 or 1, two $R^3$ may form a ring together with two oxygen atoms and the silicon atom; the silicon atom binding with the 2 or 3 position of the uppermost [2.2.1]heptane ring.

4. The compound according to claim 3, wherein m is 1.

5. The compound according to claim 3, wherein m is 1 and $R^1$ is a monovalent hydrocarbon group having 1–20 carbon atoms or a monovalent halogenated hydrocarbon group having 1–20 carbon atoms.

6. The compound according to claim 3, wherein m 0.

7. The compound according to claim 3. wherein m is 0 and $R^3$ is a monovalent hydrocarbon group having 1–20 carbon atoms.

8. The compound according to claim 3, wherein m is 3.

9. The compound accwding to claim 3, wherein m is 3 and $R^1$ individually represents a halogen atom or a primary, secondary, or tertiary amino group.

10. A silicon-containing alicyclic compound represented by the following formula (4-A) or formula (4-B):

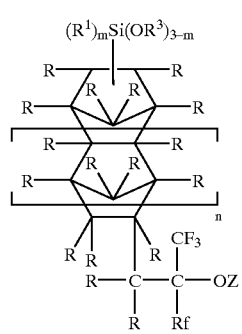

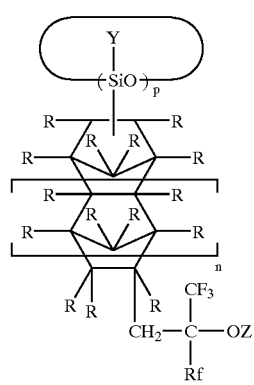

wherein R individually represents a hydrogen atom or a methyl group; $R^1$ individually represents a hydrogen atom, a monovalent hydrocarbon group having 1–20 carbon atoma, a monovalent halogenated hydrocarbon group having 1–20 carbon atoms, a halogen atom, or primary, secondary, or tertiary amino group, m is an integer of 0–3; n is an integer of 0–3; $R^3$ individually represents a monovalent hydrocirban group having 1–20 carbon atoms, a monovalent halogenated hydrocarbon group having 1–20 carbon atoms, or the group of the following formula (i):

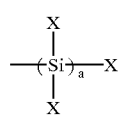

wherein X indiVidAmlly represents a hydrogen atom, a monovalent hydrocarbon group having 1–20 carbon atoms, a monovalent halogenated hydrocarbon group having 1–20 carbon atoms, or a linear, branched, or cyclic alkoxyl group having 1–20 carbon atoms, and a indicates an integer of 1–10, or, when m is 0 or 1, two $R^3$ may form a ring together with two oxygen atoms and the silicon atom; Rf represents a hydrogen atom, methyl group, or trifluoromethyl group; Z represents a hydrogen atom or a monovalent organic group dissociating by the action of an acid to produce hydrogen atom; Y individually represents a hydrogen atom, a monovalent hydrocarbon group having 1–20 carbon atoms, a monovalent halogenated hydrocarbon group having 1–20 carbon atoms, a halogen atom, a primary, secondary, or tertiary amino group, or a group $=OR^3$ (wherein $R^3$ is the same as defined above); and p is an integer of 3–10; the silicon atom binding with the 2 or 3 position of the uppermost bicyclo[2.2.1]heptane ring.

11. The compound according to claim 10, wherein n in the formula (4-A) or (4-B) is 0 or 1.

12. A silicon-containing alicyclic compound represented by the following formula (4-A):

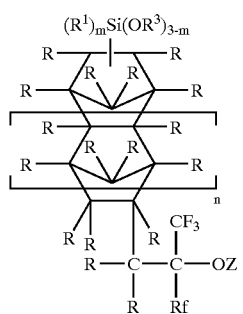

wherein R individually represents a hydrogen atom or a methyl group; n is an integer of 0–3; $R^1$ individually represents a hydrogen atom, a monovalent hydrocarbon group 1–20 carbon atoms, a monovalent halogenated hydrocarbon group having 1–20 carbon atoms a halogen atom, or a primary, secondary, or tertiary amino group; m is an integer of 0–3; $R^3$ individually represents a monovalent hydrocarbon group having 1–20 carbon atoms, a monovalent halogenated hydrocarbon group having 1–20 carbon atoms, or the group of the following formula (i):

$$-(Si)_a-X \quad \text{with X substituents} \quad (i)$$

wherein X individually represents a hydrogen atom, a monovalent hydrocarbon group having 1–20 carbon atoms, a monovalent halogenated hydrocarbon group having 1–20 carbon atoms, or a linear, branched, or cyclic alkoxyl group having 1–20 carbon atoms, and a indicates an integer of 1–10, or, when m is 0 or 1, two $R^3$ may form a ring together with two oxygen atoms and the silicon atom; and Rf represents a hydrogen atom, methyl group, or trifluoromethyl group and Z represents a hydrogen atom or a monovalent organic group dissociating by the action of an acid to produce hydrogen atoms; the silicon atom binding with the 2 or 3 position of the uppermost bicyclo[2.2.1]heptane ring.

13. The compound according to claim 12, wherein m is 1.

14. The compound according to claim 12, wherein m is I and $R^1$ is a monovalent hydrocarbon group having 1–20 carbon atoms or a monovalent halogenated hydrocarbon group having 1–20 carbon atoms.

15. The compound according to claim 12, wherein m is 0.

16. The compound according to claim 12, wherein m is 0 and $R^3$ is a monovalent hydrocarbon group having 1–20 carbon atoms.

17. The compound according to claim 12, wherein m is 0, $R^3$ is monovalent hydrocarbon group having 1–20 carbon atoms, and Rf is a trifluoromethyl group.

18. The compound according to claim 12, wherein m is 0, $R^3$ is monovalent hydrocarbon group having 1–20 carbon atoms, Rf is a trifluoromethyl group, and Z is a hydrogen atom or t-butoxycarbonyl group.

19. The compound according to claim 12, wherein m is 3.

20. The compound according to claim 12, wherein m is 3 and $R^1$ individually represents a halogen atom or a primary, secondary, or tertiary amino group.

* * * * *

UNITED STATES PATENT AND TRADEMARK OFFICE
CERTIFICATE OF CORRECTION

PATENT NO. : 6,846,895 B2  
DATED : January 25, 2005  
INVENTOR(S) : Haruo Iwasawa et al.

It is certified that error appears in the above-identified patent and that said Letters Patent is hereby corrected as shown below:

Column 153,
Line 16, "halogenatod" should read -- halogenated --.
Line 17, "atoms, halogen" should read -- atoms, a halogen --.
Line 21, "uppermout" should read -- uppermost --.

Lines 26-38 (formula (2-A)), " 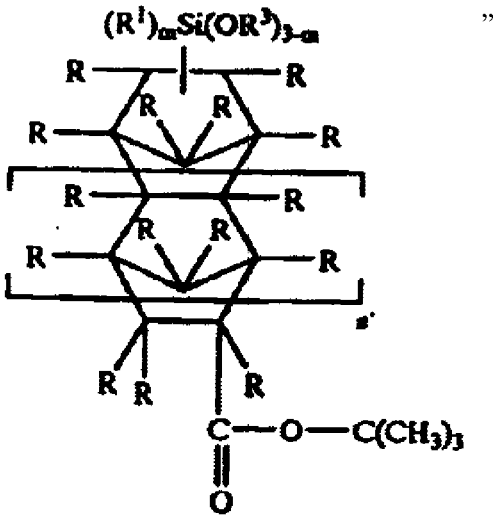 "

should read -- 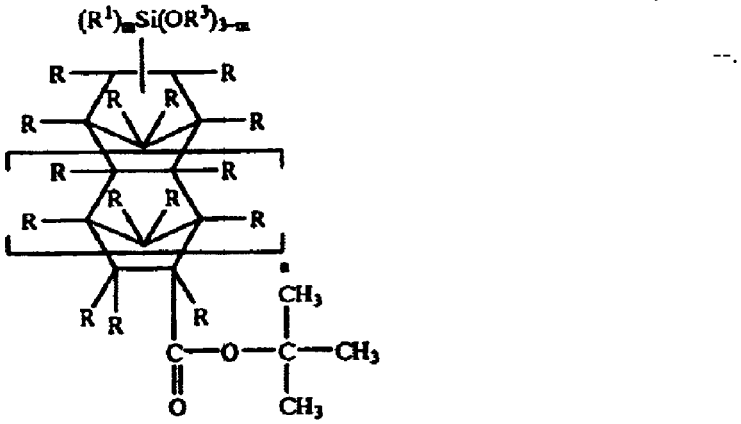 --.

Line 50, "atom, or primary," should read -- atom, or a primary, --.
Line 65, "halogenared" should read -- halogenated --.

UNITED STATES PATENT AND TRADEMARK OFFICE
CERTIFICATE OF CORRECTION

PATENT NO. : 6,846,895 B2
DATED : January 25, 2005
INVENTOR(S) : Haruo Iwasawa et al.

It is certified that error appears in the above-identified patent and that said Letters Patent is hereby corrected as shown below:

Column 154,
Lines 3-4, "uppermost [2.2.1]heptane ring." should read -- uppermost bicyclo[2.2.1] heptane ring. --.
Line 10, "wherein m 0" should read -- wherein m is 0 --.
Line 52, "atoma," should read -- atoms --.
Line 53, "atom, or primary," should read -- atom, or a primary, --.
Line 54, "group, m" should read -- group; m --.
Line 56, "hydrocirban" should read -- hydrocarbon --.
Line 66, "indiVidAmlly" should read -- individually --.

Column 155,
Lines 43-44, "hydrocarbon group 1-20" should read -- hydrocarbon group having 1-20 --.
Line 45, "atoms a halogen" should read -- atoms, a halogen --.

Column 156,
Lines 19-20, "trifluoromethyl group and Z" should read -- trifluoromethyl group; and Z --.
Line 31, "whercin" should read -- wherein --.
Line 35, "$R^3$ is monovalent" should read -- $R^3$ is a monovalent --.
Line 38, "$R^3$ is monovalent" should read -- $R^3$ is a monovalent --.

Signed and Sealed this

Eighteenth Day of October, 2005

JON W. DUDAS
*Director of the United States Patent and Trademark Office*